US005851760A

United States Patent [19]
Evans et al.

[11] Patent Number: 5,851,760
[45] Date of Patent: Dec. 22, 1998

[54] METHOD FOR GENERATION OF SEQUENCE SAMPLED MAPS OF COMPLEX GENOMES

[75] Inventors: Glen A. Evans, San Marcos; Michael W. Smith, San Diego, both of Calif.

[73] Assignee: The Salk Institute for Biological Studies, La Jolla, Calif.

[21] Appl. No.: 117,952

[22] Filed: Sep. 7, 1993

Related U.S. Application Data

[63] Continuation-in-part of Ser. No. 78,471, Jun. 15, 1993, abandoned.
[51] Int. Cl.$^6$ .............................. C12Q 1/68; C12P 19/34
[52] U.S. Cl. ............................................... 435/6; 435/91.1
[58] Field of Search ............................. 435/6, 91.1, 91.3, 435/91.5; 935/78, 80, 26

[56] References Cited

U.S. PATENT DOCUMENTS 5,219,726   6/1993   Evans ........................................... 435/6

OTHER PUBLICATIONS

Bellanne–Chantelot, et al., "Mapping The Whole Human Genome By Fingerprinting Yeast Artificial Chromosomes," *Cell*, 70:1059–1068 (1992).

Bates, et al., "Double cos Site Vectors: Simplified Cosmid Cloning," *Gene*, 26:137–146 (1983).

Chumakov, et al., "Continuum Of Overlapping Clones Spanning The Entire Human Chromosome 21q," *Nature*, 359:380–387 (1992).

Coulson, et al., "Toward A Physical Map Of The Genome Of The Nematode *Caenorhabditis elegans,*" *Proc. Natl. Acad. Sci.(USA)*, 83:7821–7825 (1986).

Cox, et al., "Radiation Hybrid Mapping: A Somatic Cell Genetic Method For Constructing High–Resolution Maps Of Mammalian Chromosomes," *Science*, 250:245–250 (1990).

Daniels, et al., "Analysis Of The *Escherichia coli* Genome: DNA Sequence Of The Region From 84.5 to 86.5 Minutes," *Science*, 257:771–778 (1992).

Delattre, et al., "Mapping Of Human Chromosome 22 with A Panel Of Somatic Cell Hybrids," *Genomics*, 9:721–727 (1991).

Ehrich, et al., "A Family Of Cosmid Vectors With The Multi–Copy R6K Replication Orgin," *Gene*, 57:229–237 (1987).

Evans, et al., "Physical Mapping Of Complex Genomes By Cosmid Multiplex Analysis," *Proc. Natl. Acad. Sci.(USA)*, 86:5030–5034 (1989).

Foote, et al., "The Human Y Chromosome: Overlapping DNA Clones Spanning The Euchromatic Region," 258:60–66 (1992).

Heding, et al., "The Generation Of Ordered Sets Of Cosmid DNA Clones From Human Chromosome Region 11p," *Genomics*, 13:89–94 (1992).

Hermanson, et al., "Cosmid Linking Clones Localized To The Long Arm Of Human Chromosome 11," *Genomics*, 13:134–143 (1992).

Hori, et al., "A High– Resolution Cytogenetic Map Of 168 Cosmid DNA Markers For Human Chromosome 11," *Genomics*, 13:129–133 (1992).

(List continued on next page.)

*Primary Examiner*—Kenneth R. Horlick
*Attorney, Agent, or Firm*—Stephen F. Reiter Gray Cary Ware & Freidenrich

[57] ABSTRACT

The present invention relates to a rapid and powerful sequence "sequence sampled mapping" method for sequencing complex genomes. The invention method is applicable to genomic DNA, preferably mammalian chromosomes, and in a preferred embodiment, employs a "bottom-up" mapping strategy, which allows for the simultaneous analysis of multiple cosmid clones for the detection of overlaps. The sequence sample mapping method is useful first, for the completion of high density sequence-based maps, and ultimately, for the complete sequencing of genomic DNA directly from cosmid clones.

20 Claims, 12 Drawing Sheets

OTHER PUBLICATIONS

Kohara, et al., "The Physical Map Of The Whole E. coli Chromosome: Application Of A New Strategy For Rapid Analysis And Sorting Of A Large Genomic Library," *Cell,* 50:495–508 (1987).

Lander, et al., "Genomic Mapping By Fingerprinting Random Clones: A Mathematical Analysis," *Genomics,* 2:231–239 (1988).

Lichter, et al., "Rapid Detection Of Human Chromosome 21 Abberations By in situ Hybridization," *Proc. Natl. Acad. Sci.(USA),* 85:9664–9668 (1988).

Martin–Gallardo, et al., "Automated DNA Sequencing And Analysis Of 106 Kilobases From Human Chromosome 19q13.3," *Nat. Genet.,* 1:34–39 (1992).

Olson, et al., "Random–Clone Strategy For Genomic Restriction Mapping In Yeast," *Proc. Natl. Acad. Sci.(USA),* 83:7826–7830 (1986).

Oliver, et al., "The Complete DNA Sequence Of Yeast Chromosome III," *Nature,* 357:38–46 (1992).

Olson, et al., "A Common Language For Physical Mapping Of The Human Genome," *Science,* 245:1434–1435 (1989).

Poustka, et al., "Jumping Libraries And Linking Libraries: The Next Generation Of Molecular Tools in Mammalian Genetics," *Trends Genetics,* 2:174–179 (1986).

Saiki, et al., "Primer–Directed Enzymatic Amplification Of DNA With A Thermostable DNA Polymerase," *Science,* 239:487–491 (1988).

Sulston, et al., "The *C. elegans* Genome Sequencing Project: A Beginning," *Nature,* 356:37–41 (1992).

Tanigami, et al., "Mapping Of 262 DNA Markers Into 24 Intervals On Human Chromosome 11," *Am. J. Hum. Genet.,* 50:56–64 (1992).

Wahl, et al., "Northern and Southern Blots," *Methods in Enzymology,* 152:572–581 (1987).

Wahl, et al., "Cosmid Vectors For Rapid Genomic Walking, Restriction Mapping, and Gene Transfer," *Proc. Natl. Acad. Sci.(USA),* 84:2160–2164 (1987).

Wilson, et al., "Nucleotide Sequence Analysis of 95 kb Near The 3' End Of The Murine T–Cell Receptor α/ δChain Locus: Strategy And Methodology," *Genomics,* 13:1198–1208 (1992).

Voss et al., *Nucleic Acids Res.* 18(4), 1066 (1990).

Palca, *Nature* 325, 651 (1987).

Evans et al., *Gene* 79, 9–20 (1989).

Contig #2:

```
17,6    --->    3,12
17,6 ---> 10,16
         10,16 ---> 3,12
                    3,12 ---> 19,27
                    19,27 ---> 3,12
                               3,12 ---> 10,6
                                         10,6 <-- 1,3
                                                  1,3 <-- 10,1
                                                          10,1 ---> 2,20
         14,23 <-- 3,12
3,12 <-- 14,23
``` cGR-62e12-u(GLNK)

```
                *          *   *       * *    ****          *
CDK3    MDMFQKVEKIGEGTYGVVYKAKNRETGQLVALKKIRLDLEMEGVPSTAIREISLLKELKHPNIVRLLDVVHNERKLYL..
CDC2    MEDYIKIEKIGEGTYGVVYKGRHRVTGQIVAMKKIRLESEEEGVPSTAIREISLLKELRHPNIVSLQDVLMQDSRLYL..
KKIA    MMEKYEKIGKIGEGSYGVVFKCRNRDTGQIVAIKKFLESEDDPVIKKIALREIRMLKQLKHPNLVNLLEVFRRKRRLHL..
GLNEK          MYIKNRILGRGAYGIAWLAKDTETGASVVIKELTLAQLPAAERERALREANLLSQLFHPNIVSYKQSFLENGALNT..
NEK1    MEKYVRLQKIGEGSFGKAVLVKSTEDGRHYVIKEINISRMSDKERQESRREVAVLANMKHPNIVQYKESFEENGSLYI..
```

Figure 5A cGR-6a6-u and cGR-15c7-t (GLNIMA)

```
        **                                        *                    *       *  *
NIMA    ..FG        IIRKVKRKSDGFILCRKEINYIKMSTKEREQLTAEFNILSSLRHPNIVAYYHREHLKASQDLYLYMEYCGGGDL
KIN3    ..FG        SVRKVIHIPTKKLLVRKDIKYGHMNSKERQQLIAECSILSQLKHENIVEFYNWDFDEQKEVLYLYMEYCSRGDL
GLNIMA  ..FGTRGSGTVTGPSVQZWKSRARLCSQGSQYYKYTGQVQICVRNDFIKLCSLSHKNLVKYDYVYNDTKNLGHFVMEYYERCCL

*                    *      *              **    **          *
NIMA    SMVIKNLKRTNKYAEEDFVWRILSQLVTALYRCHYGTDPAEVGSNLLGPAPKPSGLKGKQAMTILHRDLKPENIFLGSDNT..
KIN3    SQMIKHYKQEHKYIPEKIVWGILAQLLTALYKCHYGVELPTL TTIYDRM KPP VKGKN    IVIHRDLKPGNIFLSYDDS..
GLNIMA  MDVILFYRMKERVIPEETVWYILSHLAEALL    YY  HSPQKDNTDMGP               LVHRNIKPSKVFLAADGY..
```

Figure 5B

•repetitive DNA similar to 3' noncoding region surace antigen gene, G. lamblia

```
cGR-38b8-t:    9  CATCTGTNACTCACCCCTCTGTGTGCTCTGTGGTCTGTGAGTGCCTCCACCCAGACAACGC
                  ||||||| ||||||||||||||||||||||||| |||||||||||||||||||||||||||
Sbjct:       677  CATCTGTGACTCACCCCTCTGTGTGCTCTGTGGTCTGTGAGTGCCTCCACCCAGACAACGC cGR-38b8-t:       CTCAGGAGCCGTGCACACCGGGACAGAGAGGATGACCAAGGGGTCAAGCAGCCCCGCTA
                  |||||||||||||||||||||||||||||||||||||||||||||||||||||||||||
Sbjct:            CTCAGGAGCCGTGCACACCGGGACAGAGAGGATGACCAAGGGGTCAAGCAGCCCCGCTA cGR-38b8-t:       CGAGAGATGAGAGTGCACAGCAACCAGCCTGATC    162
                  ||||||||||||||||||||||||||||||||||
Sbjct:            CGAGAGATGAGAGTGCACAGCAACCAGCCTGATC    830
```

Figure 5C

•surface protein 11, G. lamblia

```
cGR-45h5-t:  242  TGSEPNTCKACSAVINGKXYCSQCNS   319
                  TG    CK C      I+G   YCS+C++
Sbjct:       414  TGQGSGACKTCGLTIDGASYCSECDT   439
```

•major trophozoite antigen tsaa, G. lamblia

```
cGR-41h1-u:  237  TGSEPNTCKACSAVINGKKYCSQCNS   314
                  TG+ + +CK+C+    I+G   YCS+C +
Sbjct:       466  TGTGAGACKTCGLTIDGASYCSECAT   491
```

Figure 5D variable surface proteins, G. lamblia similarity to cGR-45h5-t and cGR-41h1-u

```
                                                   **        *          * *  ***         * *
cGR-45h5-t+41h1-u  ..QASHMKVESARPHLSVQTHAEGLPCQcVM HRQMPRRGGLVNRAVMAcVT DAGTMF YAVLLIGLML
TSAA               ..GATEGAKKLCKECTAANCKTCDDQGQcQACNDGFYKNGDACSPCHEScKTCSAGTASDCTECPTGKAL
TSP11              ..GTNADNKKACKECTVANCKTCNDQGQcQTCNDGFYKNGDACSPCHEScKTCSAGTASDCTECPTGKAL

*  * *   **    ** *   * *  *** *      *             *
cGR-45h5-t         EMARAAQAGDEcEE  VTGSEPNTcKAcSAVINGKKYcSQcNSGG  SQSAPTDGKCTTATTEcSQKQD..
TSAA               KYGDDGTKG TcGEGCTTGTGAGAcKTcGLTIDGASYcSEcATTTEYPQNGVCAPKASRATPTcNDSPI..
TSP11              KYGNDGTKG TcGEGCTTGQGSGAcKTcGLTIDGASYcSEcDTQNEYPQNGICTSTTARTVATcKNSNV..
```

Figure 5E variable surface proteins, G. lamblia similarity to cGR-41e11-u

```
                         *  * *                  *    *  **    **** *   **
CGR-41e11-u        ..GNDPXDGVcTSIXA TARXASXCKASGGKXTEcGANYALXSGGcYNTQKLPGSSX
VSP1267            ..GYAPIDGIcTAVAA AGRDVSVCTATGGKCTAcTGNYALLSGGcYNTQTLPGKSV
TSAA               ..TEYPQNGVcAPKASRATPTCNDSPIQNGVCGTcADNYFKMNGGcYETVKYPGKTV

*    *      * *         *   *      ** *  ** *
CGR-41e11-u        cTAAQNKXXX  QTXANGQSP AGGXF PAcTXXcL  KXAXSKETcTDcLAGYYKG..
VSP1267            cKAVANSNDGKCKTCANGQAPDPATNFCPLcDSTcAECSTKNDADAcTKcFPGYYKT..
TSAA               cLSAPNGGT  CQKAADGYKLDSGTL  TVcSEGc   KECASSTDcTTcLDGYVKS..
```

Figure 9A mitochondrial acetoacetyl-CoA thiolase, human

```
D11S384      1   KLEDLIVKDGLTDVYNKIHM  60
                 ||||||||||||||||||||
HUMMAT12   174   KLEDLIVKDGLTDVYNKIHM 193
```

UDP-N-acetylglucosamine--dolichyl-phosphate
N-acetylglucosaminephosphotransferase, hamster

```
c11q-2b11-t 302  ALIGALLAICCMIFLGFADDVLNLRWRHKLLLPTAASLPLLMYFTNFGKTTIVVPKPFRPILGLHLDLG  93
                 ||||||||||||||||||||||||||||||||||||||||||||||||| ||||||+||||| ||||||
UAGT_CRIGR   97  ALIGALLAICCMIFLGFADDVLNLRWRHKLLLPTAASLPLLMYFTNFGNTTIVVPKPFRWILGLHLDLG 166
``` postsynaptic density protein, rat

```
RATPSD95A_1 362      VNGVDLRNASHEQAAIALKNAGQTVTIIAQYKPE 395
                     ||+|||||||||||| ||||| |||||||||+||
c11q-2e4-t  148  LFQVNGIDLRGASHEQAAAAALKGAGQTVTIIAQYQPE 249
                  | ||++  || ||++ +| ||+| || |||||||+||
DRCDLGA_1   532  LLSVNNVNLTHATHEEAAQALKTSGGVVTLLAQYRPE 568
``` discs-large tumor suppressor, fruit fly

Zinc-finger protein ZFP-37, mouse

```
cSRL-4a3-t  336  LKVHQRIHTGEKPYQCSDCGKSFTHGSTLKVHQRIHTGXKPYNCNVCGKCFMKGSTLQAH 157
                 | |||||||||||| || | ||| | +|   |||||||+|||+|+ | || || || ||
ZF37_MOUSE  285  LTDHLRIHTGEKPYKCNECGKTFRHSSNLMQHLRSHTGEKPYECKECGKSFRYNSSLTEH 344
``` retrovirus related POL polyprotein, human

```
cSRL-5f2-t  131  TTTSAEHFTGKKNSPHEGKRIWWKDNKNKTWEIGKVITWGRGFACFSAGENQLPVWXPTR 310
                 ||++ +|  ||||||||||  ||||||||||||||||||||||||| |+||||||| |||
POL1_HUMAN  793  TTSAEQHLTGKKNSPHEGKLIWWKDNKNKTWEIGKVITWGRGFACVSPGENQLPVWLPTR 852
```

```
opioid binding protein/cell adehesion molecule, cow cSRL-7d2-t      1    PPDITVNXGSSVTLLCLAIGRPEPT  75
                     ++|+||| |||||||||||||||||
CPC4_BOVIN    142    SSDVTVNEGSSVTLLCLAIGRPEPT  166 env polyprotein - feline endogenous virus ECE1 cSRL-6g5-t      1    PLAKVVLQCXRALNMPYMEQGGYCMALREKCCFYTNHLGIIRDNMAMLK  147
                     +|+ ||||  |+|++ ++++|| | ||+| ||||++| ||+||+|| |+
PIR:VCMVCE    533    SLLEVVLQNRRGLDLLFLQEGGLCAALKEECCFYADHTGIVRDSMAKLR  581 mitochondrial carnitine palmitoyltransferase II precursor, human cSRL-2c2-t    226    SRRWFDKSFTFVVFKNGKMGLNAEHSWADAPIVAHLWEVSF  104
                     + |||||||  ++ |+|  +++ |||| |+ +| +  +  |
CPT2_HUMAN    348    TNRWFDKSFNLIIAKDGSTAVHFEHSWEDGVAVLRFFNEVF  388 trans-acting T-cell specific transcription factor GATA-3, mouse cSRL-2g6-t    128    GGKALSGRTSSSAWKGACF*KDSIHTFCP  214
                     ||||||++ ++|+|+ + | | |||   |
GAT3_MOUSE     98    GGKALSSHHTASPWNLSPFSKTSIHHGSP  126
```

Figure 9B

SEQUENCE LISTING ( 1 ) GENERAL INFORMATION:

( i i i ) NUMBER OF SEQUENCES: 797

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:1:

TCTGTCTGGA AGAGCGTGG 19

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:2:

CCAGACCAAG TCTTGGACCT 20

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:3:

CCATAAATGA AAGGTTTGGA TG 22

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:4:

GCGACTTGAG CTGTCATGC 19

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:5:

TGGCATTATA GGTGCCCG 18

( 2 ) INFORMATION FOR SEQ ID NO:6:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:6:

CTCAGGAAAC AGGGAGATGC 20

( 2 ) INFORMATION FOR SEQ ID NO:7:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:7:

CCAGGAAGGG TTCCCTGAAG TAGGTG 26

( 2 ) INFORMATION FOR SEQ ID NO:8:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:8:

ATAAGCTGCT GCTACCTACA GCTGCC 26

( 2 ) INFORMATION FOR SEQ ID NO:9:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:9:

AGAAAACTGA TTAACCAAGG CA 22

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:10:

AGCAAATCTC GTCTCAAAAA AA 22

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:11:

TCCAGTAGGA AGAGATGCAG G 21

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:12:

GGATTCCTTC TACTCTCCCA GG 22

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:13:

AGCTGTGGGT TCATAATGGC 20

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:14:

AGGTGAAGAG GAGGAGAGTG C        21

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:15:

CCTGTGGCCT CCTATGACAT        20

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:16:

TGAGGCCTCT CTTCTCTCAT G        21

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:17:

CTTGGGAGTC ACTGAACTGA TG        22

( 2 ) INFORMATION FOR SEQ ID NO:18:

( i ) SEQUENCE CHARACTERISTICS:

( A ) LENGTH: 20 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:18:

CCCACATCCC TAAACTGGAA                                                                                20

( 2 ) INFORMATION FOR SEQ ID NO:19:

( i ) SEQUENCE CHARACTERISTICS:
             ( A ) LENGTH: 21 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:19:

AGGAAACTGA GGAACAGAGC A                                                                              21

( 2 ) INFORMATION FOR SEQ ID NO:20:

( i ) SEQUENCE CHARACTERISTICS:
             ( A ) LENGTH: 20 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:20:

GGCTGGCCTG GAGTTAACTA                                                                                20

( 2 ) INFORMATION FOR SEQ ID NO:21:

( i ) SEQUENCE CHARACTERISTICS:
             ( A ) LENGTH: 24 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:21:

CTAGCATGTG AGGGTGTTGG AGGT                                                                           24

( 2 ) INFORMATION FOR SEQ ID NO:22:

( i ) SEQUENCE CHARACTERISTICS:
             ( A ) LENGTH: 24 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:22:

AATCACACTC TTGGTGGGTT TTCG 24

( 2 ) INFORMATION FOR SEQ ID NO:23:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:23:

AACACCAACA TCACAAAAGA AA 22

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:24:

ACTGACAAGA GCTTGCTGCA 20

( 2 ) INFORMATION FOR SEQ ID NO:25:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:25:

AGCACACCCG GTGGTATG 18

( 2 ) INFORMATION FOR SEQ ID NO:26:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:26:

AGATGATGCC CTTCCCCC 18

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:27:

GGTCCCCTCT AAGAAGCACC 20

( 2 ) INFORMATION FOR SEQ ID NO:28:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:28:

CTTTTCCAAG TGCCAGCCT 19

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:29:

TTATAGGCGC CTGCACCACG TCT 23

( 2 ) INFORMATION FOR SEQ ID NO:30:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:30:

TCAAGAGGTT GAAGCAGTGA GCCGTG 26

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:31:

CACCATGCAA TCTGCAGC 18

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:32:

ATTTCTGCCT GCTGATCCAT 20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:33:

TAGGAACCCC CATCATTCCA 20

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:34:

CCATGGAGGT CCCCTTTC 18

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:35:

AAGCTCTCTG GGAAATAAAG GG        22

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:36:

AACAAACTCA TGAATGCCTG G        21

( 2 ) INFORMATION FOR SEQ ID NO:37:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:37:

GTGTGGGGCC ACTGTATTG        19

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:38:

TGGCAACAAA AGCAAGACTG        20

( 2 ) INFORMATION FOR SEQ ID NO:39:

( i ) SEQUENCE CHARACTERISTICS:
        ( A ) LENGTH: 21 base pairs ( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:39:

AAGGAAGGAA GGAAGGAAAG G 21

( 2 ) INFORMATION FOR SEQ ID NO:40:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:40:

CTGATAGCCT GACCTGACTG TG 22

( 2 ) INFORMATION FOR SEQ ID NO:41:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:41:

GGAGAGGACA TTAACCAGCT GA 22

( 2 ) INFORMATION FOR SEQ ID NO:42:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:42:

GTGATGGGTT GCATAGTGTC TG 22

( 2 ) INFORMATION FOR SEQ ID NO:43:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:43:

GAGAGTGGAA GCAAAGGCTG 20

(2) INFORMATION FOR SEQ ID NO:44:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:44:

CTCCTTCCT TACCCTACAA CC 22

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:45:

ACTGGGGACC CCATGACT 18

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:46:

GGGCTCCTGC TCTACCTCTT 20

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO ( i v ) ANTI-SENSE: NO ( x i ) SEQUENCE DESCRIPTION: SEQ ID NO:47:

ACTGTGTGGG GAGAAGGTAC C 21

( 2 ) INFORMATION FOR SEQ ID NO:48:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:48:

TGCTGGTAAC TTACCACTGT GC 22

( 2 ) INFORMATION FOR SEQ ID NO:49:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:49:

CCACCATATC CTGCGAAATT 20

( 2 ) INFORMATION FOR SEQ ID NO:50:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:50:

GGTTGCAAGA TCACGTCACT 20

( 2 ) INFORMATION FOR SEQ ID NO:51:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:51:

CAGCTTTACT TTTATTTACA GAGGTTT 27

( 2 ) INFORMATION FOR SEQ ID NO:52:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:52:

CTAGAACTTC CTGGTTTAAA CGAAA 25

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:53:

GCTTGCTGCA ATGTTTTTCA 20

( 2 ) INFORMATION FOR SEQ ID NO:54:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:54:

CTGGCTGCTA AAAGAAGAGA CC 22

( 2 ) INFORMATION FOR SEQ ID NO:55:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:55:

GAGTTTGGAG CAAGCCAGTC 20

( 2 ) INFORMATION FOR SEQ ID NO:56:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:56:

TGACCTTGAT GCTCACTTGG      20

( 2 ) INFORMATION FOR SEQ ID NO:57:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:57:

AAGTCACACA GCTAGCAAAT GG      22

( 2 ) INFORMATION FOR SEQ ID NO:58:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:58:

TGTCCTTGAC GGAATAGATT CC      22

( 2 ) INFORMATION FOR SEQ ID NO:59:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:59:

GGTCAGGCCA CACCTCAC      18

( 2 ) INFORMATION FOR SEQ ID NO:60:

( i ) SEQUENCE CHARACTERISTICS:
    ( A ) LENGTH: 20 base pairs
    ( B ) TYPE: nucleic acid ( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:60:

ATACCCTTCA GGTGGATCCC 20

( 2 ) INFORMATION FOR SEQ ID NO:61:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:61:

GCTGTCAGAC TGAAGACCCT G 21

( 2 ) INFORMATION FOR SEQ ID NO:62:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:62:

ACTGCCAGCC TGGTCAGAG 19

( 2 ) INFORMATION FOR SEQ ID NO:63:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:63:

TTCAGCACTC CTTACATTGC C 21

( 2 ) INFORMATION FOR SEQ ID NO:64:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Oligonucleotide (  i i i ) HYPOTHETICAL: NO (  i v ) ANTI-SENSE: NO (  x i ) SEQUENCE DESCRIPTION: SEQ ID NO:64:

TCCAACTGAA ACAGCCTGC  19

( 2 ) INFORMATION FOR SEQ ID NO:65:

(  i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i ) MOLECULE TYPE: Oligonucleotide (  i i i ) HYPOTHETICAL: NO (  i v ) ANTI-SENSE: NO (  x i ) SEQUENCE DESCRIPTION: SEQ ID NO:65:

GCACTCCTGT CTTGGTCCAT  20

( 2 ) INFORMATION FOR SEQ ID NO:66:

(  i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i ) MOLECULE TYPE: Oligonucleotide (  i i i ) HYPOTHETICAL: NO (  i v ) ANTI-SENSE: NO (  x i ) SEQUENCE DESCRIPTION: SEQ ID NO:66:

AGGGATCCAT CTTGGAAGCT  20

( 2 ) INFORMATION FOR SEQ ID NO:67:

(  i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i ) MOLECULE TYPE: Oligonucleotide (  i i i ) HYPOTHETICAL: NO (  i v ) ANTI-SENSE: NO (  x i ) SEQUENCE DESCRIPTION: SEQ ID NO:67:

CCAAGGACAG GCAGTAGAGC  20

( 2 ) INFORMATION FOR SEQ ID NO:68:

(  i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i ) MOLECULE TYPE: Oligonucleotide (  i i i ) HYPOTHETICAL: NO (  i v ) ANTI-SENSE: NO ( x i ) SEQUENCE DESCRIPTION: SEQ ID NO:68:

CAATGAAATG ATGCAGTGTG G  21

( 2 ) INFORMATION FOR SEQ ID NO:69:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:69:

CCTCAGTCCT TTGCACTTG  19

( 2 ) INFORMATION FOR SEQ ID NO:70:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:70:

TCTGGCTATT TTGTACAGGG  20

( 2 ) INFORMATION FOR SEQ ID NO:71:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:71:

GCCCTCTAGT CATGCCACAT  20

( 2 ) INFORMATION FOR SEQ ID NO:72:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:72:

ACGCGAAACC AGATCATTCT  20

( 2 ) INFORMATION FOR SEQ ID NO:73:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:73:

CAACCAAAAT AAAAGGCCTC C     21

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:74:

GTGTTCTTCT CTTGCACCTG C     21

( 2 ) INFORMATION FOR SEQ ID NO:75:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:75:

GCAGGTTTTT CAAGAAGGTA TG     22

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:76:

GGCAGCCATT TTCTTACCAA     20

( 2 ) INFORMATION FOR SEQ ID NO:77:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:77:

CATGCAGGTG TCAGGACG                                       18

( 2 ) INFORMATION FOR SEQ ID NO:78:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:78:

GATACCAGAG AGATTGCATC CC                                  22

( 2 ) INFORMATION FOR SEQ ID NO:79:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:79:

GATGCCATGC TGGGTTAAAC                                     20

( 2 ) INFORMATION FOR SEQ ID NO:80:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:80:

TCATCTTAAG CCCATTCTCT CC                                  22

( 2 ) INFORMATION FOR SEQ ID NO:81:

( i ) SEQUENCE CHARACTERISTICS:
    ( A ) LENGTH: 20 base pairs
    ( B ) TYPE: nucleic acid
    ( C ) STRANDEDNESS: single ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:81:

CGACCCTGGG TGTTAACAAC                                                   20

( 2 ) INFORMATION FOR SEQ ID NO:82:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:82:

AAAGGAACGT GTTACCGCTG                                                   20

( 2 ) INFORMATION FOR SEQ ID NO:83:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:83:

GTTGATGAGC CAGACAAAAC TG                                                22

( 2 ) INFORMATION FOR SEQ ID NO:84:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:84:

TATGCAGTGA TGTTAGGTTT GC                                                22

( 2 ) INFORMATION FOR SEQ ID NO:85:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:85:

GTCCAATACG GTAGCCACTA GC        22

( 2 ) INFORMATION FOR SEQ ID NO:86:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:86:

CGATCTAGAG CTGTGCTGTC C        21

( 2 ) INFORMATION FOR SEQ ID NO:87:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:87:

CGCAAGACTA ACAAGGCCTC        20

( 2 ) INFORMATION FOR SEQ ID NO:88:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:88:

GAAACATTGC ATATCCTGAT GC        22

( 2 ) INFORMATION FOR SEQ ID NO:89:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:89:

GACACACCAT GAAGCACACC 20

( 2 ) INFORMATION FOR SEQ ID NO:90:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:90:

AGAGCCAATC TGCAAAGACT G 21

( 2 ) INFORMATION FOR SEQ ID NO:91:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:91:

CGAGACTCCA TCTCAGAAAA A 21

( 2 ) INFORMATION FOR SEQ ID NO:92:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:92:

TCTATCTGTG GTGCCCCAG 19

( 2 ) INFORMATION FOR SEQ ID NO:93:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:93:

GCCCTATGTA CTTTCTGTTG GC 22

( 2 ) INFORMATION FOR SEQ ID NO:94:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:94:

ACAGGAAGCT CAGGGCACTA                       20

( 2 ) INFORMATION FOR SEQ ID NO:95:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:95:

AAGCAACTTC CACATTCAAG TG                    22

( 2 ) INFORMATION FOR SEQ ID NO:96:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:96:

GTGCAATGTC CCCTCATTTT                       20

( 2 ) INFORMATION FOR SEQ ID NO:97:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:97:

AGGCTTTTCT AAACCTTCTC CC                    22

( 2 ) INFORMATION FOR SEQ ID NO:98:

( i ) SEQUENCE CHARACTERISTICS:

(A) LENGTH: 19 base pairs
                (B) TYPE: nucleic acid
                (C) STRANDEDNESS: single
                (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:98:

ACGGAGGCAG ATTCCTTTG                                                                        19

(2) INFORMATION FOR SEQ ID NO:99:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:99:

CAGTAACTCC CAGGGCTCC                                                                        19

(2) INFORMATION FOR SEQ ID NO:100:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:100:

CACTCACTGT AAATGCAGCC A                                                                     21

(2) INFORMATION FOR SEQ ID NO:101:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:101:

CCCACAAATA CCAAGATGAC TG                                                                    22

(2) INFORMATION FOR SEQ ID NO:102:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:102:

ACATCAATTT TGGCTGAGCC  20

(2) INFORMATION FOR SEQ ID NO:103:

(i) SEQUENCE CHARACTERISTICS:
 (A) LENGTH: 22 base pairs
 (B) TYPE: nucleic acid
 (C) STRANDEDNESS: single
 (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:103:

TCTTGGAGTC AGCAATTATC AA  22

(2) INFORMATION FOR SEQ ID NO:104:

(i) SEQUENCE CHARACTERISTICS:
 (A) LENGTH: 22 base pairs
 (B) TYPE: nucleic acid
 (C) STRANDEDNESS: single
 (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:104:

TACCTGCTTT TGTGCTACAA AG  22

(2) INFORMATION FOR SEQ ID NO:105:

(i) SEQUENCE CHARACTERISTICS:
 (A) LENGTH: 20 base pairs
 (B) TYPE: nucleic acid
 (C) STRANDEDNESS: single
 (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:105:

ACAGAGGAGA GTGGCTGGAA  20

(2) INFORMATION FOR SEQ ID NO:106:

(i) SEQUENCE CHARACTERISTICS:
 (A) LENGTH: 20 base pairs
 (B) TYPE: nucleic acid
 (C) STRANDEDNESS: single
 (D) TOPOLOGY: linear (ii) MOLECULE TYPE: Oligonucleotide (iii) HYPOTHETICAL: NO ( i v ) ANTI-SENSE: NO ( x i ) SEQUENCE DESCRIPTION: SEQ ID NO:106:

GGCACTGGGG AAATACTGAA 20

( 2 ) INFORMATION FOR SEQ ID NO:107:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:107:

TTGTCAGGTT CAGCAAGCAG 20

( 2 ) INFORMATION FOR SEQ ID NO:108:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:108:

CTAAAATAAC AAAAGCCGCC C 21

( 2 ) INFORMATION FOR SEQ ID NO:109:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:109:

CTCCAGGGAA GCTGACTGAC 20

( 2 ) INFORMATION FOR SEQ ID NO:110:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:110:

```
   TCTAGGGTAG GGGAGTTTCT CC                                                      22
```

(2) INFORMATION FOR SEQ ID NO:111:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:111:

```
   AAGAATACAG GATATTGTGG CG                                                      22
```

(2) INFORMATION FOR SEQ ID NO:112:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:112:

```
   TAGTTGACCT GAATCTTTGG GA                                                      22
```

(2) INFORMATION FOR SEQ ID NO:113:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:113:

```
   TCTGTCACGG ACAGCAATTC                                                         20
```

(2) INFORMATION FOR SEQ ID NO:114:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:114:

```
   AGTTTGAACA TGAGATTGCA GC                                                      22
```

( 2 ) INFORMATION FOR SEQ ID NO:115:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:115:

TGGGCTGGAC AGGAGAAC        18

( 2 ) INFORMATION FOR SEQ ID NO:116:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:116:

AAGCATGCCC TCAGAATGAC        20

( 2 ) INFORMATION FOR SEQ ID NO:117:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:117:

TTGTAGAGCT TTTTCTCCTC CCTA        24

( 2 ) INFORMATION FOR SEQ ID NO:118:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:118:

CTTAAGTAAA ATTTCAGGAT ACAAATT        27

( 2 ) INFORMATION FOR SEQ ID NO:119:

( i ) SEQUENCE CHARACTERISTICS:
        ( A ) LENGTH: 20 base pairs ( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:119:

CGGGAGAAAC TAGAGGCAGA 20

( 2 ) INFORMATION FOR SEQ ID NO:120:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:120:

AACTCTGAGG GGAGCAGTCA 20

( 2 ) INFORMATION FOR SEQ ID NO:121:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:121:

TGTAAGCTGC GTGGCATAAG 20

( 2 ) INFORMATION FOR SEQ ID NO:122:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:122:

ATGTGTGTGA GCAGAGCCTG 20

( 2 ) INFORMATION FOR SEQ ID NO:123:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:123:

TGCTTGGTTT TTCAGCATTG    20

(2) INFORMATION FOR SEQ ID NO:124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:124:

ATATTGTCAT GCAGCTGGCA    20

(2) INFORMATION FOR SEQ ID NO:125:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:125:

GGGTTTCTGA GGCATGTGAT    20

(2) INFORMATION FOR SEQ ID NO:126:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:126:

AATGAGGGTA CAGATCCACA CA    22

(2) INFORMATION FOR SEQ ID NO:127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO ( i v ) ANTI-SENSE: NO ( x i ) SEQUENCE DESCRIPTION: SEQ ID NO:127:

ATACCAAAGC CCCTAAAACA TG    22

( 2 ) INFORMATION FOR SEQ ID NO:128:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:128:

GTATCATATT TGCTGCTTCC CT    22

( 2 ) INFORMATION FOR SEQ ID NO:129:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:129:

ACCGGACTCC CTTTCCAC    18

( 2 ) INFORMATION FOR SEQ ID NO:130:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:130:

TTGTCTACAA ATCCCCCTCG    20

( 2 ) INFORMATION FOR SEQ ID NO:131:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:131:

TGTCCATGCC TATGTCCTGA 20

(2) INFORMATION FOR SEQ ID NO:132:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:132:

GGTGTTGGGA AAACTGGCTA 20

(2) INFORMATION FOR SEQ ID NO:133:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:133:

ACAGTTGATT ATCCGATCAG GG 22

(2) INFORMATION FOR SEQ ID NO:134:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:134:

AGGATGGAGA TGTCTTTGTT GG 22

(2) INFORMATION FOR SEQ ID NO:135:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:135:

GTCTCTGGGA CAGATTCCTC A 21

(2) INFORMATION FOR SEQ ID NO:136:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:136:

TGCACATCTG TCCTGCTATT T    21

( 2 ) INFORMATION FOR SEQ ID NO:137:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:137:

GGAAGACAAA TCCCAATGGA    20

( 2 ) INFORMATION FOR SEQ ID NO:138:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:138:

GAGCCCAAGC GTAGGAAAC    19

( 2 ) INFORMATION FOR SEQ ID NO:139:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:139:

ATGAGTCCCG TCATACTGTG C    21

( 2 ) INFORMATION FOR SEQ ID NO:140:

( i ) SEQUENCE CHARACTERISTICS:
        ( A ) LENGTH: 20 base pairs
        ( B ) TYPE: nucleic acid (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:140:

CCTTGTGGGA AAAAAGGGAG 20

(2) INFORMATION FOR SEQ ID NO:141:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:141:

CAAGTGTGTT CTGCCTTCAC A 21

(2) INFORMATION FOR SEQ ID NO:142:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:142:

CACAAGGGCA CAGCTAGACA 20

(2) INFORMATION FOR SEQ ID NO:143:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:143:

TCAGCTGTAT AAATGTCTGC CG 22

(2) INFORMATION FOR SEQ ID NO:144:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide ( i i i ) HYPOTHETICAL: NO ( i v ) ANTI-SENSE: NO ( x i ) SEQUENCE DESCRIPTION: SEQ ID NO:144:

GGTCAGAATG CCTGGACTGT 20

( 2 ) INFORMATION FOR SEQ ID NO:145:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:145:

TATTTGTCTT TCCATGCCTG G 21

( 2 ) INFORMATION FOR SEQ ID NO:146:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:146:

TTTACTAAGC CTGAGAGGCA GC 22

( 2 ) INFORMATION FOR SEQ ID NO:147:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:147:

CTAACACAGG AACAGCAAGC C 21

( 2 ) INFORMATION FOR SEQ ID NO:148:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:148:

ATGTGCAGAG TGTGCAGGTT 20

( 2 ) INFORMATION FOR SEQ ID NO:149:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:149:

AGCTTTTTTG ATGTTTGCTG G 21

( 2 ) INFORMATION FOR SEQ ID NO:150:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:150:

GCAACTGCAA CAAAAGCAAA 20

( 2 ) INFORMATION FOR SEQ ID NO:151:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:151:

ACAGTGCCTG CCAAAGATG 19

( 2 ) INFORMATION FOR SEQ ID NO:152:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:152:

AATTTGAGGT TTTTGTTAGG GC 22

( 2 ) INFORMATION FOR SEQ ID NO:153:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:153:

GCGTGAAGGC TGGATTCTAG    20

( 2 ) INFORMATION FOR SEQ ID NO:154:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:154:

AACAAGAGTT TCCTCCAAGG C    21

( 2 ) INFORMATION FOR SEQ ID NO:155:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:155:

ATGAGCATGT TTTTCTGCTA CA    22

( 2 ) INFORMATION FOR SEQ ID NO:156:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:156:

AGCCAACCAA CAGTTAAATT GA    22

( 2 ) INFORMATION FOR SEQ ID NO:157:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:157:

TGCACGTGAG ATGAGTCTCC 20

( 2 ) INFORMATION FOR SEQ ID NO:158:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:158:

CCACTGCAAA AACACGCTAA 20

( 2 ) INFORMATION FOR SEQ ID NO:159:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:159:

TTTGTTGTTT AAGTCACCCC G 21

( 2 ) INFORMATION FOR SEQ ID NO:160:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:160:

CCCCTGATCT CAGACTTCCA 20

( 2 ) INFORMATION FOR SEQ ID NO:161:

( i ) SEQUENCE CHARACTERISTICS:
  ( A ) LENGTH: 21 base pairs
  ( B ) TYPE: nucleic acid
  ( C ) STRANDEDNESS: single (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:161:

GAGAACCCCT GTGTTACCTC C                                                                                      21

(2) INFORMATION FOR SEQ ID NO:162:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:162:

AAAACCACAA TGCCATGACA                                                                                        20

(2) INFORMATION FOR SEQ ID NO:163:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:163:

AGCCTCCCTC ATCATTTGG                                                                                         19

(2) INFORMATION FOR SEQ ID NO:164:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:164:

ACTGGTTTTG CACATGTAGC C                                                                                      21

(2) INFORMATION FOR SEQ ID NO:165:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Oligonucleotide ( i i i ) HYPOTHETICAL: NO ( i v ) ANTI-SENSE: NO ( x i ) SEQUENCE DESCRIPTION: SEQ ID NO:165:

AGAGGTACCC TGCTTAGGAT TC 22

( 2 ) INFORMATION FOR SEQ ID NO:166:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:166:

TCATTCCTCA CTCTCAATGC A 21

( 2 ) INFORMATION FOR SEQ ID NO:167:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:167:

TGTCGGCTCC AGGTTTTC 18

( 2 ) INFORMATION FOR SEQ ID NO:168:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:168:

CCCTAGCAAG CAGACACACA 20

( 2 ) INFORMATION FOR SEQ ID NO:169:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:169:

CTTTTTATTT CCCCAAATGG C 21

( 2 ) INFORMATION FOR SEQ ID NO:170:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:170:

CTGAGGCCTC CTTGTACTGC 20

( 2 ) INFORMATION FOR SEQ ID NO:171:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:171:

GCTAATATTT TGAGTCAATT TTCCTC 26

( 2 ) INFORMATION FOR SEQ ID NO:172:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:172:

CAAAAACTAT GCTAAAGCCT GTATATG 27

( 2 ) INFORMATION FOR SEQ ID NO:173:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:173:

GGTGGCTCTG ACCTCACATT 20

(2) INFORMATION FOR SEQ ID NO:174:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:174:

ATCCTAGCCA CCCTAGCCAT     20

(2) INFORMATION FOR SEQ ID NO:175:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:175:

GGCATCTTGG CCTGTTTG     18

(2) INFORMATION FOR SEQ ID NO:176:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:176:

GCCTGGGAAC AAAAACAAAA     20

(2) INFORMATION FOR SEQ ID NO:177:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:177:

GAGGAGCCAG AATGGAACAC     20

(2) INFORMATION FOR SEQ ID NO:178:

(i) SEQUENCE CHARACTERISTICS:

( A ) LENGTH: 18 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:178:

ATTGCTAGTG TCGGGGCC                                                                    1 8

( 2 ) INFORMATION FOR SEQ ID NO:179:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:179:

GAGATGAAAA AGATCTGGAC CA                                                               2 2

( 2 ) INFORMATION FOR SEQ ID NO:180:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:180:

CATCCCTCCT GACCACACTT                                                                  2 0

( 2 ) INFORMATION FOR SEQ ID NO:181:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:181:

AGCACCCTGA ACCCTTCC                                                                    1 8

( 2 ) INFORMATION FOR SEQ ID NO:182:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:182:

GAATAGCACT GTTTTGAAGG GG 22

(2) INFORMATION FOR SEQ ID NO:183:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:183:

AGAGTGGTTG GGGAAGGC 18

(2) INFORMATION FOR SEQ ID NO:184:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:184:

GAGTCCTGTC CTCCTTGCTG 20

(2) INFORMATION FOR SEQ ID NO:185:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:185:

CACCATGGGT ATCCAGTGC 19

(2) INFORMATION FOR SEQ ID NO:186:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO ( i v ) ANTI-SENSE: NO ( x i ) SEQUENCE DESCRIPTION: SEQ ID NO:186:

ACCAGGCCCT AGAATTCCAG 20

( 2 ) INFORMATION FOR SEQ ID NO:187:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:187:

GCAGTATTTG GCTTTCTGTT CC 22

( 2 ) INFORMATION FOR SEQ ID NO:188:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:188:

AACCTAGGTG CCCATCAGTG 20

( 2 ) INFORMATION FOR SEQ ID NO:189:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:189:

ACGCATTGTA CCCATGTCAA 20

( 2 ) INFORMATION FOR SEQ ID NO:190:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:190:

CTCAAAAGAG CAGCCAAGGT                20

( 2 ) INFORMATION FOR SEQ ID NO:191:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:191:

GATATGGACG TCTGCAAAAC A                21

( 2 ) INFORMATION FOR SEQ ID NO:192:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:192:

TAAGGAAGGA AAGGGAGGGA                20

( 2 ) INFORMATION FOR SEQ ID NO:193:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:193:

TTTGGAGCTG GACAGTGTTG                20

( 2 ) INFORMATION FOR SEQ ID NO:194:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:194:

TTCTCTATTG TGTCCCCTCC C                21

( 2 ) INFORMATION FOR SEQ ID NO:195:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:195:

TGCAATGACG AAGCCTACTG     20

( 2 ) INFORMATION FOR SEQ ID NO:196:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:196:

AAGGCACTTC CCTGCTCC     18

( 2 ) INFORMATION FOR SEQ ID NO:197:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:197:

GGGAAAGAAG GCGCATAAG     19

( 2 ) INFORMATION FOR SEQ ID NO:198:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:198:

AAATTCTCCT GATCGACCTC A     21

( 2 ) INFORMATION FOR SEQ ID NO:199:

( i ) SEQUENCE CHARACTERISTICS:
    ( A ) LENGTH: 19 base pairs (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:199:

TCAGTTCCTT CTTGGCACG    19

(2) INFORMATION FOR SEQ ID NO:200:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:200:

CATGCCACAT TTGCCATTTA    20

(2) INFORMATION FOR SEQ ID NO:201:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:201:

GAACAATATA ACCATGCAAC CC    22

(2) INFORMATION FOR SEQ ID NO:202:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:202:

TCTACACTAC TCCTTTTTCC CG    22

(2) INFORMATION FOR SEQ ID NO:203:

(i) SEQUENCE CHARACTERISTICS:
        (A) LENGTH: 22 base pairs
        (B) TYPE: nucleic acid
        (C) STRANDEDNESS: single
        (D) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:203:

TGAAAGACAA TTAGGTGAAC CC 22

( 2 ) INFORMATION FOR SEQ ID NO:204:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:204:

TTCCTGGGCC ATCTCATC 18

( 2 ) INFORMATION FOR SEQ ID NO:205:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:205:

CCCCCATGAT GAGGTTAGTG 20

( 2 ) INFORMATION FOR SEQ ID NO:206:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:206:

GTGCGTTTTT GGCAGGATAT 20

( 2 ) INFORMATION FOR SEQ ID NO:207:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:207:

AAGGATGGTT CAAGATCCCC 20

( 2 ) INFORMATION FOR SEQ ID NO:208:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:208:

CTGCCCCCCA AGTTACTGTA 20

( 2 ) INFORMATION FOR SEQ ID NO:209:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:209:

GGGAAGGACA CCAAGATAAG C 21

( 2 ) INFORMATION FOR SEQ ID NO:210:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:210:

AATTTGGCTC TGGGATTCCT 20

( 2 ) INFORMATION FOR SEQ ID NO:211:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:211:

AGGTGAACTA CCATGGCCAG 20

(2) INFORMATION FOR SEQ ID NO:212:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:212:

GGGGAGGATG TACTTGCAGA 20

(2) INFORMATION FOR SEQ ID NO:213:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:213:

TTTACTTTGT TGTGATAAGA CAACCC 26

(2) INFORMATION FOR SEQ ID NO:214:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:214:

TGAATAATGT GGACACCAGA GC 22

(2) INFORMATION FOR SEQ ID NO:215:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:215:

ACCATCACCA CCATCCATCT 20

(2) INFORMATION FOR SEQ ID NO:216:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:216:

CAATGGAATA TTGCTTAGCC TT 22

( 2 ) INFORMATION FOR SEQ ID NO:217:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:217:

CCTTAGAAGC CAAAGCTCCC 20

( 2 ) INFORMATION FOR SEQ ID NO:218:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:218:

CATTATCGTG AGGCTGAAAG C 21

( 2 ) INFORMATION FOR SEQ ID NO:219:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:219:

TGCCCCAAGC TCTACACTG 19

( 2 ) INFORMATION FOR SEQ ID NO:220:

( i ) SEQUENCE CHARACTERISTICS:
  ( A ) LENGTH: 20 base pairs
  ( B ) TYPE: nucleic acid ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:220:

GGTGTCGAGA TGCAGCTGTA 20

( 2 ) INFORMATION FOR SEQ ID NO:221:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:221:

CCACAGAGTG CATCATCCAT 20

( 2 ) INFORMATION FOR SEQ ID NO:222:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:222:

TCAGTGTTGT AAGTGGTGGG G 21

( 2 ) INFORMATION FOR SEQ ID NO:223:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:223:

AGGCAAGTCT CCCATTTTTG 20

( 2 ) INFORMATION FOR SEQ ID NO:224:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:224:

TGCGCTAAAT GGAAACACTG 20

( 2 ) INFORMATION FOR SEQ ID NO:225:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:225:

TCTTCATGCA AGCCAAACAG 20

( 2 ) INFORMATION FOR SEQ ID NO:226:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:226:

CAGCCAGCAA TTGTGTGG 18

( 2 ) INFORMATION FOR SEQ ID NO:227:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:227:

TTGGTGCAAA AGTAATTGCG 20

( 2 ) INFORMATION FOR SEQ ID NO:228:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO (xi) SEQUENCE DESCRIPTION: SEQ ID NO:228:

GAAGAAATGC ACACAAATCC C    21

(2) INFORMATION FOR SEQ ID NO:229:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:229:

AAACAGAAAA CCAAACACTG CA    22

(2) INFORMATION FOR SEQ ID NO:230:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:230:

TGAGATTAAT GTGCAGCATG TG    22

(2) INFORMATION FOR SEQ ID NO:231:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:231:

GAGCATGCTT GGAGTCAACA    20

(2) INFORMATION FOR SEQ ID NO:232:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:232:

TAAGGGCCTG ATCATCTTGG    20

( 2 ) INFORMATION FOR SEQ ID NO:233:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:233:

CCTGCATCCA TCCTTCAAGT         20

( 2 ) INFORMATION FOR SEQ ID NO:234:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:234:

AGGTGCAGAA GCTGGTGAGT         20

( 2 ) INFORMATION FOR SEQ ID NO:235:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:235:

AATTCACACA TTCGAATTGA AA         22

( 2 ) INFORMATION FOR SEQ ID NO:236:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:236:

AGGAGATCGA CAATGCAGGT         20

( 2 ) INFORMATION FOR SEQ ID NO:237:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:237:

CCTCTGCCTT TCCCATGTTA 20

( 2 ) INFORMATION FOR SEQ ID NO:238:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:238:

CCTATGTTAA ACCCCTGGCA 20

( 2 ) INFORMATION FOR SEQ ID NO:239:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:239:

AACAGCAAAA AACTAAAGCA ATCC 24

( 2 ) INFORMATION FOR SEQ ID NO:240:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:240:

GCGCTTTTAA CTACAGGTAC ATTT 24

( 2 ) INFORMATION FOR SEQ ID NO:241:

( i ) SEQUENCE CHARACTERISTICS:
  ( A ) LENGTH: 22 base pairs
  ( B ) TYPE: nucleic acid
  ( C ) STRANDEDNESS: single ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:241:

TTGGATTGAA AGAAGTTGGT CT 22

( 2 ) INFORMATION FOR SEQ ID NO:242:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:242:

AAAGTCACAA GGACAATTTT GC 22

( 2 ) INFORMATION FOR SEQ ID NO:243:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:243:

TTATCAGCAG CATGAAAACA GA 22

( 2 ) INFORMATION FOR SEQ ID NO:244:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:244:

CATGGACCTT CAGCATGATG 20

( 2 ) INFORMATION FOR SEQ ID NO:245:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: Oligonucleotide (iii) HYPOTHETICAL: NO (iv) ANTI-SENSE: NO (xi) SEQUENCE DESCRIPTION: SEQ ID NO:245:

GAGATGAGAA AATCAAGGCT GG 22

(2) INFORMATION FOR SEQ ID NO:246:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:246:

GCACTCGGGT TGTTTCCATA 20

(2) INFORMATION FOR SEQ ID NO:247:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:247:

CCACCACCAC ACTCCCAGT 19

(2) INFORMATION FOR SEQ ID NO:248:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:248:

GTCAGTTGCA GACACTTAGC C 21

(2) INFORMATION FOR SEQ ID NO:249:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO ( x i ) SEQUENCE DESCRIPTION: SEQ ID NO:249:

TTATGGGCTG TACTAAAGCG TT 22

( 2 ) INFORMATION FOR SEQ ID NO:250:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:250:

TAGACACCAT GCTTTATGCT GC 22

( 2 ) INFORMATION FOR SEQ ID NO:251:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:251:

CCCTATCATT GGCAGCTTGT 20

( 2 ) INFORMATION FOR SEQ ID NO:252:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:252:

ATAAAAGCAG CATCTTTTTC GC 22

( 2 ) INFORMATION FOR SEQ ID NO:253:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:253:

CCTTTCCAGC TCACCTTCTG 20

( 2 ) INFORMATION FOR SEQ ID NO:254:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:254:

ACCCTGGCAG TGTCTAGGG      19

( 2 ) INFORMATION FOR SEQ ID NO:255:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:255:

CCTTTTCACG TCCCTGACTC      20

( 2 ) INFORMATION FOR SEQ ID NO:256:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:256:

AAATGAAGAA AATACCCAGA CTGG      24

( 2 ) INFORMATION FOR SEQ ID NO:257:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:257:

AGCAAGACTC TGTCTCGAAA AA      22

( 2 ) INFORMATION FOR SEQ ID NO:258:

( i ) SEQUENCE CHARACTERISTICS:

( A ) LENGTH: 22 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:258:

AAAGTGCAAA TAAGTAAGCC CA                                                                    22

( 2 ) INFORMATION FOR SEQ ID NO:259:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:259:

ATGTAGGAAC TGGGGCAGTG                                                                       20

( 2 ) INFORMATION FOR SEQ ID NO:260:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:260:

TGAAAGCAGT GAGTTTACGG G                                                                     21

( 2 ) INFORMATION FOR SEQ ID NO:261:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:261:

TCTCTCATTT CAGCAGCATC A                                                                     21

( 2 ) INFORMATION FOR SEQ ID NO:262:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:262:

TGGTTCTTCT CCTTTGGCC 19

( 2 ) INFORMATION FOR SEQ ID NO:263:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:263:

TCCCGCAGAC TGTCTCTTG 19

( 2 ) INFORMATION FOR SEQ ID NO:264:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:264:

AGAGCTAGGC TGGGAGCAG 19

( 2 ) INFORMATION FOR SEQ ID NO:265:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:265:

TTGAAGACCC CCAGAGAAGA 20

( 2 ) INFORMATION FOR SEQ ID NO:266:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:266:

CTAGAAGCAA GAGGGAGTCA GC 22

( 2 ) INFORMATION FOR SEQ ID NO:267:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:267:

GAATGCTCTC TGCTATGGAT TG 22

( 2 ) INFORMATION FOR SEQ ID NO:268:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:268:

TAACATGGTG GAAGGCATCA 20

( 2 ) INFORMATION FOR SEQ ID NO:269:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:269:

TGGTTTTTGT ACCAGAACAG AA 22

( 2 ) INFORMATION FOR SEQ ID NO:270:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:270:

TGGTGGCAGG CACCTGTA 18

(2) INFORMATION FOR SEQ ID NO:271:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:271:

ATGAAACTAA AAGTTTGTTT GAAAAGA 27

(2) INFORMATION FOR SEQ ID NO:272:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:272:

TCCTCTAGAT TTTCTCTTCT ACTGGC 26

(2) INFORMATION FOR SEQ ID NO:273:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:273:

GCAAATCCCT GATTTACAGA GG 22

(2) INFORMATION FOR SEQ ID NO:274:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:274:

AATTTTTTGG GGGAAACTGG 20

( 2 ) INFORMATION FOR SEQ ID NO:275:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:275:

TCTATAACCC TGCCCACAGG             20

( 2 ) INFORMATION FOR SEQ ID NO:276:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:276:

AATGTGCTGG GAAGACAGCT             20

( 2 ) INFORMATION FOR SEQ ID NO:277:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:277:

ACATAATGTG TGCCCATGGA             20

( 2 ) INFORMATION FOR SEQ ID NO:278:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:278:

ACGTAGTGAT GAAGCCTGGG             20

( 2 ) INFORMATION FOR SEQ ID NO:279:

( i ) SEQUENCE CHARACTERISTICS:
    ( A ) LENGTH: 20 base pairs (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:279:

GGTTCATTTC AGTGCCCTGT 20

(2) INFORMATION FOR SEQ ID NO:280:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:280:

CAGACAAGGA CGGCCTCTAC 20

(2) INFORMATION FOR SEQ ID NO:281:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:281:

CCTCTTAGGC TTATTGTGGG A 21

(2) INFORMATION FOR SEQ ID NO:282:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:282:

TTCACTCTGT TGTGCTACCA AA 22

(2) INFORMATION FOR SEQ ID NO:283:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:283:

ATGAATTAGG CATTGGGCTG                                                    20

(2) INFORMATION FOR SEQ ID NO:284:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:284:

CCAGTGGAGG GCAGAGTAAA                                                    20

(2) INFORMATION FOR SEQ ID NO:285:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:285:

TGGAAAATTT ACTTGATTCC CAA                                                23

(2) INFORMATION FOR SEQ ID NO:286:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:286:

TAACACATTA TTTCTCTTTC ACGATATG                                           28

(2) INFORMATION FOR SEQ ID NO:287:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (iv) ANTI-SENSE: NO (xi) SEQUENCE DESCRIPTION: SEQ ID NO:287:

CAAGACCCTG TCTCAAAAAA GC   22

(2) INFORMATION FOR SEQ ID NO:288:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:288:

AAAAAAAAAA TGTTGGTGGG G   21

(2) INFORMATION FOR SEQ ID NO:289:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:289:

TCGCCTTCAG CTATGCTAAA   20

(2) INFORMATION FOR SEQ ID NO:290:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:290:

AGCTGCTGGC AAAAACAAAT   20

(2) INFORMATION FOR SEQ ID NO:291:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:291:

TCCTTTGGAA ATTTTTTGCG 20

(2) INFORMATION FOR SEQ ID NO:292:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:292:

AGTAGAGATG GGATTGGGCC 20

(2) INFORMATION FOR SEQ ID NO:293:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:293:

AGCAAAAGCA GTTTTGAGAA GG 22

(2) INFORMATION FOR SEQ ID NO:294:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:294:

TTTCAAAAAA CCAGCTTTTC A 21

(2) INFORMATION FOR SEQ ID NO:295:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:295:

CTGTGCTTTC ATGTTCATTG C 21

(2) INFORMATION FOR SEQ ID NO:296:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:296:

ATTCACGTTG TTGTAGGTGA CA    22

( 2 ) INFORMATION FOR SEQ ID NO:297:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:297:

TCCTCCCCAA AACCCTTAAC    20

( 2 ) INFORMATION FOR SEQ ID NO:298:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:298:

ATTATGTCTC TGTCAGCTCC CC    22

( 2 ) INFORMATION FOR SEQ ID NO:299:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:299:

CTGCCAAGAT TTCAGAGGAT G    21

( 2 ) INFORMATION FOR SEQ ID NO:300:

( i ) SEQUENCE CHARACTERISTICS:
        ( A ) LENGTH: 18 base pairs
        ( B ) TYPE: nucleic acid ( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:300:

GCTCCACTAG GCAGTGCC 18

( 2 ) INFORMATION FOR SEQ ID NO:301:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:301:

TGAGACTTGC CCTCTACATC A 21

( 2 ) INFORMATION FOR SEQ ID NO:302:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:302:

TTCAGGCATT CACATTCTGC 20

( 2 ) INFORMATION FOR SEQ ID NO:303:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:303:

GGATTGCCAG GTGAATGC 18

( 2 ) INFORMATION FOR SEQ ID NO:304:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:304:

ATAATTTCCA TGGCCCCTTC 20

( 2 ) INFORMATION FOR SEQ ID NO:305:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:305:

CACGCCATTG TCAAAAACC 19

( 2 ) INFORMATION FOR SEQ ID NO:306:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:306:

ACAGCTAAAG CAACGTTTTG C 21

( 2 ) INFORMATION FOR SEQ ID NO:307:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:307:

ACTAGTATCG GGCAGCCAGA 20

( 2 ) INFORMATION FOR SEQ ID NO:308:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:308:

TCGCACCTAC AAAGAGCCTT 20

( 2 ) INFORMATION FOR SEQ ID NO:309:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:309:

GAGTCCAGAT TTGAAGAGCA GG 22

( 2 ) INFORMATION FOR SEQ ID NO:310:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:310:

TGATTTGAGG AATAGAATGG CA 22

( 2 ) INFORMATION FOR SEQ ID NO:311:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:311:

GCACTTGGGA GCCATCAG 18

( 2 ) INFORMATION FOR SEQ ID NO:312:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:312:

GGAGGGAAAT AGTGGGGGTA 20

( 2 ) INFORMATION FOR SEQ ID NO:313:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:313:

GAGGTGGTGG GCACCTGTA         19

( 2 ) INFORMATION FOR SEQ ID NO:314:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:314:

AGAGGGGAGG AACACACCTT         20

( 2 ) INFORMATION FOR SEQ ID NO:315:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:315:

AAATCTAGGC ATCATGGCTC A         21

( 2 ) INFORMATION FOR SEQ ID NO:316:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:316:

GCTTCCATGG CAGGAAGAT         19

( 2 ) INFORMATION FOR SEQ ID NO:317:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:317:

TGGTAGGTAC TGCTCCTGGG 20

( 2 ) INFORMATION FOR SEQ ID NO:318:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:318:

GAGAATTGCG CAGCCTAATC 20

( 2 ) INFORMATION FOR SEQ ID NO:319:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:319:

TGGGCTCTTT ATTCTGTTCC A 21

( 2 ) INFORMATION FOR SEQ ID NO:320:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:320:

ATACTGCCCA AAGCAGTGTA CA 22

( 2 ) INFORMATION FOR SEQ ID NO:321:

( i ) SEQUENCE CHARACTERISTICS:
  ( A ) LENGTH: 26 base pairs
  ( B ) TYPE: nucleic acid
  ( C ) STRANDEDNESS: single ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:321:

GGAATCACTG AGTTAGAAGG AATAGG 26

( 2 ) INFORMATION FOR SEQ ID NO:322:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:322:

TTTGTAGCAC TCTATCCTCA AAACC 25

( 2 ) INFORMATION FOR SEQ ID NO:323:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:323:

CCAAACGCAA TTAGAAATCA G 21

( 2 ) INFORMATION FOR SEQ ID NO:324:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:324:

CACTGTTCCC AGCCTGTTTC 20

( 2 ) INFORMATION FOR SEQ ID NO:325:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide -continued (iii) HYPOTHETICAL: NO (iv) ANTI-SENSE: NO (xi) SEQUENCE DESCRIPTION: SEQ ID NO:325:

ACTAAATGAG CAAAGCCCCA 20

(2) INFORMATION FOR SEQ ID NO:326:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:326:

AGAATCAAAG CTTTTCCCTC TG 22

(2) INFORMATION FOR SEQ ID NO:327:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:327:

AACTTGTGTC ACAGGGGTTT G 21

(2) INFORMATION FOR SEQ ID NO:328:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:328:

AATGCATGGA CACAGAGGG 19

(2) INFORMATION FOR SEQ ID NO:329:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO ( x i ) SEQUENCE DESCRIPTION: SEQ ID NO:329:

ACAAAGCTTC ACATAGAAGC CC  22

(2) INFORMATION FOR SEQ ID NO:330:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:330:

TTTCTGAAAA CAGTTGCCAC C  21

(2) INFORMATION FOR SEQ ID NO:331:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:331:

ATGAAGGGCG TAGTCCCC  18

(2) INFORMATION FOR SEQ ID NO:332:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:332:

TGGCCTGGTC CCTTTAGAG  19

(2) INFORMATION FOR SEQ ID NO:333:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:333:

AAGAGGACGA CCATGTGAGG  20

( 2 ) INFORMATION FOR SEQ ID NO:334:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:334:

TTTTTGTGAC TGGCCCTTTC     20

( 2 ) INFORMATION FOR SEQ ID NO:335:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:335:

CCTTGTATTC AGTGCCTGAG G     21

( 2 ) INFORMATION FOR SEQ ID NO:336:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:336:

AGTGGACACT TCCCAGGATG     20

( 2 ) INFORMATION FOR SEQ ID NO:337:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:337:

ACTCATTCAT GGAACCCCAA     20

( 2 ) INFORMATION FOR SEQ ID NO:338:

( i ) SEQUENCE CHARACTERISTICS:

(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:338:

CATCATGCTA GGCACTGACT G 21

(2) INFORMATION FOR SEQ ID NO:339:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:339:

GTTTCCTGCA ACTTCATTTT CC 22

(2) INFORMATION FOR SEQ ID NO:340:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:340:

CTGGGCAACC TGATAAATCT G 21

(2) INFORMATION FOR SEQ ID NO:341:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:341:

TAAAACAAGA GCAAACCAAA CG 22

(2) INFORMATION FOR SEQ ID NO:342:

(i) SEQUENCE CHARACTERISTICS:
(A) LENGTH: 20 base pairs
(B) TYPE: nucleic acid
(C) STRANDEDNESS: single
(D) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:342:

GTTCAATCTT GGGAGGCTGT 20

( 2 ) INFORMATION FOR SEQ ID NO:343:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:343:

ATTTTAACCT CACTGTGCCT CA 22

( 2 ) INFORMATION FOR SEQ ID NO:344:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:344:

TTCAGAGAGT GCTGGCCAC 19

( 2 ) INFORMATION FOR SEQ ID NO:345:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:345:

ACAGTGTTGA ATCGGGATTT G 21

( 2 ) INFORMATION FOR SEQ ID NO:346:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:346:

CTGTGGCTAT GTTCTAAGGA GC 22

( 2 ) INFORMATION FOR SEQ ID NO:347:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:347:

TCATTAGCAT TTTTATGTGC GG 22

( 2 ) INFORMATION FOR SEQ ID NO:348:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:348:

TGGATAAAAT GGAAAATGCT CA 22

( 2 ) INFORMATION FOR SEQ ID NO:349:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:349:

GACAGTGGAG GCAATGTATT TT 22

( 2 ) INFORMATION FOR SEQ ID NO:350:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:350:

```
       GAAAGAGACT TTATCTTGGG CC                                                              22
```

( 2 ) INFORMATION FOR SEQ ID NO:351:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:351:

```
       AAGTCAGGGA GCTTTTTGAG C                                                               21
```

( 2 ) INFORMATION FOR SEQ ID NO:352:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:352:

```
       ATAAATGCCC TTGATTAGGT GC                                                              22
```

( 2 ) INFORMATION FOR SEQ ID NO:353:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:353:

```
       CCTGAGGCTG AGTTAGGCTG                                                                 20
```

( 2 ) INFORMATION FOR SEQ ID NO:354:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:354:

```
       TCCAGATGGG AAAACTGAGC                                                                 20
```

( 2 ) INFORMATION FOR SEQ ID NO:355:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:355:

GAAAAAGATA AACCCAACGT GA    22

( 2 ) INFORMATION FOR SEQ ID NO:356:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:356:

ACGGCACACA TTTTTTAGCC    20

( 2 ) INFORMATION FOR SEQ ID NO:357:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:357:

GTGACTCAGT GATTTGAGGT GC    22

( 2 ) INFORMATION FOR SEQ ID NO:358:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:358:

TGGAGTGGAG TGAAGTGAAG G    21

( 2 ) INFORMATION FOR SEQ ID NO:359:

( i ) SEQUENCE CHARACTERISTICS:
        ( A ) LENGTH: 20 base pairs ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:359:

CCATGATTCC AAAACAACCC                                                                                        20

( 2 ) INFORMATION FOR SEQ ID NO:360:

( i ) SEQUENCE CHARACTERISTICS:
             ( A ) LENGTH: 20 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:360:

CCCTCTCTCC TTACCTGCAA                                                                                        20

( 2 ) INFORMATION FOR SEQ ID NO:361:

( i ) SEQUENCE CHARACTERISTICS:
             ( A ) LENGTH: 20 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:361:

AAATATCACT GCCAGGCCAA                                                                                        20

( 2 ) INFORMATION FOR SEQ ID NO:362:

( i ) SEQUENCE CHARACTERISTICS:
             ( A ) LENGTH: 22 base pairs
             ( B ) TYPE: nucleic acid
             ( C ) STRANDEDNESS: single
             ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:362:

AAACTGCAAT TACTTTTGCA CC                                                                                     22

( 2 ) INFORMATION FOR SEQ ID NO:363:

( i ) SEQUENCE CHARACTERISTICS:
             ( A ) LENGTH: 21 base pairs
             ( B ) TYPE: nucleic acid
             ( C ) STRANDEDNESS: single
             ( D ) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:363:

TGCTTGGCAA AATGTATATG G 21

(2) INFORMATION FOR SEQ ID NO:364:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:364:

AAATATGCCC AGGATTTTCT TT 22

(2) INFORMATION FOR SEQ ID NO:365:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:365:

AAGGAGCAGA GTTGTGGGCT 20

(2) INFORMATION FOR SEQ ID NO:366:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:366:

AGTCAGATGA AGAGCAACCC A 21

(2) INFORMATION FOR SEQ ID NO:367:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO ( i v ) ANTI-SENSE: NO ( x i ) SEQUENCE DESCRIPTION: SEQ ID NO:367:

CTACATGACC TGGCTGCCTT 20

( 2 ) INFORMATION FOR SEQ ID NO:368:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:368:

TGATTGGCAA TGGCAGAATA 20

( 2 ) INFORMATION FOR SEQ ID NO:369:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:369:

CAGAGGCACT ACACTCTCAT TG 22

( 2 ) INFORMATION FOR SEQ ID NO:370:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:370:

CAAGTGCAAC AGTTTGAGAA CC 22

( 2 ) INFORMATION FOR SEQ ID NO:371:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:371:

CCGCTGACTT AAATAAATCC TG 22

(2) INFORMATION FOR SEQ ID NO:372:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:372:

AGTTTTGGTA ACATGCTGTG G 21

(2) INFORMATION FOR SEQ ID NO:373:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:373:

TTGTTCAACT ATTACTGACA CTACTGC 27

(2) INFORMATION FOR SEQ ID NO:374:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:374:

CAGGCTGATG CATACTTACT TGT 23

(2) INFORMATION FOR SEQ ID NO:375:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:375:

ACATGAGCCA CCATGCCT 18

(2) INFORMATION FOR SEQ ID NO:376:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:376:

CCTTGCCAAA TCTGCTCAAC 20

(2) INFORMATION FOR SEQ ID NO:377:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:377:

GGGGGATGCA TTCTGACTAA 20

(2) INFORMATION FOR SEQ ID NO:378:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:378:

CAAGAGAACG GCTTTTGGAG 20

(2) INFORMATION FOR SEQ ID NO:379:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:379:

GTCCTGCCCT TCATTACTGC 20

(2) INFORMATION FOR SEQ ID NO:380:

(i) SEQUENCE CHARACTERISTICS:
  (A) LENGTH: 22 base pairs
  (B) TYPE: nucleic acid (C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:380:

CATGCTGGAC ACTACTCTGA CC 22

(2) INFORMATION FOR SEQ ID NO:381:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:381:

AGAAACTCAC GTATGCCAAG G 21

(2) INFORMATION FOR SEQ ID NO:382:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:382:

TTTAGTGCTT TGACACATTT GC 22

(2) INFORMATION FOR SEQ ID NO:383:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:383:

GTGTTCTTAA AGGGGTCTGG C 21

(2) INFORMATION FOR SEQ ID NO:384:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: Oligonucleotide (i i i) HYPOTHETICAL: NO (i v) ANTI-SENSE: NO (x i) SEQUENCE DESCRIPTION: SEQ ID NO:384:

CATGCATTCT TCCTGTCGG    19

(2) INFORMATION FOR SEQ ID NO:385:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:385:

ATACGCCATG GTTGCCTAAG    20

(2) INFORMATION FOR SEQ ID NO:386:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:386:

TGACAATATC AAGTGTGGCC A    21

(2) INFORMATION FOR SEQ ID NO:387:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:387:

GGAAGGAGTA TTACACTGAG AACT    24

(2) INFORMATION FOR SEQ ID NO:388:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO -continued (xi) SEQUENCE DESCRIPTION: SEQ ID NO:388:

TAATGTGTTT TAGCTGGAAG GGA 23

(2) INFORMATION FOR SEQ ID NO:389:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:389:

CAGCAGAAAT CTCTGTGACA CC 22

(2) INFORMATION FOR SEQ ID NO:390:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:390:

TATTGTGAGA CAGGTCTGGG G 21

(2) INFORMATION FOR SEQ ID NO:391:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:391:

TTTAGGAATC AAATCTGATG GC 22

(2) INFORMATION FOR SEQ ID NO:392:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:392:

AGGGTGGATT GCTGAACTTG 20

( 2 ) INFORMATION FOR SEQ ID NO:393:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:393:

TCCTTCTCAA GTCTCTGCTT CC                                                                    22

( 2 ) INFORMATION FOR SEQ ID NO:394:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:394:

GCAAGCCATA TCTAGCATTT TT                                                                    22

( 2 ) INFORMATION FOR SEQ ID NO:395:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:395:

AGCAGTGGCC TAAACCATTG                                                                       20

( 2 ) INFORMATION FOR SEQ ID NO:396:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:396:

CACACTGTGG ACTGGATTGG                                                                       20

( 2 ) INFORMATION FOR SEQ ID NO:397:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:397:

AGACTGCCTT TCCCTGGC 18

( 2 ) INFORMATION FOR SEQ ID NO:398:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:398:

AGGAAATTGG AGGCTGGTTT 20

( 2 ) INFORMATION FOR SEQ ID NO:399:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:399:

AAAAGGTCCT GGCATACAGC 20

( 2 ) INFORMATION FOR SEQ ID NO:400:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:400:

AACTAATTGG TCAGGCCACG 20

( 2 ) INFORMATION FOR SEQ ID NO:401:

( i ) SEQUENCE CHARACTERISTICS:
    ( A ) LENGTH: 21 base pairs
    ( B ) TYPE: nucleic acid
    ( C ) STRANDEDNESS: single (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:401:

CCCAATTGTC TCCCTAAATC C　　　　　　　　　　　　21

(2) INFORMATION FOR SEQ ID NO:402:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:402:

AATCTGCATG GTCAAAGATG G　　　　　　　　　　　　21

(2) INFORMATION FOR SEQ ID NO:403:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:403:

CATTGTTGGC ACAGAGATGG　　　　　　　　　　　　　20

(2) INFORMATION FOR SEQ ID NO:404:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:404:

CACTTCCACA TTTGCAAATC A　　　　　　　　　　　　21

(2) INFORMATION FOR SEQ ID NO:405:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Oligonucleotide (  i i i ) HYPOTHETICAL: NO (  i v ) ANTI-SENSE: NO (  x i ) SEQUENCE DESCRIPTION: SEQ ID NO:405:

GACAGAGCAG CAAACTCAAG G 21

( 2 ) INFORMATION FOR SEQ ID NO:406:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:406:

TCTGACTCCT TCCTGTCTAG GG 22

( 2 ) INFORMATION FOR SEQ ID NO:407:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:407:

CTTCCCATTG AAACCCTTAG G 21

( 2 ) INFORMATION FOR SEQ ID NO:408:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:408:

GCTCTATTCC TATCCGTTTC CC 22

( 2 ) INFORMATION FOR SEQ ID NO:409:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO (x i) SEQUENCE DESCRIPTION: SEQ ID NO:409:

TCAGGTCTCA TGATATTGGG C 21

(2) INFORMATION FOR SEQ ID NO:410:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:410:

TTAGCTGGCT GTCTGTCTTA CC 22

(2) INFORMATION FOR SEQ ID NO:411:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:411:

GTGAGGGCAT TTCCCTCTAA 20

(2) INFORMATION FOR SEQ ID NO:412:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:412:

CCAGGCCCTT CATCCATC 18

(2) INFORMATION FOR SEQ ID NO:413:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:413:

CCTGGGTTAA AACACTCAAT TG 22

( 2 ) INFORMATION FOR SEQ ID NO:414:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:414:

AGGAAGCTGA TTTTCTCCTG C               21

( 2 ) INFORMATION FOR SEQ ID NO:415:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:415:

CTCACAACCC TCCATGGC               18

( 2 ) INFORMATION FOR SEQ ID NO:416:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:416:

ACTAAACCAC CAGGGCAGG               19

( 2 ) INFORMATION FOR SEQ ID NO:417:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:417:

AAGTAAAGCC GCAAAAGCAA               20

( 2 ) INFORMATION FOR SEQ ID NO:418:

( i ) SEQUENCE CHARACTERISTICS:

( A ) LENGTH: 22 base pairs
                    ( B ) TYPE: nucleic acid
                    ( C ) STRANDEDNESS: single
                    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:418:

GCTTAAACTA TTTTGGGGGA CT                                                    2 2

( 2 ) INFORMATION FOR SEQ ID NO:419:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:419:

ATACCTCAGG GACCTGCATG                                                       2 0

( 2 ) INFORMATION FOR SEQ ID NO:420:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:420:

CAGAACTGGT GAGCAACAGC                                                       2 0

( 2 ) INFORMATION FOR SEQ ID NO:421:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:421:

GCAGGATGAA ATGCACCC                                                         1 8

( 2 ) INFORMATION FOR SEQ ID NO:422:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear (  i i  ) MOLECULE TYPE: Oligonucleotide (  i i i  ) HYPOTHETICAL: NO (  i v  ) ANTI-SENSE: NO (  x i  ) SEQUENCE DESCRIPTION: SEQ ID NO:422:

TGAGGGGTCA CCAGCAAT 18

( 2 ) INFORMATION FOR SEQ ID NO:423:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i  ) MOLECULE TYPE: Oligonucleotide (  i i i  ) HYPOTHETICAL: NO (  i v  ) ANTI-SENSE: NO (  x i  ) SEQUENCE DESCRIPTION: SEQ ID NO:423:

CACTGGAGGA AAAAGCCAAC 20

( 2 ) INFORMATION FOR SEQ ID NO:424:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i  ) MOLECULE TYPE: Oligonucleotide (  i i i  ) HYPOTHETICAL: NO (  i v  ) ANTI-SENSE: NO (  x i  ) SEQUENCE DESCRIPTION: SEQ ID NO:424:

AAGCCCATAC CCTCTTCTCA 20

( 2 ) INFORMATION FOR SEQ ID NO:425:

(  i  ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (  i i  ) MOLECULE TYPE: Oligonucleotide (  i i i  ) HYPOTHETICAL: NO (  i v  ) ANTI-SENSE: NO (  x i  ) SEQUENCE DESCRIPTION: SEQ ID NO:425:

GGTTGGGGTG GGAGAGAG 18

( 2 ) INFORMATION FOR SEQ ID NO:426:

(  i  ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (  i i  ) MOLECULE TYPE: Oligonucleotide (  i i i  ) HYPOTHETICAL: NO ( i v ) ANTI-SENSE: NO ( x i ) SEQUENCE DESCRIPTION: SEQ ID NO:426:

TTCAGGTGAT GAAAATGTGA CA 22

( 2 ) INFORMATION FOR SEQ ID NO:427:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:427:

AAATGACAGT GGAGGCCACT 20

( 2 ) INFORMATION FOR SEQ ID NO:428:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:428:

GACAGGCCTT GGAAATGAAA 20

( 2 ) INFORMATION FOR SEQ ID NO:429:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:429:

GTTCCTTTTA GCTTCAGTGC TT 22

( 2 ) INFORMATION FOR SEQ ID NO:430:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:430:

```
     AGCAATCAAT GCAATGAAAC C                                                            21
```

(2) INFORMATION FOR SEQ ID NO:431:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:431:

```
     CCGGCCTCCT TTGCTACT                                                                18
```

(2) INFORMATION FOR SEQ ID NO:432:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:432:

```
     AGGTCCAGAA GAGGAGATGT TG                                                           22
```

(2) INFORMATION FOR SEQ ID NO:433:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:433:

```
     TTTTTCAGAC CATTTTATTT GAATG                                                        25
```

(2) INFORMATION FOR SEQ ID NO:434:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:434:

```
     GAAATTTATA CTACCCATGG GGC                                                          23
```

-continued ( 2 ) INFORMATION FOR SEQ ID NO:435:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:435:

GGGGGGTCTT CATTACCTTT     20

( 2 ) INFORMATION FOR SEQ ID NO:436:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:436:

AGCTGACTGG ACTCACTTTG G     21

( 2 ) INFORMATION FOR SEQ ID NO:437:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:437:

CTCACCTGCC CTCTGCAC     18

( 2 ) INFORMATION FOR SEQ ID NO:438:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:438:

CTACCTGGAG GGAGGGACTC     20

( 2 ) INFORMATION FOR SEQ ID NO:439:

( i ) SEQUENCE CHARACTERISTICS:
        ( A ) LENGTH: 22 base pairs (B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:439:

GGGGTTAAAT ACCACACAAT GG 22

(2) INFORMATION FOR SEQ ID NO:440:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:440:

TGAGGGGAGT GTTAAGGCAC 20

(2) INFORMATION FOR SEQ ID NO:441:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:441:

ACCTGCACAT CCTGCACAT 19

(2) INFORMATION FOR SEQ ID NO:442:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:442:

GCCATCTATT CCTGGAGAGA G 21

(2) INFORMATION FOR SEQ ID NO:443:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:443:

ACAAAAAATG GCAAGTAGAC CA 22

(2) INFORMATION FOR SEQ ID NO:444:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:444:

AACAACTCTG GAGGGGTGG 19

(2) INFORMATION FOR SEQ ID NO:445:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:445:

TCGATGACCA GCCAACAATA 20

(2) INFORMATION FOR SEQ ID NO:446:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:446:

CCATGGGTCC AAGCAGAC 18

(2) INFORMATION FOR SEQ ID NO:447:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO -continued (iv) ANTI-SENSE: NO (xi) SEQUENCE DESCRIPTION: SEQ ID NO:447:

AAACCTGCCC AGGCCTAC           18

(2) INFORMATION FOR SEQ ID NO:448:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:448:

TGTGTTATGG GCCATGGTC           19

(2) INFORMATION FOR SEQ ID NO:449:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:449:

CCAAAAACCA GTACATCATC CA           22

(2) INFORMATION FOR SEQ ID NO:450:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:450:

CCACCAAATC CATGTTTTGA           20

(2) INFORMATION FOR SEQ ID NO:451:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:451:

TTTAGACCCA CAAAAAGCAG TT                                                                                          22

(2) INFORMATION FOR SEQ ID NO:452:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:452:

AAACTGCAAA CTTGGAAAGT TG                                                                                          22

(2) INFORMATION FOR SEQ ID NO:453:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:453:

GGTGTAAGAG CTCCCTGCTG                                                                                             20

(2) INFORMATION FOR SEQ ID NO:454:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:454:

GAGAGTCTGG ACCAATCCCA                                                                                             20

(2) INFORMATION FOR SEQ ID NO:455:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:455:

TGAAGCAAAA CAGGGAATCC                                                                                             20

(2) INFORMATION FOR SEQ ID NO:456:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:456:

TTTTTGGGCA TGTCTGATCA 20

( 2 ) INFORMATION FOR SEQ ID NO:457:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:457:

ATCCAAGGTC CCTGATAAAC TT 22

( 2 ) INFORMATION FOR SEQ ID NO:458:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:458:

GGAAAGGAAA AAGGGAAAAC T 21

( 2 ) INFORMATION FOR SEQ ID NO:459:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:459:

ACTCCTAGCC ACCCCAATCT 20

( 2 ) INFORMATION FOR SEQ ID NO:460:

( i ) SEQUENCE CHARACTERISTICS:
    ( A ) LENGTH: 20 base pairs
    ( B ) TYPE: nucleic acid (C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:460:

TACTGCGGTA GCTGCATGAC 20

(2) INFORMATION FOR SEQ ID NO:461:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:461:

CAGTGATTGC AACCTTGCAC 20

(2) INFORMATION FOR SEQ ID NO:462:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:462:

GGAGAGGAGA AAGGGTTGCT 20

(2) INFORMATION FOR SEQ ID NO:463:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:463:

CGCCTGCCAG TAGTTGAAGT 20

(2) INFORMATION FOR SEQ ID NO:464:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:464:

GATGCCGTCC AAATCTGG  18

(2) INFORMATION FOR SEQ ID NO:465:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:465:

CGAGCACTCT TTCAGTCTCA A  21

(2) INFORMATION FOR SEQ ID NO:466:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:466:

TCAGCATGCA TTTATCGAGC  20

(2) INFORMATION FOR SEQ ID NO:467:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:467:

TAGGCTCAAA TCAACCAAGT CA  22

(2) INFORMATION FOR SEQ ID NO:468:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO ( x i ) SEQUENCE DESCRIPTION: SEQ ID NO:468:

AGATGGGGTC TCACTGTTGC 20

( 2 ) INFORMATION FOR SEQ ID NO:469:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:469:

CCTCTGCCAA CAATCTGGTT 20

( 2 ) INFORMATION FOR SEQ ID NO:470:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:470:

AGTAGAAGCA TAGCATTTGC CA 22

( 2 ) INFORMATION FOR SEQ ID NO:471:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:471:

GTGTTTTTTG AGACAGTCTC GCT 23

( 2 ) INFORMATION FOR SEQ ID NO:472:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:472:

CCTCAGAAGT TTGCTGGTTA AGA 23

( 2 ) INFORMATION FOR SEQ ID NO:473:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:473:

ACTGCTTCTG ACAGCAATTG A 21

( 2 ) INFORMATION FOR SEQ ID NO:474:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:474:

TTCCCAGGTC AAATATTGGT G 21

( 2 ) INFORMATION FOR SEQ ID NO:475:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:475:

GCATCTGTGC AGTCTTCTGC 20

( 2 ) INFORMATION FOR SEQ ID NO:476:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:476:

TAGTGGGCAG TCAGTGCTTG 20

( 2 ) INFORMATION FOR SEQ ID NO:477:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:477:

TGGCTGCTCT GCTTTTTACC 20

(2) INFORMATION FOR SEQ ID NO:478:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:478:

AAGTGTGCAC TACCTTGTCA CC 22

(2) INFORMATION FOR SEQ ID NO:479:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:479:

CTGGATGGCC AGAGAGAAAC 20

(2) INFORMATION FOR SEQ ID NO:480:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:480:

ATACCCTCAG TGCCCAACAG 20

(2) INFORMATION FOR SEQ ID NO:481:

(i) SEQUENCE CHARACTERISTICS:
(A) LENGTH: 21 base pairs
(B) TYPE: nucleic acid
(C) STRANDEDNESS: single (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:481:

CTCAAGCTCT GGTGACTTTG G    21

(2) INFORMATION FOR SEQ ID NO:482:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:482:

GGAATGCTAC TGGAGAGATT CA    22

(2) INFORMATION FOR SEQ ID NO:483:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:483:

TAACAGAGCA GTCTATGGCA CC    22

(2) INFORMATION FOR SEQ ID NO:484:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:484:

AATCTGTAAA GTCAGCATCC CC    22

(2) INFORMATION FOR SEQ ID NO:485:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Oligonucleotide (i i i) HYPOTHETICAL: NO (i v) ANTI-SENSE: NO (x i) SEQUENCE DESCRIPTION: SEQ ID NO:485:

CAAGAACATG GCAATTAAGC C 21

(2) INFORMATION FOR SEQ ID NO:486:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:486:

CACCACGTAA CCTCAGCAGA 20

(2) INFORMATION FOR SEQ ID NO:487:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:487:

GGCAACCAAG AGGGAAAGTT 20

(2) INFORMATION FOR SEQ ID NO:488:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:488:

AGAAGTGCTC TGTCCTCTGA CA 22

(2) INFORMATION FOR SEQ ID NO:489:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO ( x i ) SEQUENCE DESCRIPTION: SEQ ID NO:489:

AGACATTGGC CTGGTTCTTG                                                                  20

( 2 ) INFORMATION FOR SEQ ID NO:490:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:490:

CCCAGTGCCA GGCTTGTC                                                                    18

( 2 ) INFORMATION FOR SEQ ID NO:491:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:491:

CCCATTCAGT TCAAGCTTCT C                                                                21

( 2 ) INFORMATION FOR SEQ ID NO:492:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:492:

CCTGGACATA ACCCCATTGT                                                                  20

( 2 ) INFORMATION FOR SEQ ID NO:493:

( i ) SEQUENCE CHARACTERISTICS:
       ( A ) LENGTH: 21 base pairs
       ( B ) TYPE: nucleic acid
       ( C ) STRANDEDNESS: single
       ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:493:

CCCTATTACT CAGGACCCAC C                                                                21

( 2 ) INFORMATION FOR SEQ ID NO:494:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:494:

CACTGCTTTA TCCCGCCTAG    20

( 2 ) INFORMATION FOR SEQ ID NO:495:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:495:

GAGCTCAGGC TAACCTGTGG    20

( 2 ) INFORMATION FOR SEQ ID NO:496:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:496:

GTATCAGTTA GCTTTTGCTG CC    22

( 2 ) INFORMATION FOR SEQ ID NO:497:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:497:

GCACAGACTC CCTTGGACAT    20

( 2 ) INFORMATION FOR SEQ ID NO:498:

( i ) SEQUENCE CHARACTERISTICS:

(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:498:

GTTCCCCTGT AAGGAATGAG C                              21

(2) INFORMATION FOR SEQ ID NO:499:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:499:

GTGCATATTG AACCAGATGG GCGGG                          25

(2) INFORMATION FOR SEQ ID NO:500:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:500:

TGGACCTGCT TGGTACAAGG ACCGA                          25

(2) INFORMATION FOR SEQ ID NO:501:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:501:

GCACCAGTCC TGGCCTAGAA GATTGTGGTC                     30

(2) INFORMATION FOR SEQ ID NO:502:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:502:

TAGCTGGATC TGAAAGCTGC AGGGGCTC 28

(2) INFORMATION FOR SEQ ID NO:503:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:503:

GGCCGTGTTA AAGCTGGAAG ATGTGAG 27

(2) INFORMATION FOR SEQ ID NO:504:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:504:

ATGATTGGTT ATGCTGATTA TCTGTTCCAA 30

(2) INFORMATION FOR SEQ ID NO:505:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:505:

GTGTAGTACA AAGGCAGAGT G 21

(2) INFORMATION FOR SEQ ID NO:506:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO ( i v ) ANTI-SENSE: NO ( x i ) SEQUENCE DESCRIPTION: SEQ ID NO:506:

CTAGGGAGAG GTGCCATTCA A 21

( 2 ) INFORMATION FOR SEQ ID NO:507:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:507:

ACTCGATGAA GGTTCCATGG GTGGA 25

( 2 ) INFORMATION FOR SEQ ID NO:508:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:508:

TCTGTGCCCA TAGAAGGGAC CTAGG 25

( 2 ) INFORMATION FOR SEQ ID NO:509:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:509:

GCCTGGACTA GGCAAATGGT CTCTCATTCC 30

( 2 ) INFORMATION FOR SEQ ID NO:510:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:510:

TGGGATTGTC AAGAGTGGAC CATGAGGATC 30

(2) INFORMATION FOR SEQ ID NO:511:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:511:

CCTCCTCATA GTGCTGCTCC 20

(2) INFORMATION FOR SEQ ID NO:512:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:512:

GATAGAAGTG CAAGGTGGAT CC 22

(2) INFORMATION FOR SEQ ID NO:513:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:513:

CTTGCTTGTT TTGACTCAGG C 21

(2) INFORMATION FOR SEQ ID NO:514:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:514:

AGAGAAAGAG TTGGAGCAGG G 21

( 2 ) INFORMATION FOR SEQ ID NO:515:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:515:

CTGGACTACG TGGCCTTCTC     20

( 2 ) INFORMATION FOR SEQ ID NO:516:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:516:

TTCAGAAGCA CTTGGCTGG     19

( 2 ) INFORMATION FOR SEQ ID NO:517:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:517:

TGCCAGATGT TGACATTAAA GG     22

( 2 ) INFORMATION FOR SEQ ID NO:518:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:518:

GCAGCTTCAC ATCCACTTCA     20

( 2 ) INFORMATION FOR SEQ ID NO:519:

( i ) SEQUENCE CHARACTERISTICS:
        ( A ) LENGTH: 20 base pairs (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:519:

TGAATGGGCG GAGTTATGAT 20

(2) INFORMATION FOR SEQ ID NO:520:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:520:

TATCAGGTTC ACTTCCGGGA 20

(2) INFORMATION FOR SEQ ID NO:521:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:521:

CACCCGGGAG ACCTGCAAGC 20

(2) INFORMATION FOR SEQ ID NO:522:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:522:

TCTAAGCAGC CAGCTCTTGC A 21

(2) INFORMATION FOR SEQ ID NO:523:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:523:

GCTAATCACA GTCTAACCGA 20

(2) INFORMATION FOR SEQ ID NO:524:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:524:

TTGCACTGTC TTGGATGCA 19

(2) INFORMATION FOR SEQ ID NO:525:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:525:

CAGGCCACTG CTGTTCCT 18

(2) INFORMATION FOR SEQ ID NO:526:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:526:

ACCTTGTCCT CGGATGTTTG 20

(2) INFORMATION FOR SEQ ID NO:527:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:527:

ATCCTGGAGG TTTCCAGCTT 20

(2) INFORMATION FOR SEQ ID NO:528:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:528:

TGTCCAACAA ATGACCTGGA 20

(2) INFORMATION FOR SEQ ID NO:529:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:529:

CTCAGGCACA GTGGAACTGA 20

(2) INFORMATION FOR SEQ ID NO:530:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:530:

GTCCCAGAGA CATTCTATTC CG 22

(2) INFORMATION FOR SEQ ID NO:531:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:531:

```
AGAGGGACCA CTACCCGACT                                                        20
```

(2) INFORMATION FOR SEQ ID NO:532:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:532:

```
AGCACCGCAG CTCAGTTC                                                          18
```

(2) INFORMATION FOR SEQ ID NO:533:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:533:

```
CTTCCCCTCC ACAGGTCTC                                                         19
```

(2) INFORMATION FOR SEQ ID NO:534:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:534:

```
CTGGAGCTCT GTCTCCTGCT                                                        20
```

(2) INFORMATION FOR SEQ ID NO:535:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:535:

```
AAACAGAATG CGATTCACAC C                                                      21
```

(2) INFORMATION FOR SEQ ID NO:536:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:536:

ATTAAGCCAT GACGGTGCTC 20

( 2 ) INFORMATION FOR SEQ ID NO:537:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:537:

CAGGCTGTGT CCCTCTTCTC 20

( 2 ) INFORMATION FOR SEQ ID NO:538:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:538:

CAGAAGCTAT TCCAATCATC CC 22

( 2 ) INFORMATION FOR SEQ ID NO:539:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:539:

CAGCAGGGAT CTATGCACCC ATCTG 25

( 2 ) INFORMATION FOR SEQ ID NO:540:

( i ) SEQUENCE CHARACTERISTICS:
( A ) LENGTH: 25 base pairs
( B ) TYPE: nucleic acid (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:540:

TCTGGCATAT CCCTGTGGAG CCTTT 25

(2) INFORMATION FOR SEQ ID NO:541:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:541:

AAGGTATTTT GGCCCAGTCA ATCAAAGGT 29

(2) INFORMATION FOR SEQ ID NO:542:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:542:

AGTCATACAC CTTAACCAAG TGGTTTCC 28

(2) INFORMATION FOR SEQ ID NO:543:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:543:

GCAGAATGTG GACATGAAGA 20

(2) INFORMATION FOR SEQ ID NO:544:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (  i i i ) HYPOTHETICAL: NO (  i v ) ANTI-SENSE: NO (  x i ) SEQUENCE DESCRIPTION: SEQ ID NO:544:

ATGCTAAAAA AGATTCGCAA TG 22

( 2 ) INFORMATION FOR SEQ ID NO:545:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:545:

GAGCTCAATC ATCTGCTACG G 21

( 2 ) INFORMATION FOR SEQ ID NO:546:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:546:

TGCCGCTGTA GAACTCCAC 19

( 2 ) INFORMATION FOR SEQ ID NO:547:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:547:

CAGTGACAGG CAACCTGCT 19

( 2 ) INFORMATION FOR SEQ ID NO:548:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:548:

GTGCTCGGTT CTCTGTCTCC 20

( 2 ) INFORMATION FOR SEQ ID NO:549:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:549:

CTCACTCTCT CATCACCCTG C 21

( 2 ) INFORMATION FOR SEQ ID NO:550:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:550:

TAGCGATTGT GGGATGATGA 20

( 2 ) INFORMATION FOR SEQ ID NO:551:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:551:

ACAAGGTCTT ACCCCCAGCT 20

( 2 ) INFORMATION FOR SEQ ID NO:552:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:552:

TTCCACCACA TGTGACTCGT 20

( 2 ) INFORMATION FOR SEQ ID NO:553:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:553:

TTATGACCAT CAGAACCAGC C     21

( 2 ) INFORMATION FOR SEQ ID NO:554:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:554:

CTGTGAGACA CCACACCCC     19

( 2 ) INFORMATION FOR SEQ ID NO:555:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:555:

TAACCCCAGG TACCCATGAA     20

( 2 ) INFORMATION FOR SEQ ID NO:556:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:556:

TCTGTCTTCA CACGGCCTC     19

( 2 ) INFORMATION FOR SEQ ID NO:557:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:557:

GTGAAGCATC AGGGCCTGAA C                                                                 21

( 2 ) INFORMATION FOR SEQ ID NO:558:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:558:

CATTTTCTTG TTGTTAGCAA T                                                                 21

( 2 ) INFORMATION FOR SEQ ID NO:559:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:559:

GGGCTTACCT CCTGCTTCGT GACCTTCCTC                                                        30

( 2 ) INFORMATION FOR SEQ ID NO:560:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:560:

GAGGTCATGA TTGCAGAAGA GGTGACTGGA                                                        30

( 2 ) INFORMATION FOR SEQ ID NO:561:

( i ) SEQUENCE CHARACTERISTICS:
                ( A ) LENGTH: 19 base pairs
                ( B ) TYPE: nucleic acid
                ( C ) STRANDEDNESS: single (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:561:

GGTTTGCACG TTTCCACAC 19

(2) INFORMATION FOR SEQ ID NO:562:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:562:

CTGGTACAGA GTCAGGAATC CC 22

(2) INFORMATION FOR SEQ ID NO:563:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:563:

AGGCAGATAA CTTACAAAAT CCTA 24

(2) INFORMATION FOR SEQ ID NO:564:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:564:

TGCTGGCAAA CTCGTTTCTG TCCT 24

(2) INFORMATION FOR SEQ ID NO:565:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:565:

GACAGACACA GAGGAGAGAA TGAATATAT 29

(2) INFORMATION FOR SEQ ID NO:566:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:566:

CCAGTGCAGC AGAAGCAAAG CGCGG 25

(2) INFORMATION FOR SEQ ID NO:567:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:567:

ACAATTGGAT TACTACTAGC 20

(2) INFORMATION FOR SEQ ID NO:568:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:568:

TGTATTTGTA TCGATTAACC 20

(2) INFORMATION FOR SEQ ID NO:569:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO ( x i ) SEQUENCE DESCRIPTION: SEQ ID NO:569:

GACCTGCGTG TGTTTGTGCT CTGTGT  26

( 2 ) INFORMATION FOR SEQ ID NO:570:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:570:

TTCTTCACTG GAGGTAGAAG CAGCCC  26

( 2 ) INFORMATION FOR SEQ ID NO:571:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:571:

GACGGGCTAA CTGATGTCTA C  21

( 2 ) INFORMATION FOR SEQ ID NO:572:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:572:

ATTAGCCAAG CAGTTGCCAG C  21

( 2 ) INFORMATION FOR SEQ ID NO:573:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:573:

CTCATTTGAA GACTGCAGCA  20

( 2 ) INFORMATION FOR SEQ ID NO:574:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:574:

AGGGCTTCCT GTCCATCTA     19

( 2 ) INFORMATION FOR SEQ ID NO:575:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:575:

AGTTACACCG GTTCTGCAGA     20

( 2 ) INFORMATION FOR SEQ ID NO:576:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:576:

GATTAATGAT AGTGCTATCC     20

( 2 ) INFORMATION FOR SEQ ID NO:577:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:577:

CACAAACATT GGCGCAT     17

( 2 ) INFORMATION FOR SEQ ID NO:578:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:578:

TTCTGGGTCA CGGTGCTTCA 20

(2) INFORMATION FOR SEQ ID NO:579:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:579:

AATGGTGTCC CCACACATGT 20

(2) INFORMATION FOR SEQ ID NO:580:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:580:

TCCTACCTAC CGAGCTTAAA 20

(2) INFORMATION FOR SEQ ID NO:581:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:581:

GCCTAGTCCC TGGGTGTGGT C 21

(2) INFORMATION FOR SEQ ID NO:582:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:582:

GGGGGTCTGG GAACATGTCC CC 22

(2) INFORMATION FOR SEQ ID NO:583:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:583:

ATATGGAAAC TCTCCGTACT 20

(2) INFORMATION FOR SEQ ID NO:584:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:584:

GCAACCATGG AGAGTCTGGA 20

(2) INFORMATION FOR SEQ ID NO:585:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:585:

GTAGTTGTGG GCGAGGGTAA 20

(2) INFORMATION FOR SEQ ID NO:586:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO ( i v ) ANTI-SENSE: NO ( x i ) SEQUENCE DESCRIPTION: SEQ ID NO:586:

AAACAATCCC TCCTCGCC 18

( 2 ) INFORMATION FOR SEQ ID NO:587:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:587:

TAGTATTGCC ATAGAAGAAG C 21

( 2 ) INFORMATION FOR SEQ ID NO:588:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:588:

GCAACACGTA CACACTGAGA CA 22

( 2 ) INFORMATION FOR SEQ ID NO:589:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:589:

CTGAAACCAA GTGAAAAGGA GA 22

( 2 ) INFORMATION FOR SEQ ID NO:590:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:590:

```
      AAGCTCCATT GTCTTCTGGC                                                                  20
```

( 2 ) INFORMATION FOR SEQ ID NO:591:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:591:

```
      TACCATATTA AATCACCCAC ATGG                                                             24
```

( 2 ) INFORMATION FOR SEQ ID NO:592:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:592:

```
      GGAATCAGGA TTCAAACTCT GG                                                               22
```

( 2 ) INFORMATION FOR SEQ ID NO:593:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:593:

```
      GCAACATGGT AAGAGTCCAG C                                                                21
```

( 2 ) INFORMATION FOR SEQ ID NO:594:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:594:

```
      GTAGCTGGGA CCAGAGGGAT                                                                  20
```

( 2 ) INFORMATION FOR SEQ ID NO:595:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:595:

CTTTTTGTTG CCCATTGCTT        20

( 2 ) INFORMATION FOR SEQ ID NO:596:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:596:

GTAAAGGATA AAAACTCTGC AGGC        24

( 2 ) INFORMATION FOR SEQ ID NO:597:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:597:

AGTGATCTCT GAGAAAAGGG        20

( 2 ) INFORMATION FOR SEQ ID NO:598:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:598:

ATATTGTGAA TGACTAGGG        19

( 2 ) INFORMATION FOR SEQ ID NO:599:

( i ) SEQUENCE CHARACTERISTICS:
        ( A ) LENGTH: 20 base pairs (B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:599:

ATTTTGGATG AGCCAAGCCT 20

(2) INFORMATION FOR SEQ ID NO:600:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:600:

ATCTGTATAT ATGTGTACCT G 21

(2) INFORMATION FOR SEQ ID NO:601:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:601:

GATCCTGTCT CAAACACAAA C 21

(2) INFORMATION FOR SEQ ID NO:602:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:602:

AAGTCTTCAG CTTTATCAAC 20

(2) INFORMATION FOR SEQ ID NO:603:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:603:

CCTGGTTTAG AATAATACCT 20

(2) INFORMATION FOR SEQ ID NO:604:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:604:

ATAATGTACT GTGATAAATG CT 22

(2) INFORMATION FOR SEQ ID NO:605:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:605:

GGTTTAAAAA GTCAGCCCTC 20

(2) INFORMATION FOR SEQ ID NO:606:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO (i v) ANTI-SENSE: NO (x i) SEQUENCE DESCRIPTION: SEQ ID NO:606:

AATCATTTTC AAGCATAGGC 20

(2) INFORMATION FOR SEQ ID NO:607:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: Oligonucleotide (i i i) HYPOTHETICAL: NO -continued (iv) ANTI-SENSE: NO (xi) SEQUENCE DESCRIPTION: SEQ ID NO:607:

ACTGTCCTCT CATCCTACTG                                                                      20

(2) INFORMATION FOR SEQ ID NO:608:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:608:

TACAGAGCTG AGTTTGTAGC                                                                      20

(2) INFORMATION FOR SEQ ID NO:609:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:609:

TGGAGATGTG CCATAGAGGT                                                                      20

(2) INFORMATION FOR SEQ ID NO:610:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:610:

TCAGGAAAAC TGCCTGAGG                                                                       19

(2) INFORMATION FOR SEQ ID NO:611:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:611:

| CAACGGAACA GGAGTCCTT | 19 |

(2) INFORMATION FOR SEQ ID NO:612:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:612:

| GCTTCTGAGA CTTCAATCTA | 20 |

(2) INFORMATION FOR SEQ ID NO:613:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:613:

| GTTTGAAGGA AGTGATTTCC | 20 |

(2) INFORMATION FOR SEQ ID NO:614:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:614:

| TAGGGCCACC TCCAGTTCAT | 20 |

(2) INFORMATION FOR SEQ ID NO:615:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:615:

| GAATGTAGCC TCAAAAGGAT GG | 22 |

(2) INFORMATION FOR SEQ ID NO:616:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:616:

CCAGTTCAAT TTAGCCTTCA GG　　　　　　　　　　　　　　　　　　　　　　　　22

( 2 ) INFORMATION FOR SEQ ID NO:617:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:617:

TTTCCGAAGA AGGCAGTTTG　　　　　　　　　　　　　　　　　　　　　　　　20

( 2 ) INFORMATION FOR SEQ ID NO:618:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:618:

ATCAGCCTAG AGGCCTGACT　　　　　　　　　　　　　　　　　　　　　　　　20

( 2 ) INFORMATION FOR SEQ ID NO:619:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:619:

GCTACTACGA TGCCATGGGT　　　　　　　　　　　　　　　　　　　　　　　　20

( 2 ) INFORMATION FOR SEQ ID NO:620:

( i ) SEQUENCE CHARACTERISTICS:
    ( A ) LENGTH: 24 base pairs
    ( B ) TYPE: nucleic acid ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:620:

TTACGATAAT GACATTTCTT CTGG 24

( 2 ) INFORMATION FOR SEQ ID NO:621:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:621:

GATCAGTAAT TAGCCAGACT CTAGG 25

( 2 ) INFORMATION FOR SEQ ID NO:622:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:622:

GGTTTTGGAG CTTAAGGAGG 20

( 2 ) INFORMATION FOR SEQ ID NO:623:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:623:

ACTTCAGCCT CGGTGACAG 19

( 2 ) INFORMATION FOR SEQ ID NO:624:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: Oligonucleotide (iii) HYPOTHETICAL: NO (iv) ANTI-SENSE: NO (xi) SEQUENCE DESCRIPTION: SEQ ID NO:624:

TGTTCTGCCT CTGTTGTTAC 20

(2) INFORMATION FOR SEQ ID NO:625:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:625:

GGCTCTTGTA GTTTCTTATC TCCT 24

(2) INFORMATION FOR SEQ ID NO:626:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:626:

AAGGCGGATG CTGGAC 16

(2) INFORMATION FOR SEQ ID NO:627:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:627:

TTGATTTGGA AGATTTTCAC 20

(2) INFORMATION FOR SEQ ID NO:628:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO ( x i ) SEQUENCE DESCRIPTION: SEQ ID NO:628:

GGGGCAGAAT GGGTAT                                                                     16

( 2 ) INFORMATION FOR SEQ ID NO:629:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:629:

CTCCTTCTGC TGGGAGAGCT TCCTACGGCT                                                       30

( 2 ) INFORMATION FOR SEQ ID NO:630:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:630:

CGAGCCCAGG AGCTGGAGAT GGAGATGGAG                                                       30

( 2 ) INFORMATION FOR SEQ ID NO:631:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:631:

AGCTTATAAG AGGCTGCTGG G                                                                21

( 2 ) INFORMATION FOR SEQ ID NO:632:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:632:

TTTTTTGGAT GGATTTGTTT CC                                                               22

( 2 ) INFORMATION FOR SEQ ID NO:633:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:633:

CTGTTCGAGT GCCTGAAACA     20

( 2 ) INFORMATION FOR SEQ ID NO:634:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:634:

GTATGGCCCT AAACAAGCCA     20

( 2 ) INFORMATION FOR SEQ ID NO:635:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:635:

CAGTGTTGGA ACTGCGGGCT TGAGGCTGGA     30

( 2 ) INFORMATION FOR SEQ ID NO:636:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:636:

AGGAGAATCT CCTTGAACGT GCACTCATCG     30

( 2 ) INFORMATION FOR SEQ ID NO:637:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:637:

AGTCTCCTAG CATCTTGTGA GTTGCAT 27

( 2 ) INFORMATION FOR SEQ ID NO:638:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:638:

GTGGTCAGCT GAGTGCATAC TGTCCAC 27

( 2 ) INFORMATION FOR SEQ ID NO:639:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:639:

CGGCATTTCA TCCAGGAC 18

( 2 ) INFORMATION FOR SEQ ID NO:640:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:640:

GGTGTAGGAG GTGCGACAAT 20

( 2 ) INFORMATION FOR SEQ ID NO:641:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:641:

ATAAGGACCC AGCCAGGC                                                                18

(2) INFORMATION FOR SEQ ID NO:642:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:642:

CATGATGGAG TCCTGGCC                                                                18

(2) INFORMATION FOR SEQ ID NO:643:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:643:

TGCTTCAACA GTGCTTGGAC                                                              20

(2) INFORMATION FOR SEQ ID NO:644:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:644:

GGACAGGTAA ACGTAGGAGG C                                                            21

(2) INFORMATION FOR SEQ ID NO:645:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Oligonucleotide ( i i i ) HYPOTHETICAL: NO ( i v ) ANTI-SENSE: NO ( x i ) SEQUENCE DESCRIPTION: SEQ ID NO:645:

GGGGAAATTC CACAACCC                                                          18

( 2 ) INFORMATION FOR SEQ ID NO:646:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:646:

GTTGAAGAGC AGCTCAACCC                                                        20

( 2 ) INFORMATION FOR SEQ ID NO:647:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:647:

CCTGCAGATC TCCTTCGCTG ACTACAACCT                                             30

( 2 ) INFORMATION FOR SEQ ID NO:648:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:648:

AGAACGCCCT AAGCCCGTCC CAGGAAACAC                                             30

( 2 ) INFORMATION FOR SEQ ID NO:649:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:649:

TTGTCAGTAG AGTGCGCCC 19

(2) INFORMATION FOR SEQ ID NO:650:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:650:

ACCTCCCTCA GGGTCCAG 18

(2) INFORMATION FOR SEQ ID NO:651:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:651:

GGTTGGCCAA TCTACTCCCA GG 22

(2) INFORMATION FOR SEQ ID NO:652:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:652:

GCTCACTCAG TGTGGCAAAG 20

(2) INFORMATION FOR SEQ ID NO:653:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:653:

AGCTCAGCAT GGCTAGGGTA 20

( 2 ) INFORMATION FOR SEQ ID NO:654:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:654:

GTAGCATCAA AGCTCCAGCC 20

( 2 ) INFORMATION FOR SEQ ID NO:655:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:655:

GGGTGCTGAG ACGAGGGACT 20

( 2 ) INFORMATION FOR SEQ ID NO:656:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:656:

GAGACCCTGT AGGAGGACCC 20

( 2 ) INFORMATION FOR SEQ ID NO:657:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:657:

TTCATTTGAG CAGCCAGATG 20

( 2 ) INFORMATION FOR SEQ ID NO:658:

( i ) SEQUENCE CHARACTERISTICS:

(A) LENGTH: 22 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:658:

CCAAAAACCT TTTACAGAAC GA 22

(2) INFORMATION FOR SEQ ID NO:659:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:659:

CCCTCATTTG ATGACCGC 18

(2) INFORMATION FOR SEQ ID NO:660:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:660:

GGGACACAGG AGGACACAGT 20

(2) INFORMATION FOR SEQ ID NO:661:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:661:

ACTGAGGCTT TTGCAAGGAA 20

(2) INFORMATION FOR SEQ ID NO:662:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (  i  i  ) MOLECULE TYPE: Oligonucleotide (  i  i  i  ) HYPOTHETICAL: NO (  i  v  ) ANTI-SENSE: NO (  x  i  ) SEQUENCE DESCRIPTION: SEQ ID NO:662:

CATGCATGAA TGAGCATTCC                                                                                    20

( 2 ) INFORMATION FOR SEQ ID NO:663:

(  i  ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear (  i  i  ) MOLECULE TYPE: Oligonucleotide (  i  i  i  ) HYPOTHETICAL: NO (  i  v  ) ANTI-SENSE: NO (  x  i  ) SEQUENCE DESCRIPTION: SEQ ID NO:663:

CTTGTGGCTG CTCCCAGT                                                                                      18

( 2 ) INFORMATION FOR SEQ ID NO:664:

(  i  ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear (  i  i  ) MOLECULE TYPE: Oligonucleotide (  i  i  i  ) HYPOTHETICAL: NO (  i  v  ) ANTI-SENSE: NO (  x  i  ) SEQUENCE DESCRIPTION: SEQ ID NO:664:

ACATATGGGG GCATGTGG                                                                                      18

( 2 ) INFORMATION FOR SEQ ID NO:665:

(  i  ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear (  i  i  ) MOLECULE TYPE: Oligonucleotide (  i  i  i  ) HYPOTHETICAL: NO (  i  v  ) ANTI-SENSE: NO (  x  i  ) SEQUENCE DESCRIPTION: SEQ ID NO:665:

TAGTGTTCCT TGCATTTTGG G                                                                                  21

( 2 ) INFORMATION FOR SEQ ID NO:666:

(  i  ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear (  i  i  ) MOLECULE TYPE: Oligonucleotide (  i  i  i  ) HYPOTHETICAL: NO ( i v ) ANTI-SENSE: NO ( x i ) SEQUENCE DESCRIPTION: SEQ ID NO:666:

ATCCCAGGAT GTGACTCACT G               21

( 2 ) INFORMATION FOR SEQ ID NO:667:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:667:

ATTGTCACAG CAGGTGCAAG               20

( 2 ) INFORMATION FOR SEQ ID NO:668:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:668:

AGACTCACCT GGATTTGAAA CA               22

( 2 ) INFORMATION FOR SEQ ID NO:669:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:669:

GAAACTGGAG CCTCACGAAG               20

( 2 ) INFORMATION FOR SEQ ID NO:670:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:670:

```
        AACACCCTAT TTGGGGGTTC                                                    20
```

(2) INFORMATION FOR SEQ ID NO:671:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:671:

```
        ACAACTACCA CTGCGATCCC                                                    20
```

(2) INFORMATION FOR SEQ ID NO:672:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:672:

```
        ACTGGTACAC CTCCAGCCC                                                     19
```

(2) INFORMATION FOR SEQ ID NO:673:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:673:

```
        CATTCTCAAC GACAACCCCT                                                    20
```

(2) INFORMATION FOR SEQ ID NO:674:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:674:

```
        GCAAGAGATG TTAGCTGCCC                                                    20
```

( 2 ) INFORMATION FOR SEQ ID NO:675:

( i ) SEQUENCE CHARACTERISTICS:
　　　　　　　　( A ) LENGTH: 18 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:675:

TCGCAGACCT AACCCTGC　　　　　　　　　　　　　　　　　　　　　　　　　　　　18

( 2 ) INFORMATION FOR SEQ ID NO:676:

( i ) SEQUENCE CHARACTERISTICS:
　　　　　　　　( A ) LENGTH: 22 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:676:

CAGAGATAAA TACAGCCCCA GG　　　　　　　　　　　　　　　　　　　　　　　　22

( 2 ) INFORMATION FOR SEQ ID NO:677:

( i ) SEQUENCE CHARACTERISTICS:
　　　　　　　　( A ) LENGTH: 30 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:677:

GGCGCCCGTA GAAGCAAAGC CAGAGTGCCA　　　　　　　　　　　　　　　　　　　　30

( 2 ) INFORMATION FOR SEQ ID NO:678:

( i ) SEQUENCE CHARACTERISTICS:
　　　　　　　　( A ) LENGTH: 30 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:678:

CGTTTCTGAG CTTCCTAGAT TCTTAATTTG　　　　　　　　　　　　　　　　　　　　30

( 2 ) INFORMATION FOR SEQ ID NO:679:

( i ) SEQUENCE CHARACTERISTICS:
　　　　　　　　( A ) LENGTH: 30 base pairs ( B ) TYPE: nucleic acid
          ( C ) STRANDEDNESS: single
          ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:679:

GTACATGCAG CTGATAGCCC TGCCAAGGCC 30

( 2 ) INFORMATION FOR SEQ ID NO:680:

( i ) SEQUENCE CHARACTERISTICS:
          ( A ) LENGTH: 30 base pairs
          ( B ) TYPE: nucleic acid
          ( C ) STRANDEDNESS: single
          ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:680:

GACGTGGACA CAACCGTGGT GCTGACAGGG 30

( 2 ) INFORMATION FOR SEQ ID NO:681:

( i ) SEQUENCE CHARACTERISTICS:
          ( A ) LENGTH: 19 base pairs
          ( B ) TYPE: nucleic acid
          ( C ) STRANDEDNESS: single
          ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:681:

ATCATCTTCC TGGCCTTGG 19

( 2 ) INFORMATION FOR SEQ ID NO:682:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:682:

TACATGTCTC CATAGCCCAG G 21

( 2 ) INFORMATION FOR SEQ ID NO:683:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:683:

ATAGGGGAGA ATACTGGGAG TG 22

( 2 ) INFORMATION FOR SEQ ID NO:684:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:684:

GCACTTGGTA AGAGAGTCAC AA 22

( 2 ) INFORMATION FOR SEQ ID NO:685:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:685:

CAAAGGAAGC GCCATAGAAG 20

( 2 ) INFORMATION FOR SEQ ID NO:686:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:686:

CTGAGGATGG CAACCTGG 18

( 2 ) INFORMATION FOR SEQ ID NO:687:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:687:

CTCAGTGCCA TGAAGATGGA                                                                              20

( 2 ) INFORMATION FOR SEQ ID NO:688:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:688:

CAAGATCACT CGATCTCCAG G                                                                            21

( 2 ) INFORMATION FOR SEQ ID NO:689:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:689:

CTCATCAGAA AGAAGTCCTT CAGGCGCACC                                                                   30

( 2 ) INFORMATION FOR SEQ ID NO:690:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:690:

ATCCAGGTAG TTCTCCAGGG GCTGTTCATC                                                                   30

( 2 ) INFORMATION FOR SEQ ID NO:691:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:691:

TGAGAGAAGT ACCCCTGAGA GC 22

( 2 ) INFORMATION FOR SEQ ID NO:692:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:692:

ACCCCTCTAG TGGATGGTCC 20

( 2 ) INFORMATION FOR SEQ ID NO:693:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:693:

TGGCACACAA CATCCAAACT 20

( 2 ) INFORMATION FOR SEQ ID NO:694:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:694:

CAACGCCTCC TCCTCTAGG 19

( 2 ) INFORMATION FOR SEQ ID NO:695:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:695:

GAAGTACGGG CAGTTCAGTG GCCT 24

( 2 ) INFORMATION FOR SEQ ID NO:696:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:696:

ATACACCAAG GTCCATGTTC CCCGT      25

( 2 ) INFORMATION FOR SEQ ID NO:697:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:697:

TGCTCAACCT GCTGATGAAC      20

( 2 ) INFORMATION FOR SEQ ID NO:698:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:698:

TAGCATTCCA CCACTCTGCA      20

( 2 ) INFORMATION FOR SEQ ID NO:699:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:699:

CTCGTGAAAA CCAACCCAAT      20

( 2 ) INFORMATION FOR SEQ ID NO:700:

( i ) SEQUENCE CHARACTERISTICS:
        ( A ) LENGTH: 20 base pairs
        ( B ) TYPE: nucleic acid ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:700:

TCACATCAGC TTTGTCTGCC 20

( 2 ) INFORMATION FOR SEQ ID NO:701:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:701:

CTCCTCTCCT CCCCTTGC 18

( 2 ) INFORMATION FOR SEQ ID NO:702:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:702:

TCTCATAGTA GTGCTGCTGC G 21

( 2 ) INFORMATION FOR SEQ ID NO:703:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:703:

ATCAGGACAA CTTTGAGAAA ATCA 24

( 2 ) INFORMATION FOR SEQ ID NO:704:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: Oligonucleotide (   i i i   ) HYPOTHETICAL: NO (   i v   ) ANTI-SENSE: NO (   x i   ) SEQUENCE DESCRIPTION: SEQ ID NO:704:

TGGAAACTCT AAATTTCTTG AAATG 25

( 2 ) INFORMATION FOR SEQ ID NO:705:

(   i   ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (   i i   ) MOLECULE TYPE: Oligonucleotide (   i i i   ) HYPOTHETICAL: NO (   i v   ) ANTI-SENSE: NO (   x i   ) SEQUENCE DESCRIPTION: SEQ ID NO:705:

ATCGGGGACC GCTACTTC 18

( 2 ) INFORMATION FOR SEQ ID NO:706:

(   i   ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (   i i   ) MOLECULE TYPE: Oligonucleotide (   i i i   ) HYPOTHETICAL: NO (   i v   ) ANTI-SENSE: NO (   x i   ) SEQUENCE DESCRIPTION: SEQ ID NO:706:

TACCTGAGAT AGTCTCTCCG GC 22

( 2 ) INFORMATION FOR SEQ ID NO:707:

(   i   ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (   i i   ) MOLECULE TYPE: Oligonucleotide (   i i i   ) HYPOTHETICAL: NO (   i v   ) ANTI-SENSE: NO (   x i   ) SEQUENCE DESCRIPTION: SEQ ID NO:707:

CTGTGACACA TCGTTTTGGG 20

( 2 ) INFORMATION FOR SEQ ID NO:708:

(   i   ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (   i i   ) MOLECULE TYPE: Oligonucleotide (   i i i   ) HYPOTHETICAL: NO (   i v   ) ANTI-SENSE: NO ( x i ) SEQUENCE DESCRIPTION: SEQ ID NO:708:

AGCACACAGT GCAAACAAGT G  21

( 2 ) INFORMATION FOR SEQ ID NO:709:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:709:

TTCCTGCTGC TGCTCTCC  18

( 2 ) INFORMATION FOR SEQ ID NO:710:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:710:

TGTCCAAAAT ATACTGGCAG AA  22

( 2 ) INFORMATION FOR SEQ ID NO:711:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:711:

TTGCTTGAGG TGGTAAGGCT  20

( 2 ) INFORMATION FOR SEQ ID NO:712:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:712:

TGCTAAATGG GTGATGAAAC C  21

( 2 ) INFORMATION FOR SEQ ID NO:713:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:713:

CACCTGGGAA TACCAGTGCT         20

( 2 ) INFORMATION FOR SEQ ID NO:714:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:714:

AAGGAACGAA AAGAAGCTTC G         21

( 2 ) INFORMATION FOR SEQ ID NO:715:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:715:

AAGAACCAGT CCCTGGGC         18

( 2 ) INFORMATION FOR SEQ ID NO:716:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:716:

TCGCAGCAGC AGTACAGG         18

( 2 ) INFORMATION FOR SEQ ID NO:717:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:717:

ACCAGTTCCT GTTGGACCTG    20

( 2 ) INFORMATION FOR SEQ ID NO:718:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:718:

CTTCACCTTC TTGACCTCGC    20

( 2 ) INFORMATION FOR SEQ ID NO:719:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:719:

GTGGCATGTT TGGTATGCTG    20

( 2 ) INFORMATION FOR SEQ ID NO:720:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:720:

TGGCAACAGA TTCACAGAGC    20

( 2 ) INFORMATION FOR SEQ ID NO:721:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:721:

TGCCATCTGA ACATGCTCTC                                                        20

(2) INFORMATION FOR SEQ ID NO:722:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:722:

GGTCGGGAAA GTAAGATGAG G                                                      21

(2) INFORMATION FOR SEQ ID NO:723:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:723:

TGTAGAAGGC ACAATATGGG C                                                      21

(2) INFORMATION FOR SEQ ID NO:724:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:724:

GCAAGCTAAG CAGCAGCC                                                          18

(2) INFORMATION FOR SEQ ID NO:725:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Oligonucleotide ( i i i ) HYPOTHETICAL: NO ( i v ) ANTI-SENSE: NO ( x i ) SEQUENCE DESCRIPTION: SEQ ID NO:725:

GGGGGAAGAC AGATATGGGT 20

( 2 ) INFORMATION FOR SEQ ID NO:726:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:726:

CTGTTCAGTG CAATTCAAAA GC 22

( 2 ) INFORMATION FOR SEQ ID NO:727:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:727:

TGGTAGTTAC GTTGTCCGCA 20

( 2 ) INFORMATION FOR SEQ ID NO:728:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:728:

TCTCCTGCTC GTACTGGGAT 20

( 2 ) INFORMATION FOR SEQ ID NO:729:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:729:

CCTGGTCCTG CACTGTCC                                                                                     18

( 2 ) INFORMATION FOR SEQ ID NO:730:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:730:

CAGCAGACAG TGTCAGGGAA                                                                                   20

( 2 ) INFORMATION FOR SEQ ID NO:731:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:731:

GCGTCCATTT GGAGTGAAGT                                                                                   20

( 2 ) INFORMATION FOR SEQ ID NO:732:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:732:

TAGATACTCG GCTTCCTGCT G                                                                                 21

( 2 ) INFORMATION FOR SEQ ID NO:733:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:733:

TTGTTGTGAC TTTGACGCTT G                                                                                 21

( 2 ) INFORMATION FOR SEQ ID NO:734:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:734:

TTAAGGCCTT GGGAAGGG      18

( 2 ) INFORMATION FOR SEQ ID NO:735:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:735:

GTGACTCCAA TTAGCCAGTT CC      22

( 2 ) INFORMATION FOR SEQ ID NO:736:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:736:

TGGGGATGAC ATAGTCTGAG C      21

( 2 ) INFORMATION FOR SEQ ID NO:737:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:737:

TGAAGGCATA CACCATTGTC A      21

( 2 ) INFORMATION FOR SEQ ID NO:738:

( i ) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:738:

AATACACCGA ATCCCAGCAG 20

(2) INFORMATION FOR SEQ ID NO:739:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:739:

TTCCGTATCT CCTCCTGCC 19

(2) INFORMATION FOR SEQ ID NO:740:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:740:

TCCCTCTCT TCCCCAAC 18

(2) INFORMATION FOR SEQ ID NO:741:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:741:

GGTCAAGCTC AGCAACATGA 20

(2) INFORMATION FOR SEQ ID NO:742:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:742:

TGCTTTGTGA CCATCGAGAG 20

( 2 ) INFORMATION FOR SEQ ID NO:743:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:743:

CAGCAGATGG TCAAGCAAAA 20

( 2 ) INFORMATION FOR SEQ ID NO:744:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:744:

ACTCCTGACA CCACCACCTC 20

( 2 ) INFORMATION FOR SEQ ID NO:745:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:745:

TCGCTCACTG ACTCGCTG 18

( 2 ) INFORMATION FOR SEQ ID NO:746:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:746:

AGCCCTCCCG TATCGTAGTT 20

( 2 ) INFORMATION FOR SEQ ID NO:747:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Oligonucleotide ( i i i ) HYPOTHETICAL: NO ( i v ) ANTI-SENSE: NO ( x i ) SEQUENCE DESCRIPTION: SEQ ID NO:747:

CTTGAGAGCC TTCAACCCAG 20

( 2 ) INFORMATION FOR SEQ ID NO:748:

( i ) SEQUENCE CHARACTERISTICS:
        ( A ) LENGTH: 78 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:748:

```
Met Asp Met Phe Gln Lys Val Glu Lys Ile Gly Glu Gly Thr Tyr Gly
 1               5                  10                  15
Val Val Tyr Lys Ala Lys Asn Arg Glu Thr Gly Gln Leu Val Ala Leu
                20                  25                  30
Lys Lys Ile Arg Leu Asp Leu Glu Met Glu Gly Val Pro Ser Thr Ala
            35                  40                  45
Ile Arg Glu Ile Ser Leu Leu Lys Glu Leu Lys His Pro Asn Ile Val
        50                  55                  60
Arg Leu Leu Asp Val Val His Asn Glu Arg Lys Leu Tyr Leu
65                  70                  75
```

( 2 ) INFORMATION FOR SEQ ID NO:749:

( i ) SEQUENCE CHARACTERISTICS:
        ( A ) LENGTH: 78 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:749:

```
Met Glu Asp Tyr Ile Lys Ile Glu Lys Ile Gly Glu Gly Thr Tyr Gly
 1               5                  10                  15
Val Val Tyr Lys Gly Arg His Arg Val Thr Gly Gln Ile Val Ala Met
                20                  25                  30
Lys Lys Ile Arg Leu Glu Ser Glu Glu Glu Gly Val Pro Ser Thr Ala
            35                  40                  45
Ile Arg Glu Ile Ser Leu Leu Lys Glu Leu Arg His Pro Asn Ile Val
        50                  55                  60
```

```
        Ser  Leu  Gln  Asp  Val  Leu  Met  Gln  Asp  Ser  Arg  Leu  Tyr  Leu
         65                  70                   75
```

(2) INFORMATION FOR SEQ ID NO:750:

(i) SEQUENCE CHARACTERISTICS:
        (A) LENGTH: 79 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:750:

```
Met  Met  Glu  Lys  Tyr  Glu  Lys  Ile  Gly  Lys  Ile  Gly  Glu  Gly  Ser  Tyr
 1                   5                   10                              15

Gly  Val  Val  Phe  Lys  Cys  Arg  Asn  Arg  Asp  Thr  Gly  Gln  Ile  Val  Ala
               20                   25                         30

Ile  Lys  Lys  Phe  Leu  Glu  Ser  Glu  Asp  Asp  Pro  Val  Ile  Lys  Lys  Ile
          35                        40                        45

Ala  Leu  Arg  Glu  Ile  Arg  Met  Leu  Lys  Gln  Leu  Lys  His  Pro  Asn  Leu
          50                        55                        60

Val  Asn  Leu  Leu  Glu  Val  Phe  Arg  Arg  Lys  Arg  Leu  His  Leu
 65                  70                   75
```

(2) INFORMATION FOR SEQ ID NO:751:

(i) SEQUENCE CHARACTERISTICS:
        (A) LENGTH: 76 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:751:

```
Met  Tyr  Ile  Lys  Asn  Arg  Ile  Leu  Gly  Arg  Gly  Ala  Tyr  Gly  Ile  Ala
 1                   5                   10                              15

Trp  Leu  Ala  Lys  Asp  Thr  Glu  Thr  Gly  Ala  Ser  Val  Val  Ile  Lys  Glu
               20                   25                         30

Leu  Thr  Leu  Ala  Gln  Leu  Pro  Ala  Ala  Glu  Arg  Glu  Arg  Ala  Leu  Arg
          35                        40                        45

Glu  Ala  Asn  Leu  Leu  Ser  Gln  Leu  Phe  His  Pro  Asn  Ile  Val  Ser  Tyr
          50                        55                        60

Lys  Gln  Ser  Phe  Leu  Glu  Asn  Gly  Ala  Leu  Asn  Ile
 65                  70                   75
```

(2) INFORMATION FOR SEQ ID NO:752:

(i) SEQUENCE CHARACTERISTICS:
        (A) LENGTH: 78 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:752:

```
Met  Glu  Lys  Tyr  Val  Arg  Leu  Gln  Lys  Ile  Gly  Glu  Gly  Ser  Phe  Gly
 1                   5                   10                              15

Lys  Ala  Val  Leu  Val  Lys  Ser  Thr  Glu  Asp  Gly  Arg  His  Tyr  Val  Ile
```

20                              25                              30

Lys  Glu  Ile  Asn  Ile  Ser  Arg  Met  Ser  Asp  Lys  Glu  Arg  Gln  Glu  Ser
                   35                              40                         45

Arg  Arg  Glu  Val  Ala  Val  Leu  Ala  Asn  Met  Lys  His  Pro  Asn  Ile  Val
              50                         55                              60

Gln  Tyr  Lys  Glu  Ser  Phe  Glu  Glu  Asn  Gly  Ser  Leu  Tyr  Ile
    65                        70                             75

( 2 ) INFORMATION FOR SEQ ID NO:753:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:753:

Phe  Gly  Ile  Ile  Arg  Lys  Val  Lys  Arg  Lys  Ser  Asp  Gly  Phe  Ile  Leu
    1                        5                              10                        15

Cys  Arg  Lys  Glu  Ile  Asn  Tyr  Ile  Lys  Met  Ser  Thr  Lys  Glu  Arg  Glu
                   20                              25                         30

Gln  Leu  Thr  Ala  Glu  Phe  Asn  Ile  Leu  Ser  Ser  Leu  Arg  His  Pro  Asn
                   35                              40                         45

Ile  Val  Ala  Tyr  Tyr  His  Arg  Glu  His  Leu  Lys  Ala  Ser  Gln  Asp  Leu
              50                         55                              60

Tyr  Leu  Tyr  Met  Glu  Tyr  Cys  Gly  Gly  Gly  Asp  Leu
    65                        70                             75

( 2 ) INFORMATION FOR SEQ ID NO:754:

( i ) SEQUENCE CHARACTERISTICS:
        ( A ) LENGTH: 76 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:754:

Phe  Gly  Ser  Val  Arg  Lys  Val  Ile  His  Ile  Pro  Thr  Lys  Lys  Leu  Leu
    1                        5                              10                        15

Val  Arg  Lys  Asp  Ile  Lys  Tyr  Gly  His  Met  Asn  Ser  Lys  Glu  Arg  Gln
                   20                              25                         30

Gln  Leu  Ile  Ala  Glu  Cys  Ser  Ile  Leu  Ser  Gln  Leu  Lys  His  Glu  Asn
                   35                              40                         45

Ile  Val  Glu  Phe  Tyr  Asn  Trp  Asp  Phe  Asp  Glu  Gln  Lys  Glu  Val  Leu
              50                         55                              60

Tyr  Leu  Tyr  Met  Glu  Tyr  Cys  Ser  Arg  Gly  Asp  Leu
    65                        70                             75

( 2 ) INFORMATION FOR SEQ ID NO:755:

( i ) SEQUENCE CHARACTERISTICS:
        ( A ) LENGTH: 83 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:755:

| Phe | Gly | Thr | Arg | Gly | Ser | Gly | Thr | Val | Thr | Gly | Pro | Ser | Val | Glx |
|---|---|---|---|---|---|---|---|---|---|---|---|---|---|---|
| 1 | | | | 5 | | | | | 10 | | | | | 15 |

| Trp | Lys | Ser | Arg | Ala | Arg | Leu | Cys | Ser | Gln | Gly | Ser | Gln | Tyr | Tyr | Lys |
|---|---|---|---|---|---|---|---|---|---|---|---|---|---|---|---|
| | | | 20 | | | | | 25 | | | | | 30 | | |

| Tyr | Thr | Gly | Gln | Val | Gln | Ile | Cys | Val | Arg | Asn | Asp | Phe | Ile | Lys | Leu |
|---|---|---|---|---|---|---|---|---|---|---|---|---|---|---|---|
| | | 35 | | | | | 40 | | | | | 45 | | | |

| Cys | Ser | Leu | Ser | His | Lys | Asn | Leu | Val | Lys | Tyr | Tyr | Asp | Val | Tyr | Tyr |
|---|---|---|---|---|---|---|---|---|---|---|---|---|---|---|---|
| | 50 | | | | | 55 | | | | | 60 | | | | |

| Asn | Asp | Thr | Lys | Asn | Leu | Gly | His | Phe | Val | Met | Glu | Tyr | Tyr | Glu | Arg |
|---|---|---|---|---|---|---|---|---|---|---|---|---|---|---|---|
| 65 | | | | | 70 | | | | | 75 | | | | | 80 |

Cys Cys Leu ( 2 ) INFORMATION FOR SEQ ID NO:756:

( i ) SEQUENCE CHARACTERISTICS:
      ( A ) LENGTH: 82 amino acids
      ( B ) TYPE: amino acid
      ( D ) TOPOLOGY: unknown ( i i ) MOLECULE TYPE: protein ( v ) FRAGMENT TYPE: internal ( x i ) SEQUENCE DESCRIPTION: SEQ ID NO:756:

| Ser | Met | Val | Ile | Lys | Asn | Leu | Lys | Arg | Thr | Asn | Lys | Tyr | Ala | Glu | Glu |
|---|---|---|---|---|---|---|---|---|---|---|---|---|---|---|---|
| 1 | | | | 5 | | | | | 10 | | | | | 15 | |

| Asp | Phe | Val | Trp | Arg | Ile | Leu | Ser | Gln | Leu | Val | Thr | Ala | Leu | Tyr | Arg |
|---|---|---|---|---|---|---|---|---|---|---|---|---|---|---|---|
| | | | 20 | | | | | 25 | | | | | 30 | | |

| Cys | His | Tyr | Gly | Thr | Asp | Pro | Ala | Glu | Val | Gly | Ser | Asn | Leu | Leu | Gly |
|---|---|---|---|---|---|---|---|---|---|---|---|---|---|---|---|
| | | 35 | | | | | 40 | | | | | 45 | | | |

| Pro | Ala | Pro | Lys | Pro | Ser | Gly | Leu | Lys | Gly | Lys | Gln | Ala | Gln | Met | Thr |
|---|---|---|---|---|---|---|---|---|---|---|---|---|---|---|---|
| | 50 | | | | | 55 | | | | | 60 | | | | |

| Ile | Leu | His | Arg | Asp | Leu | Lys | Pro | Glu | Asn | Ile | Phe | Leu | Gly | Ser | Asp |
|---|---|---|---|---|---|---|---|---|---|---|---|---|---|---|---|
| 65 | | | | | 70 | | | | | 75 | | | | | 80 |

Asn Thr ( 2 ) INFORMATION FOR SEQ ID NO:757:

( i ) SEQUENCE CHARACTERISTICS:
      ( A ) LENGTH: 76 amino acids
      ( B ) TYPE: amino acid
      ( D ) TOPOLOGY: unknown ( i i ) MOLECULE TYPE: protein ( v ) FRAGMENT TYPE: internal ( x i ) SEQUENCE DESCRIPTION: SEQ ID NO:757:

| Ser | Gln | Met | Ile | Lys | His | Tyr | Lys | Gln | Glu | His | Lys | Tyr | Ile | Pro | Glu |
|---|---|---|---|---|---|---|---|---|---|---|---|---|---|---|---|
| 1 | | | | 5 | | | | | 10 | | | | | 15 | |

| Lys | Ile | Val | Trp | Gly | Ile | Leu | Ala | Gln | Leu | Leu | Thr | Ala | Leu | Tyr | Lys |
|---|---|---|---|---|---|---|---|---|---|---|---|---|---|---|---|
| | | | 20 | | | | | 25 | | | | | 30 | | |

| Cys | His | Tyr | Gly | Val | Glu | Leu | Pro | Thr | Leu | Thr | Thr | Ile | Tyr | Asp | Arg |
|---|---|---|---|---|---|---|---|---|---|---|---|---|---|---|---|
| | | 35 | | | | | 40 | | | | | 45 | | | |

| Met | Lys | Pro | Pro | Val | Lys | Gly | Lys | Asn | Ile | Val | Ile | His | Arg | Asp | Leu |
|---|---|---|---|---|---|---|---|---|---|---|---|---|---|---|---|
| | 50 | | | | | 55 | | | | | 60 | | | | |

| Lys | Pro | Gly | Asn | Ile | Phe | Leu | Ser | Tyr | Asp | Asp | Ser |
|---|---|---|---|---|---|---|---|---|---|---|---|
| 65 | | | | | 70 | | | | | 75 | |

(2) INFORMATION FOR SEQ ID NO:758:

(i) SEQUENCE CHARACTERISTICS:
        (A) LENGTH: 63 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:758:

```
Met Asp Val Ile Leu Phe Tyr Arg Met Lys Glu Arg Val Ile Pro Glu
 1               5                  10                  15

Glu Thr Val Trp Tyr Ile Leu Ser His Leu Ala Glu Ala Leu Leu Tyr
             20                  25                  30

Tyr His Ser Pro Gln Lys Asp Asn Thr Asp Met Gly Pro Leu Val His
         35                  40                  45

Arg Asn Ile Lys Pro Ser Lys Val Phe Leu Ala Ala Asp Gly Tyr
     50                  55                  60
```

(2) INFORMATION FOR SEQ ID NO:759:

(i) SEQUENCE CHARACTERISTICS:
        (A) LENGTH: 60 base pairs
        (B) TYPE: nucleic acid
        (C) STRANDEDNESS: both
        (D) TOPOLOGY: unknown (ii) MOLECULE TYPE: DNA (genomic)

(xi) SEQUENCE DESCRIPTION: SEQ ID NO:759:

CATCTGTNAC TCACCCCTCT GTGTGCTCGT GGTCTGTGAG TGCCTCCACC CAGACAACGC    60

(2) INFORMATION FOR SEQ ID NO:760:

(i) SEQUENCE CHARACTERISTICS:
        (A) LENGTH: 60 base pairs
        (B) TYPE: nucleic acid
        (C) STRANDEDNESS: both
        (D) TOPOLOGY: unknown (ii) MOLECULE TYPE: DNA (genomic)

(xi) SEQUENCE DESCRIPTION: SEQ ID NO:760:

CATCTGTGAC TCACCCCTCT GTGTGCTCGT GGTCTGTGAG TGCCTCCACC CAGACAACGC    60

(2) INFORMATION FOR SEQ ID NO:761:

(i) SEQUENCE CHARACTERISTICS:
        (A) LENGTH: 60 base pairs
        (B) TYPE: nucleic acid
        (C) STRANDEDNESS: both
        (D) TOPOLOGY: unknown (ii) MOLECULE TYPE: DNA (genomic)

(xi) SEQUENCE DESCRIPTION: SEQ ID NO:761:

CTCAGGAGCC GTGCACACCG GGACAGAGAG GATGACCAAG GGGGTCAAGC AGCCCCGCTA    60

(2) INFORMATION FOR SEQ ID NO:762:

(i) SEQUENCE CHARACTERISTICS:
        (A) LENGTH: 34 base pairs
        (B) TYPE: nucleic acid
        (C) STRANDEDNESS: both
        (D) TOPOLOGY: unknown ( i i ) MOLECULE TYPE: DNA (genomic)

( x i ) SEQUENCE DESCRIPTION: SEQ ID NO:762:

CGAGAGATGA GAGTGCACAG CAACCAGCCT GATC 34

( 2 ) INFORMATION FOR SEQ ID NO:763:

( i ) SEQUENCE CHARACTERISTICS:
        ( A ) LENGTH: 26 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:763:

Thr Gly Ser Glu Pro Asn Thr Cys Lys Ala Cys Ser Ala Val Ile Asn
 1               5                  10                  15
Gly Lys Xaa Tyr Cys Ser Gln Cys Asn Ser
            20                  25

( 2 ) INFORMATION FOR SEQ ID NO:764:

( i ) SEQUENCE CHARACTERISTICS:
        ( A ) LENGTH: 26 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:764:

Thr Gly Gln Gly Ser Gly Ala Cys Lys Thr Cys Gly Leu Thr Ile Asp
 1               5                  10                  15
Gly Ala Ser Tyr Cys Ser Glu Cys Asp Thr
            20                  25

( 2 ) INFORMATION FOR SEQ ID NO:765:

( i ) SEQUENCE CHARACTERISTICS:
        ( A ) LENGTH: 26 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:765:

Thr Gly Ser Glu Pro Asn Thr Cys Lys Ala Cys Ser Ala Val Ile Asn
 1               5                  10                  15
Gly Lys Lys Tyr Cys Ser Gln Cys Asn Ser
            20                  25

( 2 ) INFORMATION FOR SEQ ID NO:766:

( i ) SEQUENCE CHARACTERISTICS:
        ( A ) LENGTH: 26 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:766:

```
          Thr  Gly  Thr  Gly  Ala  Gly  Ala  Cys  Lys  Thr  Cys  Gly  Leu  Thr  Ile  Asp
          1                   5                        10                       15

Gly  Ala  Ser  Tyr  Cys  Ser  Glu  Cys  Ala  Thr
                         20                  25
```

( 2 ) INFORMATION FOR SEQ ID NO:767:

( i ) SEQUENCE CHARACTERISTICS:
        ( A ) LENGTH: 65 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:767:

```
          Gln  Ala  Ser  His  Met  Lys  Val  Glu  Ser  Ala  Arg  Pro  His  Leu  Ser  Val
          1                   5                        10                       15

Gln  Thr  His  Ala  Glu  Gly  Leu  Pro  Cys  Gln  Cys  Val  Met  His  Arg  Gln
                              20                  25                       30

Met  Pro  Arg  Arg  Gly  Gly  Leu  Val  Asn  Arg  Ala  Val  Met  Ala  Cys  Val
                         35                       40                  45

Thr  Asp  Ala  Gly  Thr  Met  Phe  Tyr  Ala  Val  Leu  Leu  Ile  Gly  Leu  Met
                    50                       55                       60

Leu
          65
```

( 2 ) INFORMATION FOR SEQ ID NO:768:

( i ) SEQUENCE CHARACTERISTICS:
        ( A ) LENGTH: 68 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:768:

```
          Gly  Ala  Thr  Glu  Gly  Ala  Lys  Lys  Leu  Cys  Lys  Glu  Cys  Thr  Ala  Ala
          1                   5                        10                       15

Asn  Cys  Lys  Thr  Cys  Asp  Asp  Gln  Gly  Gln  Cys  Gln  Ala  Cys  Asn  Asp
                         20                       25                       30

Gly  Phe  Tyr  Lys  Asn  Gly  Asp  Ala  Cys  Ser  Pro  Cys  His  Glu  Ser  Cys
                    35                       40                       45

Lys  Thr  Cys  Ser  Ala  Gly  Thr  Ala  Ser  Asp  Cys  Thr  Glu  Cys  Pro  Thr
                    50                       55                       60

Gly  Lys  Ala  Leu
          65
```

( 2 ) INFORMATION FOR SEQ ID NO:769:

( i ) SEQUENCE CHARACTERISTICS:
        ( A ) LENGTH: 68 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:769:

```
          Gly  Thr  Asn  Ala  Asp  Asn  Lys  Lys  Ala  Cys  Lys  Glu  Cys  Thr  Val  Ala
          1                   5                        10                       15
```

Asn Cys Lys Thr Cys Asn Asp Gln Gly Gln Cys Gln Thr Cys Asn Asp
              20                  25                  30

Gly Phe Tyr Lys Asn Gly Asp Ala Cys Ser Pro Cys His Glu Ser Cys
          35                  40                  45

Lys Thr Cys Ser Ala Gly Thr Ala Ser Asp Cys Thr Glu Cys Pro Thr
      50                  55                  60

Gly Lys Ala Leu
65

(2) INFORMATION FOR SEQ ID NO:770:

(i) SEQUENCE CHARACTERISTICS:
      (A) LENGTH: 65 amino acids
      (B) TYPE: amino acid
      (D) TOPOLOGY: unknown (ii) MOLECULE TYPE: protein (v) FRAGMENT TYPE: internal (xi) SEQUENCE DESCRIPTION: SEQ ID NO:770:

Glu Met Ala Arg Ala Ala Gln Ala Gly Asp Glu Cys Glu Glu Val Thr
 1               5                  10                  15

Gly Ser Glu Pro Asn Thr Cys Lys Ala Cys Ser Ala Val Ile Asn Gly
              20                  25                  30

Lys Lys Tyr Cys Ser Gln Cys Asn Ser Gly Gly Ser Gln Ser Ala Pro
          35                  40                  45

Thr Asp Gly Lys Cys Thr Thr Ala Thr Thr Glu Cys Ser Gln Lys Gln
      50                  55                  60

Asp
65

(2) INFORMATION FOR SEQ ID NO:771:

(i) SEQUENCE CHARACTERISTICS:
      (A) LENGTH: 68 amino acids
      (B) TYPE: amino acid
      (D) TOPOLOGY: unknown (ii) MOLECULE TYPE: protein (v) FRAGMENT TYPE: internal (xi) SEQUENCE DESCRIPTION: SEQ ID NO:771:

Arg Tyr Gly Asp Asp Gly Thr Lys Gly Thr Cys Gly Glu Gly Cys Thr
 1               5                  10                  15

Thr Gly Thr Gly Ala Gly Ala Cys Lys Thr Cys Gly Leu Thr Ile Asp
              20                  25                  30

Gly Ala Ser Tyr Cys Ser Glu Cys Ala Thr Thr Thr Glu Tyr Pro Gln
          35                  40                  45

Asn Gly Val Cys Ala Pro Lys Ala Ser Arg Ala Thr Pro Thr Cys Asn
      50                  55                  60

Asp Ser Pro Ile
65

(2) INFORMATION FOR SEQ ID NO:772:

(i) SEQUENCE CHARACTERISTICS:
      (A) LENGTH: 68 amino acids
      (B) TYPE: amino acid
      (D) TOPOLOGY: unknown (ii) MOLECULE TYPE: protein (v) FRAGMENT TYPE: internal (xi) SEQUENCE DESCRIPTION: SEQ ID NO:772:

| Lys | Tyr | Gly | Asn | Asp | Gly | Thr | Lys | Gly | Thr | Cys | Gly | Glu | Gly | Cys | Thr |
|---|---|---|---|---|---|---|---|---|---|---|---|---|---|---|---|
| 1 | | | | 5 | | | | | 10 | | | | | 15 | |
| Thr | Gly | Gln | Gly | Ser | Gly | Ala | Cys | Lys | Thr | Cys | Gly | Leu | Thr | Ile | Asp |
| | | | 20 | | | | | 25 | | | | | 30 | | |
| Gly | Ala | Ser | Tyr | Cys | Ser | Glu | Cys | Asp | Thr | Gln | Asn | Glu | Tyr | Pro | Gln |
| | | 35 | | | | | 40 | | | | | 45 | | | |
| Asn | Gly | Ile | Cys | Thr | Ser | Thr | Thr | Ala | Arg | Thr | Val | Ala | Thr | Cys | Lys |
| | 50 | | | | | 55 | | | | | | 60 | | | |
| Asn | Ser | Asn | Val | | | | | | | | | | | | |
| 65 | | | | | | | | | | | | | | | |

(2) INFORMATION FOR SEQ ID NO:773:

(i) SEQUENCE CHARACTERISTICS:
        (A) LENGTH: 54 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:773:

| Gly | Asn | Asp | Pro | Xaa | Asp | Gly | Val | Cys | Thr | Ser | Ile | Xaa | Ala | Thr | Ala |
|---|---|---|---|---|---|---|---|---|---|---|---|---|---|---|---|
| 1 | | | | 5 | | | | | 10 | | | | | 15 | |
| Arg | Xaa | Ala | Ser | Xaa | Cys | Lys | Ala | Ser | Gly | Gly | Lys | Xaa | Thr | Glu | Cys |
| | | | 20 | | | | | 25 | | | | | 30 | | |
| Gly | Ala | Asn | Tyr | Ala | Leu | Xaa | Ser | Gly | Gly | Cys | Tyr | Asn | Thr | Gln | Lys |
| | | 35 | | | | | 40 | | | | | 45 | | | |
| Leu | Pro | Gly | Ser | Ser | Xaa | | | | | | | | | | |
| | | 50 | | | | | | | | | | | | | |

(2) INFORMATION FOR SEQ ID NO:774:

(i) SEQUENCE CHARACTERISTICS:
        (A) LENGTH: 54 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:774:

| Gly | Tyr | Ala | Pro | Ile | Asp | Gly | Ile | Cys | Thr | Ala | Val | Ala | Ala | Ala | Gly |
|---|---|---|---|---|---|---|---|---|---|---|---|---|---|---|---|
| 1 | | | | 5 | | | | | 10 | | | | | 15 | |
| Arg | Asp | Val | Ser | Val | Cys | Thr | Ala | Thr | Gly | Gly | Lys | Cys | Thr | Ala | Cys |
| | | | 20 | | | | | 25 | | | | | 30 | | |
| Thr | Gly | Asn | Tyr | Ala | Leu | Leu | Ser | Gly | Gly | Cys | Tyr | Asn | Thr | Gln | Thr |
| | | 35 | | | | | 40 | | | | | 45 | | | |
| Leu | Pro | Gly | Lys | Ser | Val | | | | | | | | | | |
| | | 50 | | | | | | | | | | | | | |

(2) INFORMATION FOR SEQ ID NO:775:

(i) SEQUENCE CHARACTERISTICS:
        (A) LENGTH: 55 amino acids
        (B) TYPE: amino acid
        (D) TOPOLOGY: unknown ( i i ) MOLECULE TYPE: protein ( v ) FRAGMENT TYPE: internal ( x i ) SEQUENCE DESCRIPTION: SEQ ID NO:775:

| Thr | Glu | Tyr | Pro | Gln | Asn | Gly | Val | Cys | Ala | Pro | Lys | Ala | Ser | Arg | Ala |
|---|---|---|---|---|---|---|---|---|---|---|---|---|---|---|---|
| 1 | | | | 5 | | | | | 10 | | | | | 15 | |
| Thr | Pro | Thr | Cys | Asn | Asp | Ser | Pro | Ile | Gln | Asn | Gly | Val | Cys | Gly | Thr |
| | | | 20 | | | | | 25 | | | | | 30 | | |
| Cys | Ala | Asp | Asn | Tyr | Phe | Lys | Met | Asn | Gly | Gly | Cys | Tyr | Glu | Thr | Val |
| | | | 35 | | | | 40 | | | | | 45 | | | |
| Lys | Tyr | Pro | Gly | Lys | Thr | Val | | | | | | | | | |
| | | 50 | | | | 55 | | | | | | | | | |

( 2 ) INFORMATION FOR SEQ ID NO:776:

( i ) SEQUENCE CHARACTERISTICS:
( A ) LENGTH: 51 amino acids
( B ) TYPE: amino acid
( D ) TOPOLOGY: unknown ( i i ) MOLECULE TYPE: protein ( v ) FRAGMENT TYPE: internal ( x i ) SEQUENCE DESCRIPTION: SEQ ID NO:776:

| Cys | Thr | Ala | Ala | Gln | Asn | Lys | Xaa | Xaa | Xaa | Gln | Thr | Xaa | Ala | Asn | Gly |
|---|---|---|---|---|---|---|---|---|---|---|---|---|---|---|---|
| 1 | | | | 5 | | | | | 10 | | | | | 15 | |
| Gln | Ser | Pro | Ala | Gly | Gly | Xaa | Phe | Pro | Ala | Cys | Thr | Xaa | Xaa | Cys | Leu |
| | | | 20 | | | | | 25 | | | | | 30 | | |
| Lys | Xaa | Ala | Xaa | Ser | Lys | Glu | Thr | Cys | Thr | Asp | Cys | Leu | Ala | Gly | Tyr |
| | | | 35 | | | | 40 | | | | | 45 | | | |
| Tyr | Lys | Gly | | | | | | | | | | | | | |
| | | 50 | | | | | | | | | | | | | |

( 2 ) INFORMATION FOR SEQ ID NO:777:

( i ) SEQUENCE CHARACTERISTICS:
( A ) LENGTH: 57 amino acids
( B ) TYPE: amino acid
( D ) TOPOLOGY: unknown ( i i ) MOLECULE TYPE: protein ( v ) FRAGMENT TYPE: internal ( x i ) SEQUENCE DESCRIPTION: SEQ ID NO:777:

| Cys | Lys | Ala | Val | Ala | Asn | Ser | Asn | Asp | Gly | Lys | Cys | Lys | Thr | Cys | Ala |
|---|---|---|---|---|---|---|---|---|---|---|---|---|---|---|---|
| 1 | | | | 5 | | | | | 10 | | | | | 15 | |
| Asn | Gly | Gln | Ala | Pro | Asp | Pro | Ala | Thr | Asn | Phe | Cys | Pro | Leu | Cys | Asp |
| | | | 20 | | | | | 25 | | | | | 30 | | |
| Ser | Thr | Cys | Ala | Glu | Cys | Ser | Thr | Lys | Asn | Asp | Ala | Asp | Ala | Cys | Thr |
| | | | 35 | | | | | 40 | | | | | 45 | | |
| Lys | Cys | Phe | Pro | Gly | Tyr | Tyr | Lys | Thr | | | | | | | |
| | 50 | | | | | 55 | | | | | | | | | |

( 2 ) INFORMATION FOR SEQ ID NO:778:

( i ) SEQUENCE CHARACTERISTICS:
( A ) LENGTH: 50 amino acids
( B ) TYPE: amino acid
( D ) TOPOLOGY: unknown ( i i ) MOLECULE TYPE: protein ( v ) FRAGMENT TYPE: internal ( x i ) SEQUENCE DESCRIPTION: SEQ ID NO:778:

| Cys | Ile | Ser | Ala | Pro | Asn | Gly | Gly | Thr | Cys | Gln | Lys | Ala | Ala | Asp | Gly |
| 1 | | | | 5 | | | | | 10 | | | | | 15 | |

| Tyr | Lys | Leu | Asp | Ser | Gly | Thr | Leu | Thr | Val | Cys | Ser | Glu | Gly | Cys | Lys |
| | | | | 20 | | | | | 25 | | | | | 30 | |

| Glu | Cys | Ala | Ser | Ser | Thr | Asp | Cys | Thr | Thr | Cys | Leu | Asp | Gly | Tyr | Val |
| | | | 35 | | | | | 40 | | | | | 45 | | |

| Lys | Ser |
| | 50 |

( 2 ) INFORMATION FOR SEQ ID NO:779:

( i ) SEQUENCE CHARACTERISTICS:
        ( A ) LENGTH: 20 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:779:

| Lys | Leu | Glu | Asp | Leu | Ile | Val | Lys | Asp | Gly | Leu | Thr | Asp | Val | Tyr | Asn |
| 1 | | | | 5 | | | | | 10 | | | | | 15 | |

| Lys | Ile | His | Met |
| | | | 20 |

( 2 ) INFORMATION FOR SEQ ID NO:780:

( i ) SEQUENCE CHARACTERISTICS:
        ( A ) LENGTH: 70 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:780:

| Ala | Leu | Ile | Gly | Ala | Leu | Leu | Ala | Ile | Cys | Cys | Met | Ile | Phe | Leu | Gly |
| 1 | | | | 5 | | | | | 10 | | | | | 15 | |

| Phe | Ala | Asp | Asp | Val | Leu | Asn | Leu | Arg | Trp | Arg | His | Lys | Leu | Leu | Leu |
| | | | 20 | | | | | 25 | | | | | 30 | | |

| Pro | Thr | Ala | Ala | Ser | Leu | Pro | Leu | Leu | Met | Val | Tyr | Phe | Thr | Asn | Phe |
| | | | 35 | | | | | 40 | | | | | 45 | | |

| Gly | Lys | Thr | Thr | Ile | Val | Val | Pro | Lys | Pro | Phe | Arg | Pro | Ile | Leu | Gly |
| | | 50 | | | | | 55 | | | | | 60 | | | |

| Leu | His | Leu | Asp | Leu | Gly |
| 65 | | | | | 70 |

( 2 ) INFORMATION FOR SEQ ID NO:781:

( i ) SEQUENCE CHARACTERISTICS:
        ( A ) LENGTH: 70 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:781:

| Ala | Leu | Ile | Gly | Ala | Leu | Leu | Ala | Ile | Cys | Cys | Met | Ile | Phe | Leu | Gly |

|     1       |       5       |         10          |          15         |
|-------------|---------------|---------------------|---------------------|

Phe Ala Asp Asp Val Leu Asn Leu Arg Trp Arg His Lys Leu Leu Leu
            20                      25                  30

Pro Thr Ala Ala Ser Leu Pro Leu Leu Met Val Tyr Phe Thr Asn Phe
            35                      40                  45

Gly Asn Ile Thr Ile Val Val Pro Lys Pro Phe Arg Trp Ile Leu Gly
        50                      55                  60

Leu His Leu Asp Leu Gly
65                  70

(2) INFORMATION FOR SEQ ID NO:782:

(i) SEQUENCE CHARACTERISTICS:
        (A) LENGTH: 34 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:782:

Val Asn Gly Val Asp Leu Arg Asn Ala Ser His Glu Gln Ala Ala Ile
1               5                   10                  15

Ala Leu Lys Asn Ala Gly Gln Thr Val Thr Ile Ile Ala Gln Tyr Lys
            20                  25                  30

Pro Glu (2) INFORMATION FOR SEQ ID NO:783:

(i) SEQUENCE CHARACTERISTICS:
        (A) LENGTH: 37 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:783:

Leu Phe Gln Val Asn Gly Ile Asp Leu Arg Gly Ala Ser His Glu Gln
1               5                   10                  15

Ala Ala Ala Ala Leu Lys Gly Ala Gly Gln Thr Val Thr Ile Ile Ala
            20                  25                  30

Gln Tyr Gln Pro Glu
            35

(2) INFORMATION FOR SEQ ID NO:784:

(i) SEQUENCE CHARACTERISTICS:
        (A) LENGTH: 37 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:784:

Leu Leu Ser Val Asn Asn Val Asn Leu Thr His Ala Thr His Glu Glu
1               5                   10                  15

Ala Ala Gln Ala Leu Lys Thr Ser Gly Gly Val Val Thr Leu Leu Ala
            20                  25                  30

Gln Tyr Arg Pro Glu

35

(2) INFORMATION FOR SEQ ID NO:785:

(i) SEQUENCE CHARACTERISTICS:
        (A) LENGTH: 60 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:785:

```
Leu Lys Val His Gln Arg Ile His Thr Gly Glu Lys Pro Tyr Gln Cys
 1               5                  10                  15
Ser Asp Cys Gly Lys Ser Phe Thr His Gly Ser Thr Leu Lys Val His
                20                  25                  30
Gln Arg Ile His Thr Gly Xaa Lys Pro Tyr Asn Cys Asn Val Cys Gly
                35                  40                  45
Lys Cys Phe Met Lys Gly Ser Thr Leu Gln Ala His
                50                  55                  60
```

(2) INFORMATION FOR SEQ ID NO:786:

(i) SEQUENCE CHARACTERISTICS:
        (A) LENGTH: 60 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:786:

```
Leu Thr Asp His Leu Arg Ile His Thr Gly Glu Lys Pro Tyr Lys Cys
 1               5                  10                  15
Asn Glu Cys Gly Lys Thr Phe Arg His Ser Ser Asn Leu Met Gln His
                20                  25                  30
Leu Arg Ser His Thr Gly Glu Lys Pro Tyr Glu Cys Lys Glu Cys Gly
                35                  40                  45
Lys Ser Phe Arg Tyr Asn Ser Ser Leu Thr Glu His
                50                  55                  60
```

(2) INFORMATION FOR SEQ ID NO:787:

(i) SEQUENCE CHARACTERISTICS:
        (A) LENGTH: 60 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:787:

```
Thr Thr Thr Ser Ala Glu His Phe Thr Gly Lys Lys Asn Ser Pro His
 1               5                  10                  15
Glu Gly Lys Arg Ile Trp Trp Lys Asp Asn Lys Asn Lys Thr Trp Glu
                20                  25                  30
Ile Gly Lys Val Ile Thr Trp Gly Arg Gly Phe Ala Cys Phe Ser Ala
                35                  40                  45
Gly Glu Asn Gln Leu Pro Val Trp Xaa Pro Thr Arg
                50                  55                  60
```

(2) INFORMATION FOR SEQ ID NO:788:

(i) SEQUENCE CHARACTERISTICS:
        (A) LENGTH: 60 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:788:

```
Thr Thr Ser Ala Glu Gln His Leu Thr Gly Lys Lys Asn Ser Pro His
 1               5                  10                  15
Glu Gly Lys Leu Ile Trp Trp Lys Asp Asn Lys Asn Lys Thr Trp Glu
                20                  25                  30
Ile Gly Lys Val Ile Thr Trp Gly Arg Gly Phe Ala Cys Val Ser Pro
                35                  40                  45
Gly Glu Asn Gln Leu Pro Val Trp Leu Pro Thr Arg
 50                  55                  60
```

(2) INFORMATION FOR SEQ ID NO:789:

(i) SEQUENCE CHARACTERISTICS:
        (A) LENGTH: 25 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:789:

```
Pro Pro Asp Ile Thr Val Asn Xaa Gly Ser Ser Val Thr Leu Leu Cys
 1               5                  10                  15
Leu Ala Ile Gly Arg Pro Glu Pro Thr
                20                  25
```

(2) INFORMATION FOR SEQ ID NO:790:

(i) SEQUENCE CHARACTERISTICS:
        (A) LENGTH: 25 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:790:

```
Ser Ser Asp Val Thr Val Asn Glu Gly Ser Ser Val Thr Leu Leu Cys
 1               5                  10                  15
Leu Ala Ile Gly Arg Pro Glu Pro Thr
                20                  25
```

(2) INFORMATION FOR SEQ ID NO:791:

(i) SEQUENCE CHARACTERISTICS:
        (A) LENGTH: 49 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:791:

```
      Pro  Leu  Ala  Lys  Val  Val  Leu  Gln  Cys  Xaa  Arg  Ala  Leu  Asn  Met  Pro
        1             5                       10                            15

Tyr  Met  Glu  Gln  Gly  Gly  Tyr  Cys  Met  Ala  Leu  Arg  Glu  Lys  Cys  Cys
                      20                       25                      30

Phe  Tyr  Thr  Asn  His  Leu  Gly  Ile  Ile  Arg  Asp  Asn  Met  Ala  Met  Leu
                35                       40                       45

Lys
```

( 2 ) INFORMATION FOR SEQ ID NO:792:

( i ) SEQUENCE CHARACTERISTICS:
        ( A ) LENGTH: 49 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:792:

```
      Ser  Leu  Ser  Glu  Val  Val  Leu  Gln  Asn  Arg  Arg  Gly  Leu  Asp  Leu  Leu
        1             5                       10                            15

Phe  Leu  Gln  Glu  Gly  Gly  Leu  Cys  Ala  Ala  Leu  Lys  Glu  Glu  Cys  Cys
                      20                       25                      30

Phe  Tyr  Ala  Asp  His  Thr  Gly  Ile  Val  Arg  Asp  Ser  Met  Ala  Lys  Leu
                35                       40                       45

Arg
```

( 2 ) INFORMATION FOR SEQ ID NO:793:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:793:

```
      Ser  Arg  Arg  Trp  Phe  Asp  Lys  Ser  Phe  Thr  Phe  Val  Val  Phe  Lys  Asn
        1             5                       10                            15

Gly  Lys  Met  Gly  Leu  Asn  Ala  Glu  His  Ser  Trp  Ala  Asp  Ala  Pro  Ile
                      20                       25                      30

Val  Ala  His  Leu  Trp  Glu  Val  Ser  Phe
                35                       40
```

( 2 ) INFORMATION FOR SEQ ID NO:794:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: protein ( v ) FRAGMENT TYPE: internal ( x i ) SEQUENCE DESCRIPTION: SEQ ID NO:794:

```
      Thr  Asn  Arg  Trp  Phe  Asp  Lys  Ser  Phe  Asn  Leu  Ile  Ile  Ala  Lys  Asp
        1             5                       10                            15

Gly  Ser  Thr  Ala  Val  His  Phe  Glu  His  Ser  Trp  Glu  Asp  Gly  Val  Ala
                      20                       25                      30

Val  Leu  Arg  Phe  Phe  Asn  Glu  Val  Phe
```

(2) INFORMATION FOR SEQ ID NO:795:

(i) SEQUENCE CHARACTERISTICS:
        (A) LENGTH: 28 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:795:

```
Gly Gly Lys Ala Leu Ser Gly Arg Thr Ser Ser Ser Ala Trp Lys Gly
 1               5                  10                  15
Ala Cys Phe Lys Asp Ser Ile His Thr Phe Cys Pro
                20                  25
```

(2) INFORMATION FOR SEQ ID NO:796:

(i) SEQUENCE CHARACTERISTICS:
        (A) LENGTH: 29 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO:796:

```
Gly Gly Lys Ala Leu Ser Ser His His Thr Ala Ser Pro Trp Asn Leu
 1               5                  10                  15
Ser Pro Phe Ser Lys Thr Ser Ile His His Gly Ser Pro
                20                  25
```

(2) INFORMATION FOR SEQ ID NO:797:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Oligonucleotide (iii) HYPOTHETICAL: NO (iv) ANTI-SENSE: NO (xi) SEQUENCE DESCRIPTION: SEQ ID NO:797:

```
AACTGGGCGG AGTTAGGG                                          18
```

METHOD FOR GENERATION OF SEQUENCE SAMPLED MAPS OF COMPLEX GENOMES

RELATED APPLICATIONS

This application is a continuation-in-part of U.S. application Ser. No. 08/078,471, filed Jun. 15, 1993, abandoned, the entire contents of which are hereby incorporated by reference herein.

The present invention relates to recombinant DNA technology. More particularly, the invention concerns a process for rapidly generating a physical sequence map of large complex genomes, including human chromosomes. The sequence mapping process ("sequence sampled mapping") depends on the use of cosmid vectors containing endogenous bacteriophage promoters to allow for the sequencing of end-specific nucleotides of each member of a contiguous library of cosmid clones.

BACKGROUND OF THE INVENTION

The complete analysis of large complex genomes, such as genomes of higher eukaryotes, including human, requires the extensive isolation, purification and analysis of large fragments of DNA by cloning, generally in *E. coli*. In the past, the lambda bacteriophage cloning system has been used most frequently to generate genomic libraries. The lambda bacteriophage vectors usually accommodate inserts up to about 20 kb. Presently the primary system used to clone and manipulate large DNA fragments is that of cosmid vectors. Cosmid vectors allow the packaging of DNA fragments of up to about 45 kb in plasmids containing bacteriophage cos sites for in vitro packaging.

The analysis of complex genomes involves the application of both "top-down" and "bottom-up" mapping strategies. The "top-down" strategy depends on the separation on pulsed field gels of large DNA fragments generated using rare restriction endonucleases for physical linkage of DNA markers and the construction of long-range maps [Schwartz et al., Cell 37:67 (1984); Southern et al., Nucleic Acids Res. 15:5925 (1987); Burke et al., Science 236:806 (1987)]. The "bottom-up" strategy depends on identifying overlapping sequences in a large number of randomly selected bacteriophage or cosmid clones by unique restriction enzyme "fingerprinting" and their assembly into overlapping sets of clones. "Top down" mapping is inherently more rapid and less labor intensive, but does not generate sets of DNA clones for further structural or biological analysis. "Bottom-up" mapping generates the required sets of overlapping clones but application of current strategies and pattern matching algorithms to mammalian genomes will require the analysis of thousands to tens of thousands of individual clones for the generation of complete maps.

Clone-based physical maps have been extremely useful as the framework for many types of structural and biological studies and have been constructed for several model organisms including *E. coli*, *C. elegans*, *D. melanogaster* and *S. cerevesiae* (Kohara et al., 1989, Cell, 50:495–508; Oliver et al., 1992, Nature, 357:38–46; Sulston et al., 1992, Nature, 356:37–41; Merriam et al., 1991, Science, 254:221–225). In the past few years, a variety of techniques have been utilized for the construction of ordered clone maps including cosmid and phage contig-building (Olson et al., 1986, Proc. Natl. Acad. Sci., USA, 83:7826–7830; Coulson et al., 1986, Proc. Natl. Acad. Sci., USA, 83:7821–7825), analysis of arrayed libraries (Evans and Lewis, 1989, Proc. Natl. Acad. Sci., USA, 86:5030–5034), linking libraries and pulsed-field gel analysis (Poustka and Lehrach, 1986, Trends Genetics, 2:174–179; Hermanson et al., 1992, Genomics, 13:134–143) and the assembly of YAC clone contigs (Bellanne-Chantelot et al., 1992, Cell, 70:1059–1068; Foote et al., 1992, Science 258:60–66).

Another approach for the assembly of clone maps is the use of sequence tagged sites (STSs; Olson et al, 1989, Science, 245:1434–1435): mapped DNA sequence fragments that can be detected by amplification of specific products using the polymerase chain reaction (PCR; Saiki et al., 1988, Science, 239:487–491). STS content mapping, the analysis of STS markers present in large contiguous inserts in yeast artificial chromosomes, has proven to be an efficient method for assembling clone maps of 100 to 300 kb average resolution and has been successful for the assembly of low resolution maps of human chromosomes Y and 21 (Foote et al, 1992, supra; Chumakov et al., 1992, Nature, 359:380–387). The analysis of STS content in large DNA fragments carried in somatic cell (Delattre et al., 1991, Genomics, 9:721–727) or radiation-reduced cell hybrid lines (Cox et al., 1990, Science, 250, 245–250) also provides a powerful mapping technique.

Large numbers of mapped STS markers have been isolated for several human chromosomes (Tanigami et al., 1992, Am J Hum Genet, 50:56–64; Hori et al., 1992, Genomics, 13:129–133; Heding et al., 1992, Genomics, 13:89–94) but do not necessarily provide the needed resources for large scale chromosome mapping. In many cases, the value of these reagents is limited because the probes are poorly characterized, not generally available to the scientific community or can not be used for routine screening under a set of standardized conditions. Thus, methods of producing DNA markers suitable as reagents for large scale chromosome mapping are desired.

In addition, a major challenge of the human genome project is development of new approaches for physical analysis and sequence determination. Major progress has been made with the sequencing of large regions of DNA for significant portions of the *E. coli* genome, chromosome III of *S. cerevisiae*, several cosmid sized pieces of DNA from *C. elegans*, human, and a 100 kb T cell receptor region from mouse. See, e.g., Daniels et al., Science, 257:771–778 (1992); Martin-Gallardo et al., Nat. Genet. 1:34–39 (1992); Oliver et al., Nature, 357:38–46 (1992); Sulston et al., Nature, 356:37–41 (1992); and Wilson et al., Genomics, 13:1198–1208 (1992). The precise determination of each base for these sequences, however, has been a labor intensive and costly undertaking.

In addition, the construction of high resolution physical maps and the acquisition of sequence have previously been considered separate efforts. Thus, new methods are desired, such as combining the steps of physical mapping and sequencing, to sequence 25%–100% of a particular portion of genomic DNA from megabase sized regions to whole genomes or chromosomes more economically than previous efforts and with reasonable accuracy.

SUMMARY OF THE INVENTION

The present invention relates to a rapid and powerful sequence mapping method, called "sequence sampled mapping", for sequencing complex genome, said method comprising sequencing the end-specific nucleotides of each member of a library of cosmid clones, and assembling a sequence sampled map by correlating the end-specific sequence information with the relative spatial relationship between the cosmids. The invention method is applicable to genomic DNA, preferably mammalian chromosomes, and in a preferred embodiment, employs a "bottom-up" mapping strategy, which allows for the simultaneous analysis of multiple cosmid clones for the detection of overlaps. The sequence sampled mapping method permits sequence overlaps to be determined by map positions, reducing the reliance on determining regions of unique shared sequence.

In a particular embodiment of the invention, the method comprises, in any order, grouping of cosmid clones by chromosome or YAC hybridization, construction of high density cosmid contigs by restriction based fingerprinting, and direct and automated DNA sequencing from cosmid clones.

The sequence sampled mapping method is useful for the completion of high density sequence-based maps, and ultimately, for the complete sequencing of genomic DNA directly from cosmid clones. In addition, the resulting sequence information allows the detection of many genes by sequence analysis with computer programs such as FASTA, BLAST, GRAIL and others under development; allows the development of sequence tag sites (STSs) and polymorphic repeats at an actual physical spacing of a few kilobases (see, e.g., Olson et al., 1989, *Science*, 245:1434–1435); and allows direct PCR amplification of any part of the genome, independent of clone libraries. The invention method is also amenable to automation using the particular characteristics of the sCOS vector and cloning system. The resulting sequence sampled map is also useful, employing on-line parallel processing microcomputers which use existing software programs that have been adapted for parallel processing, for the computer analysis of genomic DNA.

BRIEF DESCRIPTION OF DRAWINGS

FIG. 2A illustrates that cosmids prepared in vector sCOS-1 or one of its derivatives can be used to synthesize end-specific sequences (e.g., probes for the detection of overlaps).

FIG. 2B illustrates the inoculation of cosmid clones on the surface of a nitrocellulose or nylon filter from 96-well archive plates stored at −70° C. Each clone on the "grid" is assigned a unique identifying Y and X axis coordinate. Individual clones in the collection contain the innate capacity of generating probes specific for the extreme ends of the genomic DNA insert and detecting overlapping clones on the filter. The arrows show the locations of potential overlapping clones detected by hybridization of probes generated from the clone at coordinates Y=2, X=7.

FIG. 3A presents the predicted linkage and orientation of a representative cosmid contig generated by multiplex analysis of the chromosome 11q cosmid set and data analysis using the computer program "Contig-maker". The computer output indicates the coordinates of linked clones (X,Y) and the arrows denote the orientation of the linkage.

FIG. 3B presents a restriction map and the location of probes used to establish unequivocal overlap of the cosmids.

Figures 3A, 3B:
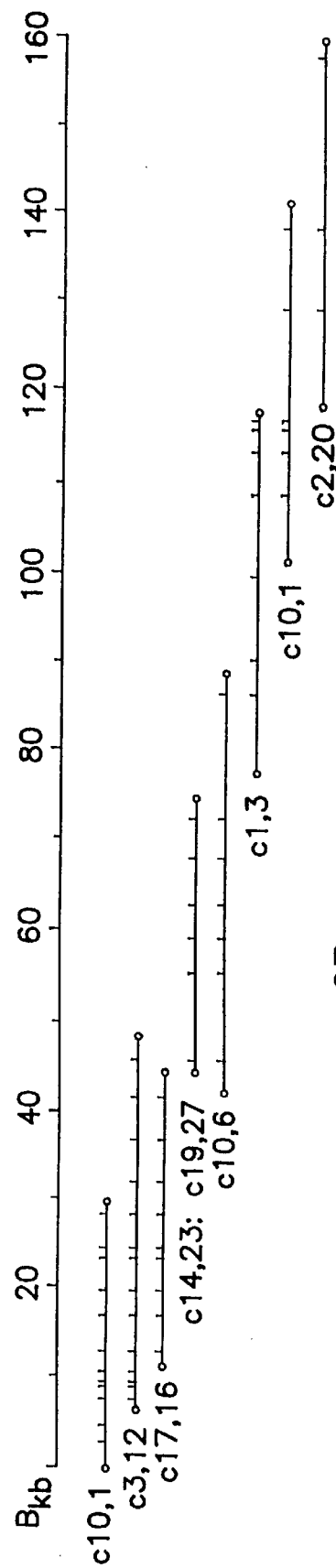
FIG. 3A–3B shows predicted contigs from human chromosome 11q and restriction enzyme digestion analysis.

A restriction map of the overlapping clones detected in FIG. 3A was determined by the analysis of partial EcoRI digestion products hybridized with $^{32}$P-labeled T3 or T7 promoter-specific oligonucleotides. Overlapping areas not confirmed by restriction map analysis were confirmed by hybridization analysis using end-specific RNA probes generated from individual cosmid clones. Cosmid clones c14,23 and c19,27 are identical. □ indicates bacteriophage T3 promoter, ■ indicates bacteriophage T7 promoter.

Figure 4A:
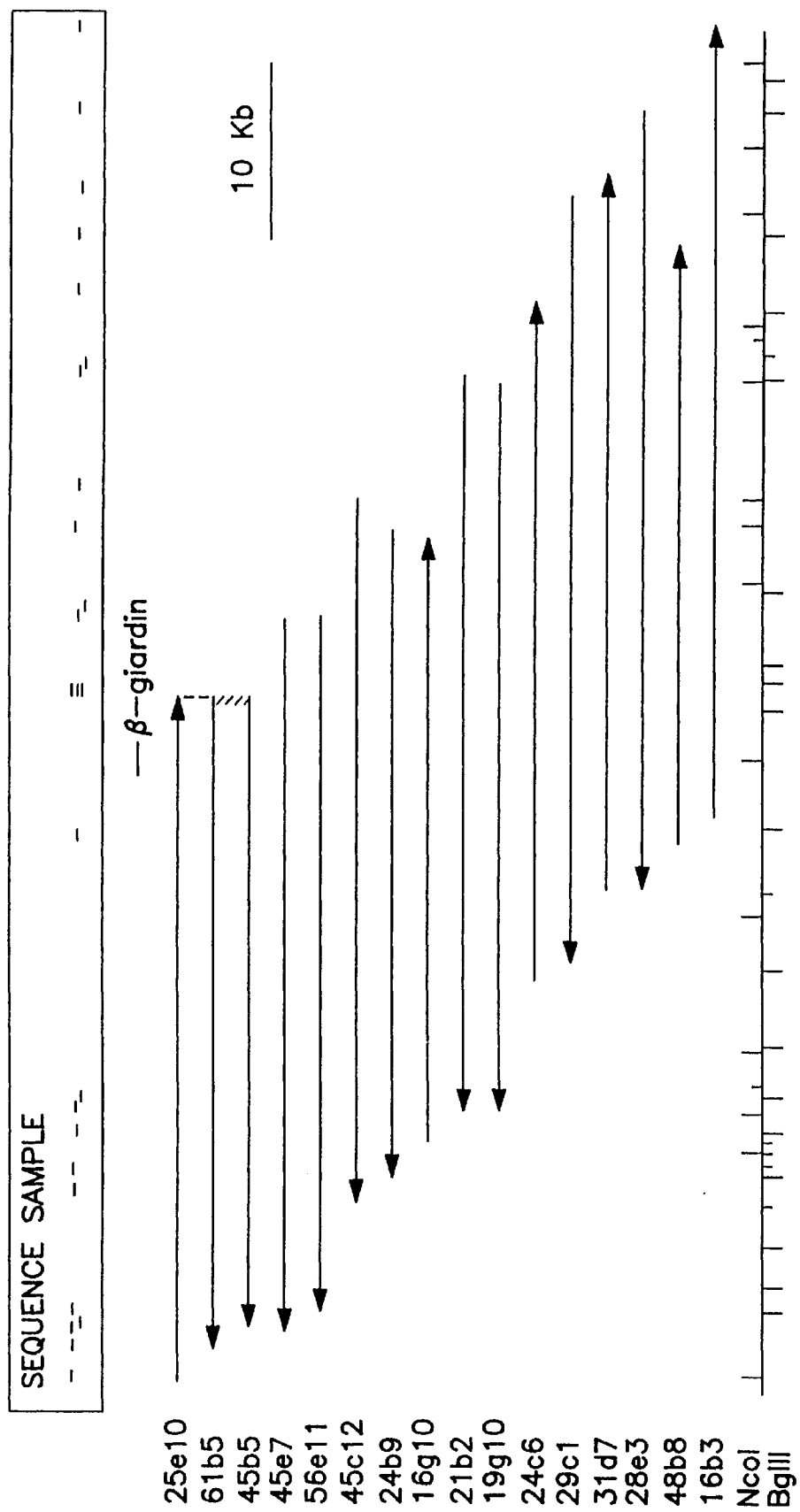
Figure 4B:
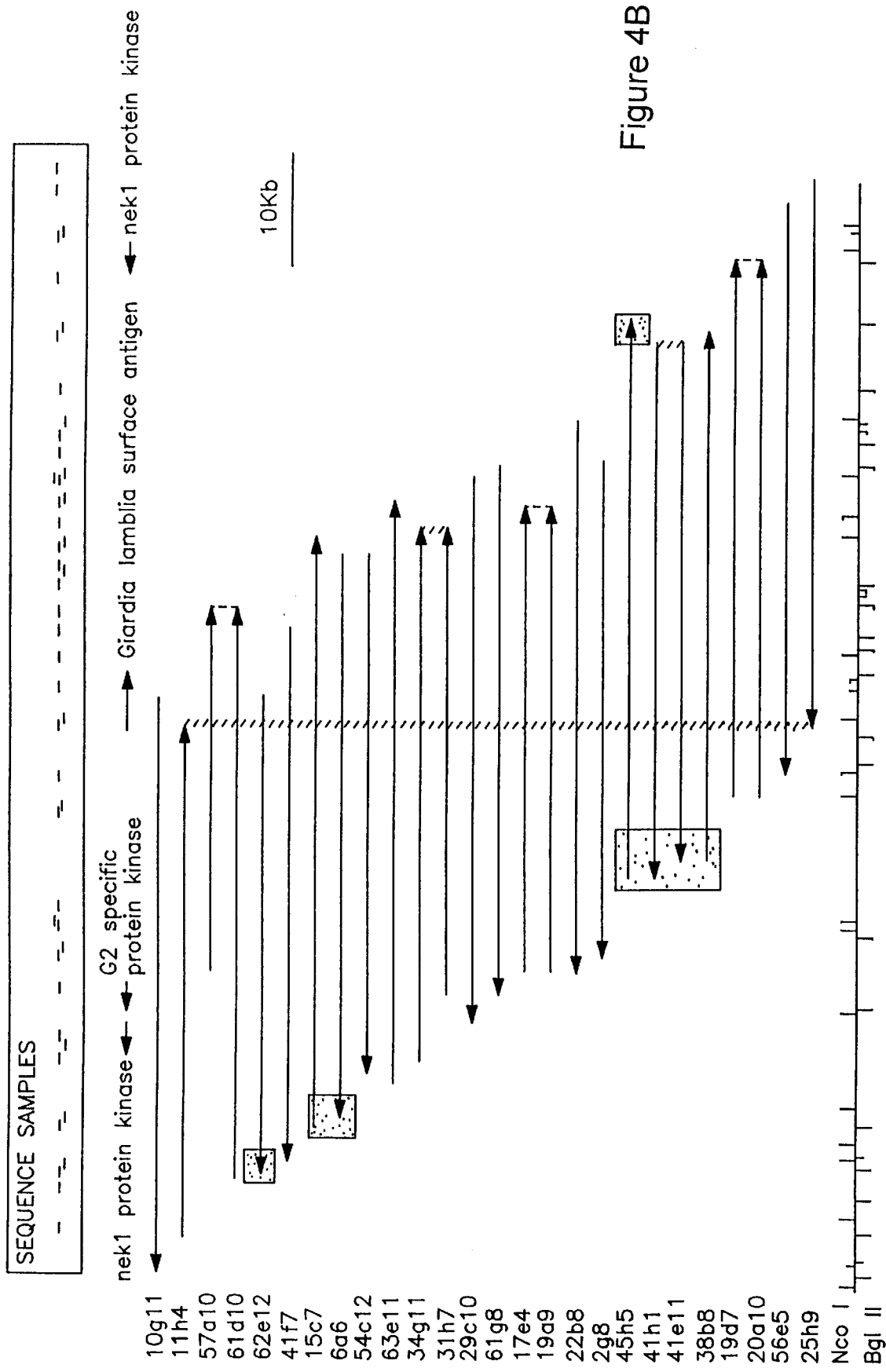

FIG. 4A–4B presents physical and sequence maps of the (A) β-giardin and (B) a second random genomic region with arrows at the ends of cosmids corresponding to their t7 ends. Smaller hash marks represent locally regionalized, but not fully ordered restriction fragments. Regions of sequence which match the genes annotated on the figure are shown with a greyed-in box.

FIG. 5A–F presents alignment of various regions of sequence homology found by BLAST searches of the protein sequence databanks with cosmid end sequences.

Figure 6:
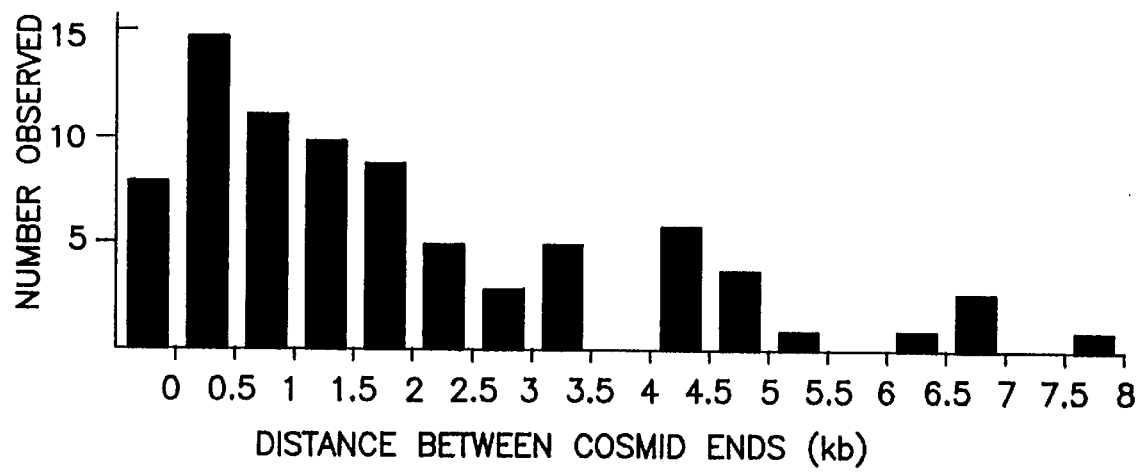

FIG. 6 presents a histogram showing the distances between ordered cosmid ends and their frequency of occurrence in the two contigs determined in this study.

Figure 7:
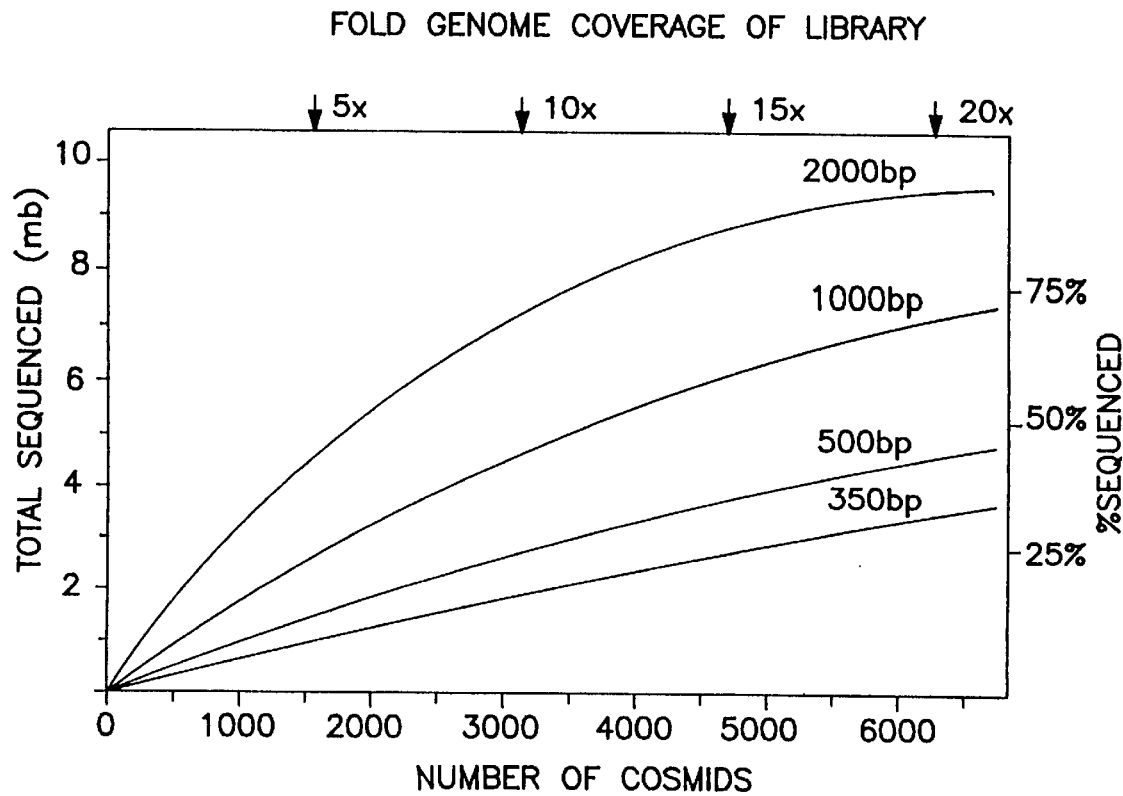

FIG. 7 presents a plot of the number of sequenced cosmid ends versus the total amount of *Giardia lamblia* genome sequenced. Calculations are based on the equations of Lander and Waterman [*Genomics*, 2:231–239 (1988)] assuming an overlap detection of 50 bases.

Figure 8:
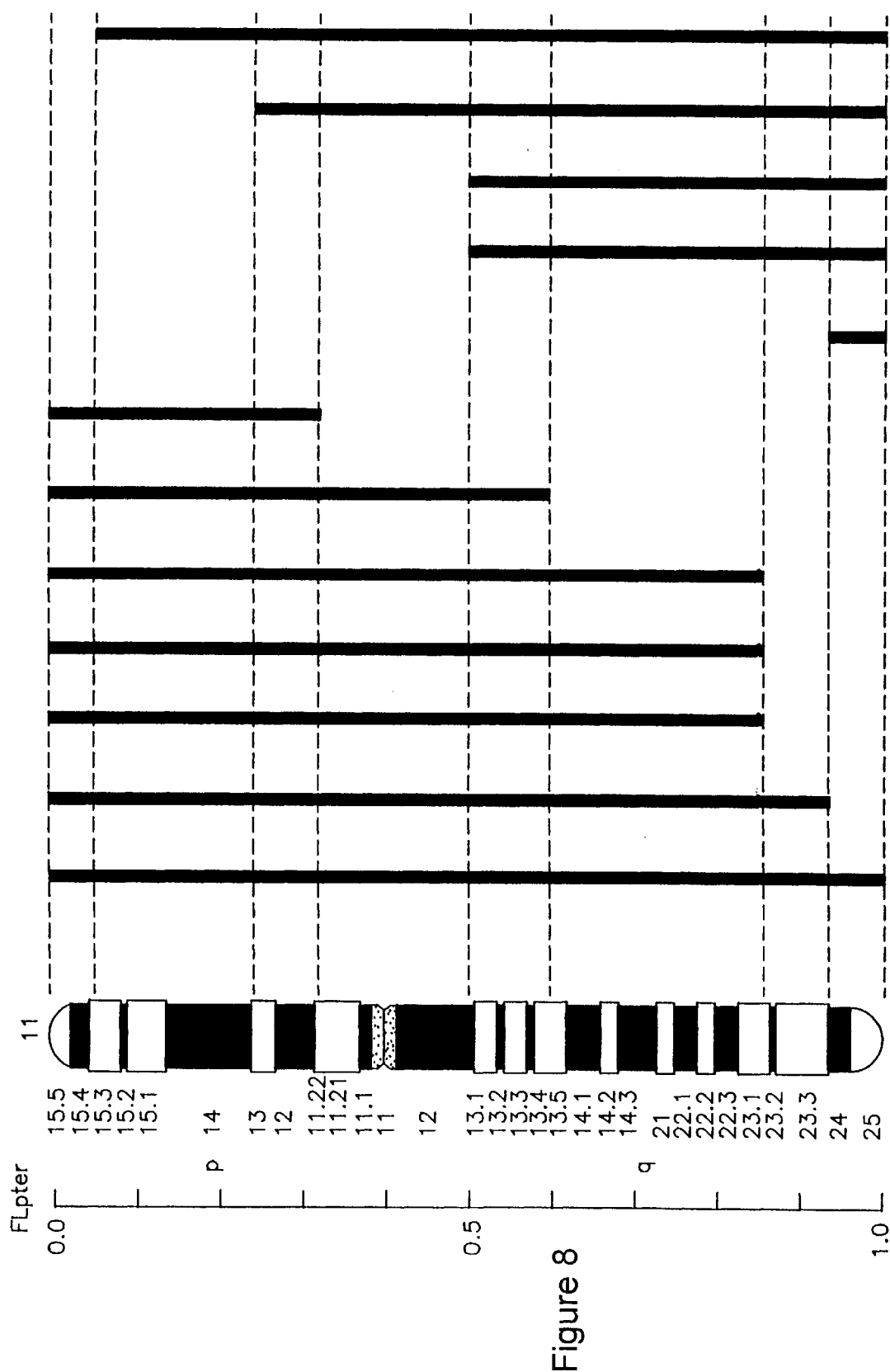

FIG. 8 presents regional mapping of a chromosome 11 STS using a panel of somatic cell hybrids. This analysis shows the regional mapping of an STS to bin 2, FLpter 0.05–0.24, by PCR analysis and is typical of the bulk of STS primer results derived under these conditions. The hybrid mapping panel breakpoints are shown relative to human chromosome 11.

FIG. 9A and 9B present protein sequence alignments of putative genes detected from analysis of DNA sequences. DNA sequence determined from cosmid clones were translated into six reading frames and used to search GenPept, PIR or Swiss-Prot protein sequence databases using BLASTX. The clone name from which the sequence was derived is shown next to its translated sequence. The flanking numbers indicate the matching position in the nucleotide sequence of the cosmid or the protein sequence of the database entry. The one amino acid code translation is shown with X=any amino acid (generally caused by the inability to determine a base) and*=a stop codon. The X in cSRL-7d2 has a one in four chance of being a stop codon.

DETAILED DESCRIPTION OF THE INVENTION

In accordance with the present invention, there is provided a method for sequencing complex genomes. The invention method comprises:

(1) sequencing the end-specific nucleotides of each member of a library of cosmid clones,
   wherein said cosmid clones are prepared by inserting genomic DNA fragments into cosmid vectors,
   wherein the cosmid vectors include sequences of nucleotides that flank at least one end of the inserted DNA, and that serve as transcription initiation sites for the synthesis of a nucleic acid specific to the ends of the inserted DNA, and (2) assembling a sequence sampled map by correlating the end-specific sequence information with the relative spatial relationship between the cosmids.

In a preferred embodiment, the invention sequence sampled mapping method provides for the sequencing of the entire genome of any organism for which genomic DNA is available, preferably mammalian genomic DNA, more preferably human genomic DNA.

As used herein, the phrase "end-specific nucleotides of each member of a library of cosmid clones" refers to the nucleotide sequences at the extreme 5' and 3' ends of a given genomic DNA insert. Typically, the amount of nucleotides sequenced from each end-specific nucleotide sequence will be at least 100, preferably 250, more preferably 350, yet more preferably 550, with at least 1000 nucleotides being especially preferred. The amount of sequenced nucleotides required for the practice of the invention method varies as a function of the depth of cosmids to be sequenced.

The phrase "depth of cosmids", and grammatical variations thereof, refers to the number of overlapping cosmids that contain, in common, a specified region (i.e., 1 nucleotide) of genomic DNA to be mapped and sequenced. For example, a 20× (20-fold) depth of cosmids covering a specified region of genomic DNA refers to 20 cosmids that, on average, contain at least one nucleotide of genomic DNA in common.

The depth of cosmids is chosen so as to maximize the number of unique genomic DNA insert ends and to provide a desired average spacing between the respective 5' or 3' ends of two consecutive contiguous cosmid clones. For example, if on average, each cosmid contains approximately 40 kb of genomic DNA insert, then a cosmid depth of 20× would produce, on average, a spacing of 1000 nucleotide base pairs between the respective 5' or 3' ends of each consecutive genomic DNA insert. Thus, sequencing approximately 500 base pairs of the 5' and 3' ends of all given cosmids will provide genomic DNA sequence data for approximately 50% of the respective genomic DNA sample.

The depth of cosmids can be varied by methods well-known in the art. One method is to select any one or combination of restriction enzymes that recognize a specific genomic DNA sequence, preferably a 4-bp sequence ("4-bp-recognizing"). Next the restriction enzyme(s) are employed to either partially or completely digest a given genomic DNA sample so as to produce genomic DNA insert fragments approximately 40–45 kb in length that are unique with respect to other genomic DNA insert fragments by as little as 100 base pairs to as great as 5–10 kb. Restriction enzymes that recognize 4 bp sequences suitable for use herein include, for example: Sau3A, AccII, AluI, BSP50, FnuDII, HaeIII, HhaI, the isoschizomers thereof, and the like.

A twenty-fold library generated by partial digestions of genomic DNA with several different restrictions enzymes would greatly increase the number of potential cloning sites and reduce the number of cloned ends which are exactly the same. For example, multiple 5–10 fold deep libraries, from the same genomic DNA source, can each be generated with a unique four-bp-recognizing restriction enzyme. This would require straightforward modifications to the COS vectors described hereinafter, e.g., adding appropriate polylinker sites. The uniquely restricted libraries can then be combined to arrive at libraries with a substantially high level of cosmid depth (e.g., at least about 20-fold deep, preferably at least about 40-fold deep, and more preferably at least about 50-fold deep). Thus, a 21-fold library may be constructed from three sub-libraries of 7-fold cosmid depth, whereby each sub-library is produced with a different four-bp-recognizing restriction enzyme.

One of skill in the art will recognize that by varying any one or both of the above-described parameters, sequencing of varying percentages of a given genomic sample becomes feasible, such as at least 25%, preferably 50%, more preferably 75%, with 100% (i.e., the entire genome) being especially preferred (see, e.g., FIG. 7). For example, in the above-example, increasing the depth of cosmids from 20× to 40× and sequencing 500 bp of each end of genomic DNA inserts provides the sequence for 100% of the 40 kb genomic DNA sample. Alternatively, in the above-example, increasing the amount of nucleotides sequenced from 500 to 1000 bp also provides the sequence for 100% of the 40 kb genomic DNA sample. Stated another way, increasing the average lengths of sequences determined, to about one kilobase, would result in nearly complete one-pass sequencing of a genome or chromosome at a fraction of the cost.

Either prior to, concurrently, or following the construction of contigs or determining the relative spatial relationship between the cosmid clones described above, the sequencing of end-specific nucleotides step of the present invention, is conducted to provide the sequence information that will be assembled into the "sequence sampled map".

The sequencing step may be carried out either manually or using an automated DNA Sequencer employing well-known methods, such as, for example, specific or degenerate primer extension, transposon primer insertion, ordered deletion, random shot gun sequencing, sequencing by hybridization, and the like. In a preferred embodiment, the 5' and 3' ends of each cosmid clone within a cosmid library is subjected to "one pass" (i.e., sequencing only once) automated DNA sequencing as described in Examples 2 & 3. Automated DNA sequencing devices are well-known and widely available to those of skill in the art, such as, for example, the sequencing devices available from Applied Biosystems (e.g., ABI 373A Sequencer combined with a Catalyst 800 robot, Foster City, Calif.), Pharmacia (Piscataway, N.J.), Millipore (Milford, Mass.), and the like.

It is recognized that automated DNA sequencing technology is currently progressing extremely rapidly. Thus, automated sequencing methods and devices that will allow sequencing of DNA fragments greater than 500 nucleotides (i.e., 1 to 5 kb) are also contemplated in the methods described herein (see, e.g., Ansorge et al., 1992, *Electrophoresis*, 13:616–619). Subsequently, when correction and verification of sequence information is desired for a particular region, an independent sequencing methodology may be employed, e.g., sequencing by hybridization, and the like.

Raw sequence information obtained from automated sequencing, or sequence sampled mapped sequence, can be analyzed immediately using on-line parallel processing microcomputers that employ existing software programs adapted for parallel processing. Sequence analysis software programs contemplated for use herein include, for example: GRAIL, which locates protein-coding regions in genomic DNA sequences (see, e.g., Uberbacher et al., PNAS, USA, 88:11261–11265, 1991); BLAST-n and BLAST-x, which compares sequence similarity between nucleotides and amino acid sequences, respectively (see, e.g., Altschul et al., J. Mol. Biol., 215:403–410, 1990); FASTA, which identifies sequence repeats (see, e.g., Pearson et al., PNAS, USA, 85:2444–2448, 1988). Raw sequence information may also be used advantagously to generate PCR primers useful in PCR assays for polymorphic repeats around specific sequences of interest, e.g., around "CA" nucleotide runs, other simple sequences, and the like.

In another aspect of the invention, prior to the completion of a complete physical map, raw sequence information can be used to generate "sequence-tagged sites" (STSs) as described in Example 3. The STSs can be used, e.g., for producing an ordered set of YACs, for the analysis of sites of chromosomal pathology (e.g., translocations, polymorphic repeats, and inversions), and the like. The production of STSs allows access to mapping markers based upon PCR amplification of known genomic sequence.

Briefly, as described above, DNA sequences are determined by sequencing directly from cosmid templates using primers complementary to the promoters (e.g., T3 and T7) present in the cloning vector. Oligonucleotide PCR primers are predicted by computer from a suitable amount of randomly selected cosmid-end-derived sequences, and are tested using a battery of genomic DNA templates, preferably corresponding to a specific chromosome. Cosmids are then regionally localized to the respective chromosome using fluorescence in situ hybridization and/or by the analysis of a somatic cell hybrid panel. Additional STSs corresponding to known genes and genetic markers on the respective chromosome may also be produced under the same series of standardized conditions.

As used herein, a "suitable amount" of STSs produced can be varied by one of skill in the art to provide a desired coverage (preferably uniform) of a respective chromosome. For example, it is well within the skill in the art to select an amount of STSs that provides an average spacing between conscecutive STSs within the range of about 1 kb up to about 500 kb, and also provides sufficient density for STS content mapping using YAC clones or contigs (see, e.g., Bellanne-Chaltelot et al., 1992, *Cell*, 70:1059–1068). Thus, e.g., assuming a chromosomal size of 126 mb (e.g., based upon chromosome 11 comprising 4.2% of the human genome), a collection of 370 STSs will have an average spacing of one STS per 340 kb and would provide sufficient density for STS content mapping using YAC clones. In a preferred embodiment, the quantity of STSs produced by the methods described herein provides an average spacing between conscecutive STSs within the range of about 1 kb up to about 5 kb.

As used herein, the phrase "assembling a sequence sampled map" refers to the step of ordering the nucleotide sequences obtained from the sequencing step into the order in which they naturally occur in the source genome. This is accomplished by correlating the end-specific sequence information obtained in step (1) above with the relative spatial relationship between the cosmids.

Once the sequence sampled map has been determined, a minimum tiling path of cosmids (just enough to cover the region once) can be used as sequencing templates. Each sampled sequence can then be extended in both directions to triple the effective sequence reads. The availability of inexpensive oligonucleotide primers will make this sequence walking an attractive option for finishing the sequence. One attractive approach which may make primer walking affordable is the use of contiguous hexamer oligonucleotides to specifically prime sequencing reactions (see, e.g., Kielec-zawa et. al., 1992, *Science*, 258:1787–91).

The term "relative spatial relationship between the cosmids" refers to the physical mapping of the genomic DNA inserts into the contiguous order and/or the respective orientations (e.g., 5'-3' or 3'-5') in which they naturally occur in the source genome. The relative spatial relationship may be determined either prior to, concurrently, or after the step of "sequencing the end-specific sequences of each member of a library of cosmid clones." In a preferred embodiment, the relative spatial relationship between the cosmids is determined concurrent (i.e., in parallel) with the sequencing of step (1) above.

The relative spatial relationship between the cosmids (i.e., physical map) can be determined by methods well-known in the art, such as fingerprinting by restriction enzyme mapping ("restriction-fragment-length mapping") employing several different restriction enzymes [see, e.g., Olson et al., Proc. Natl. Acad. Sci. USA 83:7826 (1986); Coulson et al., Proc. Natl. Acad. Sci. USA 83:7821 (1986); Kohara et al., Cell 50:495 (1987); and the like]; the "cosmid multiplex analysis" method as described in U.S. Pat. No. 5,219,726, incorporated herein by reference in its entirety; and the like.

Restriction fragment length mapping employs full and/or partial restriction enzyme digests. The partial digestion provides the order of restriction within a cloned genomic insert, and the full digestion provides the exact sizes of the restriction fragments. Partial digestion products are detected with non-insert probes specific to either side of the cosmid vector, which orients the sequence relative to the genomic map. The partial digestion restriction maps are reconciled with data from the full restriction digest to obtain a spatially correct physical map. The restriction enzyme maps of each cosmid are compiled into an overall map of the genomic region of interest, which could be derived from a YAC (Yeast Artificial Chromosome), BAC (Bacterial Artificial Chromosome), PAC (P1 Artificial Chromosome), MAC (Mammalian Artificial Chromosome), a whole chromosome, or a small whole genome.

In another embodiment of the present invention, the relative spatial relationship between the cosmids is determined by the "cosmid multiplex analysis" method as described in Example 1 and U.S. Pat. No. 5,219,726. The cosmid multiplex analysis method depends on the use of cosmid vectors allowing for the synthesis of corresponding RNA sequences (probes) or DNA sequences specific to the extreme ends of the DNA fragments contained within the cosmid, directly from the DNA inserts of the cosmid.

Briefly, cosmid libraries are constructed using vectors containing at least one bacteriophage promoter adjacent to the genomic DNA insert, positioned operatively for the transcription thereof. Preferably, the cosmid vectors contain two bacteriophage promoters flanking the DNA fragment ligated into the insertion site. Synthesis of an end-specific RNA probe from any clone in the collection allows the overlapping clones to be easily detected by hybridization. Because this strategy does not depend on pattern recognition for detecting overlaps, analysis may be carried out simultaneously on cosmid clones grouped together.

The "cosmid multiplex analysis" method is suitable for the unambiguous detection of overlapping regions as small as several hundred nucleotides in contiguous cosmids. Accordingly, the number of clones needed for map closure can be reduced by up to three-fold. Finally, this strategy represents essentially simultaneous cosmid "walking" and thus is basically non-random, allowing the investigator the freedom to pause and investigate some interesting biology rather than requiring completion of the map before it becomes useful.

It has been found that significant improvements in the speed and efficiency of "bottom-up" genomic mapping can be achieved, by 1) isolating restricted regions of large mammalian genomes in a "sublibrary"preorganized on a solid matrix, 2) using hybridization of end-specific probes for detection of overlapping clones in the collection, and 3) analyzing multiple clones simultaneously for the detection of all overlaps in the collection.

In accordance with the present invention, direct sequencing can then be carried out on the fragment ends of the individual cosmids which make up the resulting contig. This will generate in the range of about 350–550 base pairs of sequence information, separated by gaps of about 1–5 kb, depending on the chosen depth of cosmids employed. Thus, for a cosmid depth of 10–20×, in the range of about 20–50% of the complete chromosome sequence can be obtained very rapidly and at relatively low cost.

Thus, an alternate embodiment of the present invention provides a method for sequencing complex genomes, said method comprising:

(1) preparing a genomic library of cosmid clones by inserting DNA fragments from said genome into cosmid vectors, wherein the cosmid vectors include sequences of nucleotides that flank at least one end of the inserted DNA, and that serve as transcription initiation sites for the synthesis of end-specific probes, (2) arranging the cosmid clones, whereby each clone may be identified and replicas of said arrangement may be reproduced, (3) pooling portions of said cosmid clones and synthesizing pools of mixed end-specific probes from the DNA inserts that have been prepared from said pooled clones, wherein each pool contains fewer than all of the cosmid clones in the library, but all of the cosmid clones in the library are included in at least one pool, (4) hybridizing each pool of probes to a replica of said arranged cosmid clones and identifying the cosmid clones in each replica that hybridize to the probes, wherein said identified clones include the pooled cosmid clones and cosmid clones that contain DNA inserts that overlap with the DNA inserts in the pooled clones, (5) identifying the cosmid clones from among those identified in step (4) that hybridize to two or more pools of probes, thereby identifying groups of cosmid clones that include overlapping DNA, (6) assembling contigs from said groups, and (7) sequencing the end-specific nucleotides of each overlapping member of said cosmid clones.

In a preferred embodiment, the cross-hybridizing clones are identified by pairwise comparison of data sets obtained from two groups of cosmid clones containing at least one common clone. The cosmid clones are preferably pooled according to the rows and columns of a two-dimensional matrix.

Preferably, the cosmid vectors used in the above processes comprise two oppositely oriented promoters, each of which is specific for a bacteriophage RNA polymerase, positioned on two sides of the cloning site. Most preferably, the vectors contain T3 and T7 endogenous bacteriophage promoters flanking the cloned genomic DNA. Vectors containing at least two cos sites are particularly preferred, since they allow the use of DNA fragments without the need for prior size separation.

From the list of linked clones produced by this technique, contigs can be assembled either manually or through computer analysis of the data, then the fragment ends of the DNA inserts in the individual cosmids can be subjected to automated DNA sequencing. This will typically generate ordered sequence fragments about 350–550 base pairs in length, separated by gaps in the range of about 1–5 kb, depending on the chosen cosmid depth.

As used herein, the term "genomic library" refers to a mixture of clones constructed by inserting fragments of genomic DNA into a suitable vector. The term "library" implies the existence of large numbers of different recombinants out of which only a few are of immediate interest to the investigator. Genomic DNA can be the entire genome, a single chromosome, or a portion of a chromosome, such as the 300–400 kb portions of chromosomal DNA typically contained within YACs, of a given organism.

The terms "cosmid" and "cosmid vector" and grammatical variations thereof, are used interchangeably herein and refer to plasmid vectors that contain a lambda bacteriophage cos (cohesive end) site. The lambda bacteriophage packaging system selects DNA molecules of about the size of the lambda genome (37–52 kb). Accordingly, plasmid recombinant DNA having a minimum size of about 38 kb and a maximum size of about 52 kb (about 78% and about 105% of phage lambda, respectively), can be packaged in vitro in the lambda phage coat. In addition to the cos site(s) cosmid vectors usually contain a marker gene allowing for selection in bacteria (antibiotic resistance gene), and one or more unique restriction sites for cloning. Plasmids with a large variety of cloning sites and prokaryotic and eukaryotic selection markers can be converted to cosmids by insertion of the lambda cos region.

The term "cosmid clone" refers to a cosmid vector that contains a genomic DNA insert. The term "plasmid" refers to circular, double-stranded DNA loops which in their vector form, are not bound to the chromosome. The term "nucleic acid" refers to a synthetic or naturally occurring DNA or RNA molecule.

As used herein, the term "a promoter specific for a bacteriophage RNA polymerase" means a wild-type or non-wild-type promoter that can be used by the bacteriophage RNA polymerase for in vitro transcription of a DNA fragment. When a non-wild-type promoter is used for such in vitro transcription of a DNA fragment, transcription will occur at a rate which is at least 10% of the rate at which transcription would have occurred if a wild-type or native promoter had been used by the bacteriophage RNA polymerase to transcribe the DNA fragment in vitro.

The term "cloning site" as used herein, means restriction endonuclease site on the DNA sequence of the cosmid vectors of the present invention where a DNA fragment can be inserted without deleting any of the original DNA.

Reference to a promoter positioned "operatively for transcription of a DNA fragment", as used herein, means that the promoter will be positioned in such a way that any DNA sequences between the promoter's transcriptional start site and the DNA fragment will not prevent transcription of at least a portion of the DNA fragment by the promoter. The term "at least a portion" means that preferably at least 8 base pairs and more preferably at least about 30 bp of the DNA fragment will be transcribed.

The terms "end-specific RNA sequences", "RNA probes", and grammatical variations thereof, are used to refer to hybridization probes obtained by transcription of corresponding DNA fragments.

Clones are overlapping if they contain contiguous DNA in the same relationship as that in the genome. One method for detecting overlaps is to synthesize an RNA probe from one end of a first clone. If this probe detectably hybridizes with an end of the second clone under standard hybridization conditions, the two clones are overlapping [Wahl et al., PNAS USA 84:2160 (1987)].

The term "contig" was introduced by Rodger Staden, Nucleic Acids Res. 8:3673 (1980) in connection with DNA sequence analysis, and refers to groups of clones with contiguous nucleotide sequences.

Figure 2A:
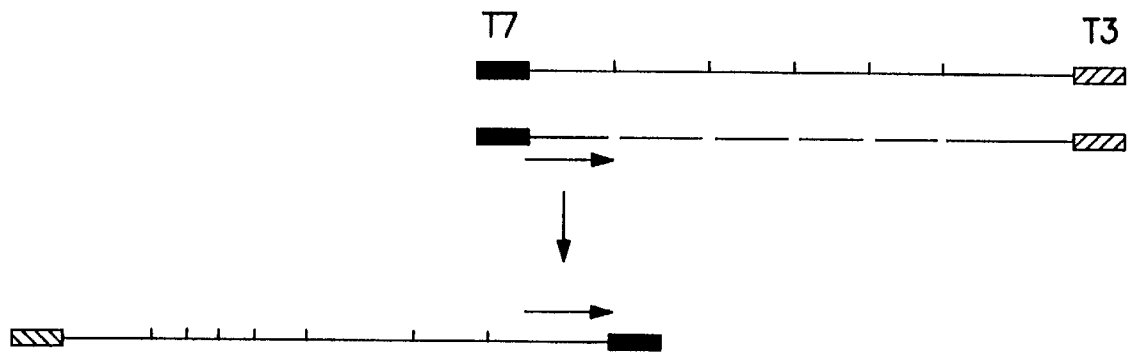
FIG. 2A–2B illustrates a strategy useful for analysis of physical linkage using groups of cosmids.
Figure 2B:
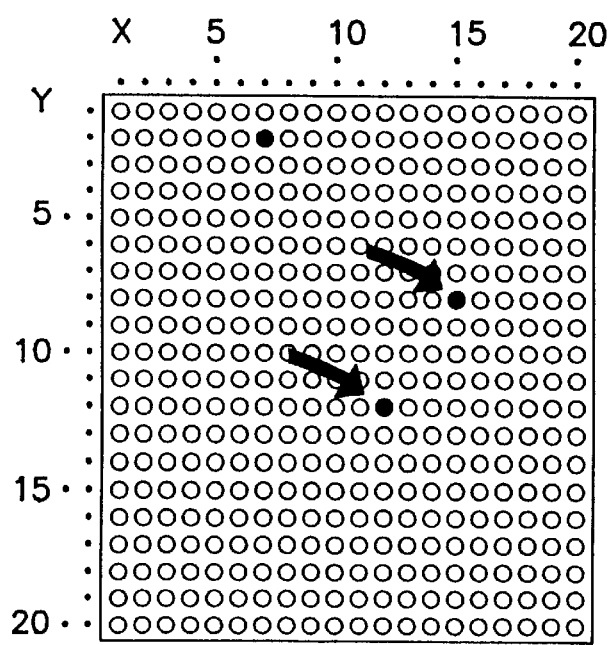

The cosmid multiplex analysis method employs essentially the strategy illustrated in FIG. 2A–2B used for genomic mapping using cosmid vectors.

In a first step, a genomic library which represents a limited portion of a genome is constructed in a cosmid vector allowing for the synthesis of RNA probes and DNA strands for sequencing directly from insert DNA using endogenous bacteriophage promoters. A convenient and powerful way of subdividing the human genome for the preparation of libraries is through chromosome purification by flow cytometry [Gray et al., Cold Spring Harbor Symp. LI 1986p. 141].

Cosmid vectors suitable for constructing a genomic "sublibrary" include the pWE vectors described by Wahl et al., in Proc. Natl. Acad. Sci. USA 84:2160 (1987), e.g. pWE2, pWE4, pWE8 pWE10, pWE15, and pWE16, preferably pWE15 and pWE16. The construction of these vectors is described in the Materials and Methods section of the cited article and in Evans et al., Methods in Enzymology 152:604 (1987). These vectors, in addition to replication and selection functions, such as plasmid origin of replication, bacterial genes specifying antibiotic resistance, and the bacteriophage lambda cohesive termini (cos sequences), contain the transcription promoters from either bacteriophage SP6, T7 or T3 flanking a unique BamHI cloning site.

In one embodiment, cosmid vectors containing a duplicated cos sequence are employed. These "sCOS"vectors have the following important characteristics: 1) the presence of two cos sites such that packaging could be carried out with high efficiency and without requiring size selection of the insert DNA; 2) the presence of T3 and T7 bacteriophage promoters for the synthesis of "walking" probes; 3) unique restriction sites for removing the insert and to aid in restriction mapping; 4) selectable genes for gene transfer in eukaryotic cells; and 5) a plasmid origin of replication giving a high yield of cosmid DNA for preparing templates.

Figure 1:
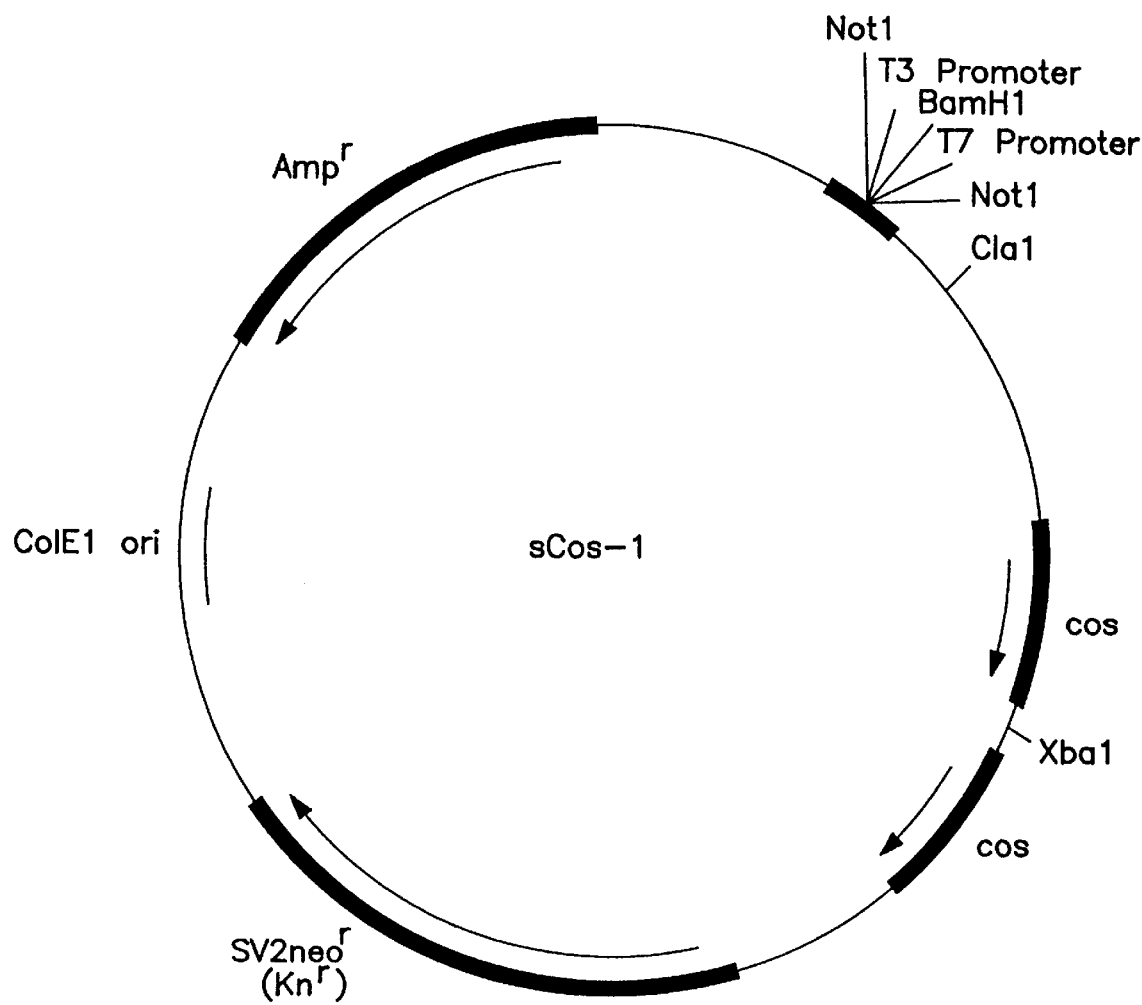
FIG. 1 shows the vector sCOS-1 designed for cosmid multiplex analysis. The vector contains bacteriophage T3 and T7 promoters flanking a unique BamHI cloning site, NotI sites for expedited restriction mapping and excision of the insert DNA, duplicated cos sites for high efficiency microcloning, a dominant selection for transfection into mammalian cells, Amp and Kn resistance genes, and ColE1 origin of replication.

The construction of plasmid sCOS-1 has previously been described. Plasmid sCOS-1 is illustrated in FIG. 1. The design of this plasmid (and derivatives thereof) allows for rapid production of RNA probes specific for both ends of the inserted DNA sequences. In addition, this design allows for the automated sequencing of the 5' and 3' ends of the genomic DNA insert.

Plasmid vector, sCOS-1, shown in FIG. 1, is 6.7 kb in size and has a cloning capacity of 31 to 48 kb. As with pWE vectors, bacteriophage T3 and T7 promoters were oriented into the BamHI cloning site to allow direct synthesis of end-specific RNA probes for molecular "walking" and to allow sequencing the end-specific nucleotides of a given genomic DNA insert. Previous experience with pWE cosmids suggested that NotI restriction sites may not be ideal for excision or mapping of inserts in some regions of the genome where NotI sites might be clustered. Therefore, additional cosmid vectors with other rare restriction sites have been constructed, by substituting the cloning/polymerase sites of sCOS-1 with sequences containing NotI and SacII sites (sCOS-2) or SfiI sites (sCOS-4). The asymmetric rare sites in sCOS-2 are useful for cloning ends of large NotI or SacII fragments for isolation of "linking" clones for long range mapping by pulsed field gel analysis [Buiting et al., Genomics 3:143 (1988)]. Also, vectors which lack NotI sites, such as sCOS-4, would potentially allow the selection of clones containing unique NotI junction fragments by hybridization with NotI-specific oligonucleotides [Estivill et al., Nucleic Acids Res. 15:1415 (1987)].

The double cos site sCOS vectors make feasible the preparation of representative libraries from very small amounts of purified, partially digested DNA, and are, therefore, presently preferred for carrying out the method of the present invention.

One of skill in the art can modify the sCOS vectors employed herein in a variety of ways to make them more suitable for restriction-fragment-length mapping using partial digestion (see, e.g., Kohara et al., Cell 50:495–508 (1987). For example, an "sCOS-derivative"vector useful in the invention methods described herein can include, intron encoded endonuclease sites which recognize approximately 20 base pairs, and a multiple cloning site (i.e., polylinker) which will ligate with partially-digested genomic DNA from most commercially available restriction enzymes that recognize four bases and generate staggered ends.

For determining the relative spatial relationship between the cosmid clones, the individual clones of the genomic library are arranged on a nitrocellulose or nylon filter matrix and each clone is identified by unique coordinates. If the randomly chosen clones are arranged in a two-dimensional matrix, they are identified by unique X and Y coordinates. For convenience in handling, the pattern of the matrix is preferably based on the pattern and spacing of wells of a standard 96-well microtitre plate and the repetitive preparation of culture plates and hybridization filters may be carried out using equipment designed for working with this standard. Each individual cosmid clone in the collection possesses the innate mechanism of generating an RNA probe capable of detecting any overlapping or identical clones in the collection.

If an RNA probe is generated using T3 or T7 polymerase, and overlapping clones are detected by hybridization of the probe to a replica of the filter grid, using cosmid clones arranged on a 36×36 matrix containing 1296 clones, all of the overlaps can be detected by carrying out 1296 T3 polymerase reactions, 1296 T7 reactions and subsequent hybridization reactions.

However, as an alternative to the individual analysis of cosmid clones for the detection of overlaps, simultaneous analysis of multiple cosmid clones in groups can be conducted, as described in U.S. Pat. No. 5,219,726. Accordingly, this preferred strategy allows the analysis of a collection of cosmid clones with far less effort than "fingerprinting" each of the clones selected individually.

The linked clones detected by the above method can then be grouped into contigs, either manually or, preferably, using appropriate computer programs. To confirm the correctness of the groupings, some of the contigs can be subjected to detailed restriction enzyme analysis, and the degree of physical overlap along with a physical map can be determined. To complete a physical genomic map, the above-outlined procedure can be repeated with as many clones as necessary, and the gaps between the contigs can be filled in, e.g. by traditional chromosome walking.

The method described hereinabove represents a special case of a more general sequence mapping strategy based on clone matrices of higher order, such as, for example, greater than or equal to 3 dimensions described in U.S. Pat. No. 5,219,726.

Further details of the invention are illustrated by the following, non-limiting examples.

EXAMPLES

Unless otherwise stated, the present invention was performed using standard procedures, as described, for example in Maniatis et al., *Molecular Cloning: A Laboratory Manual*, Cold Spring Harbor Laboratory Press, Cold Spring Harbor, New York, USA (1982); Sambrook et al., *Molecular Cloning: A Laboratory Manual* (2 ed.), Cold Spring Harbor Laboratory Press, Cold Spring Harbor, New York, USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987).

Cosmid vectors

Genomic libraries were constructed in cosmid vector sCOS-1 illustrated in FIG. 1. sCOS-1 was prepared from cosmid vectors pWE15 [see Evans et al., Methods in Enzymology 152:604 (1987)]; ATCC Accession No. 37503, American Type Culture Collection (ATCC), 12301 Parklawn Drive, Rockville, Md. 20852 USA] and pDVcos134 [a gift from J. Reese, in wide circulation among scientists]. pWE15 DNA was digested with ClaI and SalI, and the 6 kb ClaI-SalI restriction fragment, lacking the cos sequence was purified. Cosmid pDVcos134 was digested with ClaI and XhoI and a restriction fragment containing the duplicated cos region was purified on a low melting point agarose gel. The purified fragments were ligated using T4 DNA ligase and transformed into *E. coli* host strain DH5.

Other pWE plasmids suitable for genomic mapping according to the invention are disclosed in Evans et al., Methods in Enzymology, Supra. Cosmid vector pWE16 has been deposited with the American Type Culture Collection, and has been accorded ATCC No. 37524.

Cosmids sCOS-2 and sCOS-4 are derivatives of sCOS-1 where the cloning site has been altered to substitute other rare restriction sites for the NotI sites. Cosmid vector sCOS-2 was constructed by digesting sCOS-1 with EcoRI, and purifying the plasmid DNA away from the NotI-T3 promoter-BamHI-T7 promoter-NotI linker sequence by ethanol precipitation. A 30-nucleotide double-stranded synthetic oligomer with EcoRI coadhesive ends, containing NotI-T3 promoter-BamHI-T7 promoter-Sac2 sequences was added by linker-tailing [Lathe et al., DNA 3:173 (1984)]. sCOS-4 was constructed using a similar procedure adding a double-stranded synthetic oligonucleotide containing EcoRI coadhesive ends and a SfiI-T3 promoter-BamHI-T7 promoter-SfiI sequence.

Example 1
Cosmid Multiplex Analysis of Human Chromosome 11q

The cosmid vector sCOS-1 (FIG. 1) was used to prepare a genomic library from a somatic cell hybrid containing as its only human material DNA from the distal long arm of human chromosome 11, including 11q21-11qter, in a mouse background [Maslen et al., Genomics 2:66 (1988)]. The distal long arm of human chromosome 11 is of biological interest for a number of reasons. Like the major histocompatibility complex, the T cell receptor and immunoglobulin genes, and the IgK-CD8A-CD8B region of chromosome 2p12, human chromosome 11q23 contains a cluster of genes encoding proteins which are members of the immunoglobulin superfamily and are possibly important for cell-cell interactions in the immune and nervous systems including Thy-1, CD3, δ, epsilon, and N-CAM [Nguyen et al., J. Cell. Biol. 102:711 (1986)]. 11q23 is the location of genes in which defects may be responsible for ataxia telangiectasia [Gatti et al., Nature 336:577 (1988)] and other hereditary disorders including multiple endocrine neoplasia type I [Larsson et al., Nature 332:85 (1988)], diabetes analogous to the NOD mouse [Prochazka et al., Science 237:286 (1987)] and others are also likely linked to markers on leukemias and pathognomonic for Ewing's sarcoma, peripheral neuroepithelioma and Askin's tumor [Griffin et al., Proc. Natl. Acad. Sci. USA 83:6122 (1986)]. The initial physical analysis of human chromosome 11 should allow eventual analysis of the genes associated with these phenomena and the underlying biology.

A genomic library consisting of $1.2 \times 10^7$ individual members was prepared and cosmids containing only human DNA were selected from this library by screening with probes recognizing human repetitive sequences. The proportion of human clones in this genomic library was 0.9%, indicating that the proportion of human chromosome 11 present in the somatic cell hybrid was about 27 mb, consistent with previous cytogenic and molecular characterization of this cell line [Maslen et al., Supra]. 1296 clones were selected, archived in 96-well microtitre plates, and arranged on a nitrocellulose filter according to the columns and rows of a 36×36 matrix. Using probes recognizing many available DNA markers mapping to this chromosome, cosmids containing the genes THY1 [van Rijs et al., Proc. Natl. Acad. Sci. USA 2:5832 (1985)], T3D, T3E [Evans et al., Immunogen 28:365 (1988)], ETS1 [Watson et al., Proc. Natl. Acad. Sci. USA 83:1792 (1986)], PBG [Wang et al., Proc. Natl. Acad. Sci. USA 78:5734 (1981)], PGR [Misrahi et al., Biochem. Biophys. Res. Commun. 143:740 (1987)], SRPR [Lauffer et al., Nature 318:334 (1985)], and APOA1 [Karathanasis et al., Proc. Natl. Acad. Sci. USA 80:6147 (1983)]. The identified genes and clone coordinates for DNA markers on human chromosome 11q-11qter represented in the ordered cosmid set are shown in Table 1.

TABLE 1

Identified genes and clone coordinates for DNA markers on human chromosome 11q21 - 11qter represented in the ordered cosmid set.

| cosmid clone coordinate (Y, X) | marker |
| --- | --- |
| 3, 11 | THY1 |
| 11, 34 | THY1 |
| 10, 7 | T3D (CD3γ, δ) |
| 7, 13 | ETS1 |
| 5, 13 | ETS1 |
| 4, 22 | PGR |
| 13, 27 | APOA1 |
| 11, 25 | PBGD |
| 12, 19 | D11S23 |
| 24, 12 | D11S24 |
| 24, 8 | SRPR |
| 11, 31 | SRPR |

Additional available RFLP markers [Maslen et al., Supra] were also identified in this collection to allow eventual correlation of the emerging physical map of chromosome 11 with the linkage map.

Groups of clones corresponding to 32 of the rows and 36 columns were pooled, and 68 hybridization reactions were carried out to replica filters according to the strategy outlined hereinbefore. Mixed probes detected a minimum of nine and a maximum of 46 cross-hybridizing unique clones on the filter matrix with each hybridization reaction using a pooled probe. When hybridization is carried out with a mixed probe consisting of RNA transcripts from cosmids of a row of the matrix, and a mixed probe representing a pool of all cosmids aligned along a column of the matrix, the cosmid clone which hybridizes with both mixed probes is linked to the clone located at the intersection of the row and column from which probe mixtures were prepared. To aid in the analysis of the data generated by this procedure, the Y and X coordinates of the cross-hybridizing clones are entered into a computer and matches identified using one of several computer programs. From this series of experiments, 1099 linked clones were detected from the hybridization of 36 pooled columns and 32 pooled rows of the matrix. Several of these overlapping clones were analyzed by restriction mapping to confirm that the clones indeed did overlap in the expected manner.

Completeness of the Cosmid Multiplex Data

From the list of linked clones produced by this multiplex technique, contigs were assembled either manually or through computer analysis of the data from the predicted hybridization linkage using mixed multiple RNA probes. Based on an initial analysis of the data using a simple algorithm for contig construction, 315 contigs were assembled from the 1099 linked clones determined from multiplex analysis. The size of the contigs ranged from 2 linked cosmids to 27 cosmids grouped into a contig extending over several hundred kb, with the majority of contigs consisting of between 2 and 5 cosmids. To confirm that these groupings reflected the true structure of the human chromosome, and not artifactual groupings due to random cross-hybridization, several of the contigs were restriction mapped in detail to determine the degree of overlap and establish a physical map. The restriction map of a representative contig assembled by this strategy is shown in FIG. 3.

Assessment of Progress

Based on the assumption that the region of human chromosome 11 carried by the parent hybrid represents about 27 mb, the collection of 1296 cosmid clones analyzed here represents about 2 genome equivalents. It is also estimated that the minimal detectable overlap by hybridization analysis using end-specific RNA probes is about 200 nucleotides. If $\Theta$ is the fraction of length of two clones which must be shared in order for overlap to be detected [Lander et al., Supra], then the expected number of contigs consisting of at least two clones generated by the analysis of N cosmid clones is $$Ne^{-c(1-\Theta)} - Ne^{-2c(1-\Theta)}$$

wherein the redundancy of coverage, $c = LN/G$, where L is the length of the clone insert and G is the haploid genome length in base pairs.

The minimum detectable overlap with end-specific RNA probes is $\Theta = 0.005$. Approaching the theoretical limit of $\Theta = 0$, a maximum of about 450 contigs would be expected to result after the analysis of one genome equivalent and about 260 contigs after the analysis of 2 genome equivalents. Thus the analysis of the clone set carried out here, generating 315 contigs after the analysis of about two genome equivalents, is in good agreement with theoretical predictions. The main advantage of the current strategy is that the analysis of 1296 clones required only 72 analytical reactions, rather than 1296.

It was found that the prehybridization of the RNA probes with a high concentration of human repetitive sequences, as hereinabove described, was sufficient to completely block hybridization of most of these frequencies, and was sufficient for eliminating most of these artifactual linkages. However, the analysis of several large contigs mapping to human chromosome 11 generated by this analysis has revealed several cosmid clones which were included in a contig but which could not be substantiated based on the result of restriction mapping and hybridization analysis. This artifact may be the result of cryptic low-frequency repetitive or redundant sequences present in this region of the genome, or could be the result of genomic sequences which are unstable and deleted or rearrange when cloned in E. coli. Evidence for the later sequences, isolated through screening non-amplified cosmid libraries, has been found in the analysis of the human CD3 locus [Evans et al., Immunogen, Supra]. However, it should be noted that the multiplex technique of the present invention, when carried to completion using both T3 and T7 mixed RNA probes, generates data that is internally redundant in that both members of a linked pair should cross-hybridize with one another. Thus, further refinement of this approach should eliminate most serious artifacts arising during multiplex clone analysis.

In this regard, the analysis disclosed in the present invention has generated a partially overlapping cosmid set which is estimated to include about 60% of the 11q21-11qter region of human chromosome 11q. The results of certain preliminary restriction enzyme analyses, further analysis of contigs and filling-in by traditional chromosome walking are in complete agreement with theoretical calculations of fingerprinting efficiency. A more complete analysis of this and other chromosome regions using a number of cosmids for 4 or more genome equivalents would be expected to result in near closure of the map. Using the technique of the present invention, this would require a collection of about 3600 cosmids and 120 T3 or T7 reactions/hybridizations rather than the 72 carried out in the present Example. In addition, the technique of the present invention is applicable for traditional chromosome "walking" to allow "filling-in" of gaps in a near complete map.

Additional analysis of this cosmid set representing chromosome 11q can be completed by automated restriction mapping. Analysis to date has revealed the presence of 177 potential "linking" clones, containing one or more NotI restriction sites, and 77 clones containing Sac2 sites indicative of hypomethylated CpG-rich islands. Forty of these cosmid clones contain clustered rare CpG rich restriction sites and can be identified unequivocally as hypomethylated islands. In addition, cosmid clones have recently proved very useful for in situ hybridization to metaphase or interphase chromosomes [Lichter et al., Proc. Natl. Acad. Sci. USA 85:9664 (1988)] and the identification of the cytogenic location of single-copy DNA sequences. These procedures potentially will allow ordering cosmid contigs with resolution of greater than 500 kb and, coupled with the strategy described here, provide a powerful mechanism for the constructions of physical maps of chromosomes.

Still further analysis of this cosmid set representing chromosome 11 can be carried out by direct automated DNA sequencing of the fragment ends as described above in the Detailed Description and in Examples 2 and 3.

Example 2

Sequence-Sampled Map of G. lamblia genome

A 10.5 mb genome of *Giardia lamblia* (Fan et al., 1991, *Nucleic Acids Res*, 19:1905–1908) was cloned as a twenty-genome equivalent cosmid library. Five thousand cosmids can be mapped, end-oriented and end-sequenced generating 10000 ordered sequence fragments spaced, on average, every one kilobase. The determination of 500 bp of DNA sequence directly from each cosmid end results in an average spacing between islands of 0.5 kb.

Cosmid clones

A *Giardia lamblia* cosmid library was constructed in vector sCos-1. The library was prepared by partially digesting WB strain Giardia lamblia genomic DNA with Sau3A and cloning the digestion products into the Bam HI site. From primary platings, 6,250 clones, representing about 20× coverage were picked and individually archived in 96-well microtitre plates and stored as frozen glycerol stocks. Clone names are derived from the library designation (GR) followed by the plate number and well position (e.g., cGR-2b11 denotes a cosmid located on plate 2 in well b11). These were arrayed onto filters with a Biomek 1000 robot (Beckman Instruments, Fullerton, Calif.) and the DNA fixed onto the filters using well known methods for analysis by hybridization. A specific hybridization probe to the β-giardin region was used to detect sixteen overlapping cosmids and a random probe detected another 26 overlapping cosmids. These cosmids were subjected to a series of mapping and sequencing experiments.

Automated DNA sample preparation

Template cosmid DNA was prepared by an alkaline lysis procedure (Sambrook et al., supra), or by using one of several DNA prep robots. Automated procedures used DNA prepared by an Autogen 540 DNA preparation robot (cycle 411), which was subsequently digested for one hour with RNAse A (75 μg/ul) in a total volume of 23 μl, and then precipitated with ethanol. Overnight growth of cosmid clones in 5 mls of terrific broth (see, Sambrook et al., supra) with 10 μg/ml kanamyacin generally provided sufficient DNA for one or two sequencing reactions.

Automated DNA sequencing

DNA sequencing was carried out using primers complementary to the T3 or T7 polymerase promoter located in the cos-mid vector flanking the insertion site. Template cosmid DNA was prepared by an Autogen 540 DNA preparation robot (cycle 411). Automated sequencing reactions were carried out using dye labeled T3 or T7 oligonucleotide primers with reactions assembled and cycle sequenced using the Applied Biosystems (ABI, Foster City, Calif.) Catalyst 800 robot with DNA concentrations of ~0.2 μg/μl. Sequence determination was carried out using the ABI 373A fluorescent sequencer. The labels (names) given to each of the DNA sequences determined from the cosmid clones are the clone names followed by -t or -u, denoting sequences from the T3 or T7 priming sites, respectively (e.g., cGR-19a9-u is the sequence of the T7 end of the cosmid clone found on plate 19 in position A9 in the GR library). The increased organization permitted by the new nomenclature system used in Examples 2 and 3 will facilitate the large scale physical mapping strategies described herein.

Contig construction and physical mapping

Identification of cosmids from the β-giardin genomic region was accomplished using filters representing five-fold of the twenty-fold genomic library. Bacterial clones were stamped into a grid pattern with a Biomek 1000 robot using S & S Nytran filters with a 0.4 μm pore size and fixed to the filters using standard fixation procedures. A probe of approximately 1 kb recognizing β-giardin genomic DNA was generated by PCR with the oligonucleotides GGT-CAAGCTCAGCAACATGA (SEQ ID NO:741) and TGCTTTGTGACCATCGAGAG (SEQ ID NO:742) with standard amplification conditions and an annealing temperature of 60° C. Similarly, a random probe was generated as a 1.5 kb product with the primers CAGCAGATGGTCAAG-CAAAA (SEQ ID NO:743) and ACTCCTGACACCAC-CACCTC (SEQ ID NO:744).

Physical and sequence maps were constructed by full digestion of each cosmid with the restriction enzymes NcoI and BglII. Restriction fragments were separated on a 0.4% high strength agarose gel (0.5× TBE; see Sambrook et al., supra) run for 24 hours at 22 v in a 20 by 20 cm gel apparatus. The NcoI and BglII restriction enzymes digest the vector opposite the cloning site generating genomic fragments. Each end of the genomic insert was detected as a vector/genomic chimera by hybridization with probes flanking the T3 and T7 promoter sites of sCos-1. The 1046 bp t3 probe was amplified from sCos-1 with the primers (5' to 3') TCGCTCACTGACTCGCTG (SEQ ID NO:745) and AGC-CCTCCCGTATCGTAGTT (SEQ ID NO:746), and the 1004 bp T7 probe with the primers CTTGAGAGCCTTCAAC-CCAG (SEQ ID NO:747) and AACTGGGCGGAGT-TAGGG (SEQ ID NO:797) with an annealing temperature of 60° C. and the standard conditions described above. The T7 probe was labeled by random priming with $^{35}$S dATP and the t3 probe with $^{33}$P dATP for dual-label hybridizations. Maps were constructed by determining an order of fragments with no gaps with the gram program [see, e.g., Soderlund et al., in *Proceedings of the 26th Hawaii International Conference on System Sciences: Biotechnology Computing.* (ed. Hunter, L.) 620–630 (CA: IEEE Computer Society Press, 1993)].

The mapping strategy consisted of digesting each cosmid with two different restriction enzymes and precisely determining the number and sizes of the various products. The enzymes NcoI and BglII were chosen for mapping because their recognition sites have different numbers of G/C bases and their sites are located several kb from the vector cloning site. Fragment sizes were estimated with the GelReader program of T. Redman (National Center for Supercomputer Applications, Urbana, Ill.) and maps constructed with a modified version of GRAM, which takes the end fragments into account. Maps of oriented cosmids were generated by comparison of the two maps of restriction fragments (FIG. 4). The ends were placed by fit relative to the neighboring sites for 32 of the 42 cosmids while the remaining ten were determined by the concordance of the possible orientations of ends on both enzyme maps using neighboring known cosmid ends as anchors. One 11h4 was equivocal and the FASTA analysis of the derived sequences showed that the t7 end matched the reverse complement of the 25h9 t3 sequence.

Sequence Analysis

The presence of repetitive sequences was determined using the program FASTA which compares all sequences to those previously determined supplemented with a comprehensive set of di- and tri-nucleotide repeats. A FASTA cutoff score of 1000 was used to recognize repetitive sequences from background random matches. Similarities to known genes were identified with the BLAST program and the GenBank database. Amino acid comparisons were performed by translating DNA sequence fragments into all six potential reading frames and comparing translations to protein sequences in the non-redundant Swiss-Prot, GenPept or PIR database of the National Center for Biotechnology Information (Bethesda, Md.) using the program BLASTX. The results of these various searches were evaluated numerically and by inspection (see, e.g., Table 2). The data associated with this project, including DNA sequence file pointers, matches from sequence analysis and information about overlapping clones, were stored in a relational database. The sequences generated by automated fluorescent sequencing from cosmid ends have been deposited with GenBank and were not edited to remove unidentified bases or correct the sequence.

TABLE 2

Sequence searches performed with BLAST which produced likely, possible and interesting similarities to known sequences[a] with the sources of sequences, scores, percent identical residues and the length of amino acids matched. The highest scoring BLAST match is shown when more than one region or protein was similar to the unknown sequence.

| sequence | similar to: | score | % ID | length |
|---|---|---|---|---|
| Likely | | | | |
| cGR-38b8-t[a] | DNA similar to 3' noncoding region surface antigen gene, *G. lamblia* (gb:L11331) | 761 | 100 | 154 |
| cGR-45h5-u | protein kinase nek1, mouse (gb:S45828) | 189 | 58 | 58 |
| cGR-41e11-u | VSP1267 surface antigen, *G. lamblia* (sp:TSA4_GIALA) | 189 | 58 | 60 |
| cGR-62e12-u | protein kinase nek1, mouse. (gb:S45828) | 170 | 44 | 75 |
| cGR-15c7-t[b] | G2 specific protein kinase, *A. nidulans* (sp:NIMA_ASPNI) | 95 | 36 | 50 |
| cGR-45h5-t | surface protein 11, *G. lamblia* (gb:M95814) | 75 | 33 | 48 |
| Possible | | | | |
| cGR-16g10-u | transcription factor Oct-1, mouse (sp:HMO1_MOUSE) | 74 | 34 | 58 |
| cGR-15c7-u | MYB Protooncogene protein, *D. discoidium* (gb:S93742) | 74 | 40 | 37 |
| Interesting | | | | |
| cGR-51a9-u | eukaryotic initiation factor 4E, mouse (sp1F4E_MOUSE) | 70 | 32 | 62 |
| cGR-19d7-t | polyposis coli protein DP1, human (gb:M73547) | 69 | 38 | 42 |
| cGR-57a10-u | ribonuclease inhibitor, rat (sp:RIN1_RAT) | 66 | 42 | 45 |
| cGR-22b8-t | dynein associated (glued) protein, *D. melanorgaster* (sp:DY15_DROME) | 66 | 46 | 28 |
| cGR-25h9-t | cosmid F09G8, *C. elegans* (gb:L11247) | 66 | 27 | 51 |
| cGR-2g8-u | ORF in thr4-sup61 intergenic region, *S. cerevisiae* (sp:YCV0_YEAST) | 64 | 32 | 31 |
| cGR-19g10-u | M5 protein precursor, *S. pyogenes* (sp:M5_STRPY) | 63 | 29 | 54 |
| cGR-16g8-u | zinc finger proteins, *X. laevis* (pir: S06546) | 62 | 57 | 21 |
| cGR-16g10-t | lamin B2, chicken (sp:LAM2_CHICK) | 60 | 30 | 30 |
| cGR-41f7-u | ankyrin 2, brain, human (pir:S14569) | 57 | 33 | 54 |

[a]Searches presented were protein sequence based with the exception of an identical nucleotide sequence found for cGR-38b89-t.
[b]The overlapping sequence determined from cGR-15c7-t and cGR-6a6-u were searched together as one Sequences derived from cosmid ends were analyzed for the presence of repetitive sequences, simple sequence repeats and similarities to known genes (FIG. 5). A number of genes were detected in our characterization of sequences from this project. There were three protein kinases and a surface antigen gene in the random genetic region; no additional genes were detected near the β-giardin gene. Additional genes could likely be determined with gene prediction programs developed for these applications such as GRAIL.

Computer-aided primer pair design.

One advantage of mapping and sequence sampling is future independence from clone libraries through PCR amplification was tested within the random region contig. The selection of primer pairs for PCR analysis was carried out using the PRIMER program provided by E. Lander (MIT) for each of the cosmid-derived end-sequences that were determined. Analysis was done in batch processing mode on a Sun workstation specifying an annealing temperature of 60° C. and a primer length of 18–22 nt. Modifications of these parameters, (oligonucleotide length 25 nt and annealing temperatures 55° C. for AT-rich sequences and annealing temperatures to 65° C. or greater for GC-rich sequences) generally allowed production of a suitable primer. Primers were produced commercially by Genset, Inc. (Paris, France).

Predicted STS primers were tested by PCR amplification in a 30 μl reaction volume containing: 10 mM Tris (pH 8.8), 50 mM KCl, 1.5 mM $MgCl_2$, 0.001% gelatin, 200 μM each dNTP, 100 ng genomic DNA and 1.5 units of Taq DNA polymerase. Initial PCR conditions were: denaturation at 93° C. for 2 minutes; 35 cycles of 30 seconds each at 94° C., annealing for one minute at the predicted annealing temperature, and 30 seconds at 72° C.; followed by a final extension at 72° C. for five minutes. The probes were labeled by random priming with a $^{32}p$ dCTP and sCos-1 DNA was labeled with $^{35}S$ dATP to identify specific clones in the hybridization process.

The ordered sequences were then checked by PCR amplification demonstrating amplification of a specific region of interest independent of the cosmid libraries. Products were obtained for most (>85%) of the neighboring sequences. Some failures, possibly due to incorrect primer sequences and large distances between primers were not analyzed further within the random contig region.

In summary, two regions of the *Giardia lamblia* genome were mapped and sequences sampled from within those areas of approximately 160 kb (FIG. 4A–4B). The sequenced cosmid ends encompass approximately 15% of this total region. The average sequence read was 347 bp which does not differ from the median (353 bp) and has a standard deviation of 39 bp. Eight cases of cosmids ending at exactly the same Sau3A sites were observed and in four cases cosmid ends were close enough to one another to form small sequence contigs. Overall, the median spacing between cosmid ends was 1.25 kb with an average spacing of 2.0 kb suggesting that the relatively rare events of cloning from defined restriction sites follows a poisson process suggested by visual inspection of FIG. 6. These are underestimates of sequence overlaps and identical ends since cosmids which intrude into the contig without encompassing the region detected with the hybridization probe were not included in the contig. Full characterization of the region would nearly double the amount sequenced to approximately 30%. The large number of identical ends compared to overlapping sequence contigs suggests that the practical limit for constructing a library with one restriction enzyme for partial digests is below twenty fold and perhaps as low as five to ten fold in the sequence sampling strategy.

Example 3

Preparation of a Chromosome-11 Sequence Sampled Map

Cosmid libraries

Two chromosome 11-specific cosmid libraries were constructed in vector sCos-1. Cosmids denoted 11q were isolated from a library prepared from hybrid TG5D1-1 representing chromosome 11q13-11qter (Evans and Lewis, 1989, *Proc. Natl. Acad. Sci., USA*, 86:5030–5034). Cosmids denoted SRL were isolated from a flow sorted chromosome 11-specific library prepared from somatic cell hybrid J1 (described in Kao et al., 1977, *Somatic. Cell. Genet.*, 3:421–429). The SRL library was prepared from 100 ng of flow purified chromosome 11 at the Los Alamos National Laboratory (L. Deaven and J. Longmire) as part of the National Gene Library Project and represented 125× coverage of chromosome 11. Approximately 17,000 clones, representing about 5× coverage, were picked from primary platings and individually archived in 96-well microtitre plates for use in this example. Characterization of this library revealed that about 4% consist of non-human inserts. Clone names are derived from the library designation followed by the plate number and well position (e.g., c11q-2b11 denotes a cosmid from the c11q cosmid library located on plate 2 in well b11).

Cosmid end sequencing

To generate sequence data from the cosmids, DNA sequencing was carried out using primers complementary to the T3 or T7 polymerase promoter located in the cosmid vector flanking the insertion site. Template cosmid DNA was prepared by an alkaline lysis procedure (Sambrook et al., supra), or by using one of several DNA prep robots. Automated procedures used DNA prepared by an Autogen 540 DNA preparation robot (cycle 411), which was subsequently digested for one hour with RNAse A (75 µg/µl) in a total volume of 23 µl, and then precipitated with ethanol. Overnight growth of cosmid clones in 5 mls of terrific broth (Sambrook et al., supra) with 10 ug/ml kanamyacin generally provided sufficient DNA for one or two sequencing reactions. Alternatively, DNA template preparations were done using the custom "Prepper, Ph.D."DNA preparation robot developed by H. R. Garner (Garner et al., *Sci. Computing and Automation*, March/1993, 61–68). Some of the initial sequences in this example were determined manually using Sequenase kits with dideoxy terminators (U.S. Biochemicals).

Automated sequencing reactions were carried out using dye labeled T3 or T7 oligonucleotide primers with reactions assembled and cycle sequenced using the Applied Biosystems (ABI) Catalyst 800 robot with DNA concentrations of ~0.2 µg/µl. Automated DNA sequencing was carried out using the ABI 373A sequencer. The names of DNA sequences determined from the cosmid clones are the clone names followed by -t or -u, denoting sequences from the t3 or t7 priming sites, respectively. (e.g., c11q-2b11-u is the sequence of the t7 end of cosmid 2b11 from library 11q).

A sample of 371 DNA sequence fragments were determined by automated sequencing from cosmid ends. Forty-nine sequences were not used for STS production in this example and were placed in reserve should additional STSs be needed. Extensive regions of repetitive sequence which made PCR primer prediction unlikely occurred in 14% (45/322) of those analyzed (Table 3). The remaining 277 sequences (86%) were used for STS primer prediction by computer analysis and oligonucleotide primers were synthesized and tested.

STS MAP OF CHROMOSOME 11

TABLE 3

Analysis of 322 cosmid-derived sequences for STS production

| Fate of sequences | number | percentage of total |
|---|---|---|
| Not suitable for primer prediction | 45 | 14% |
| failed STS production | 65 | 20% |
| successful STSs production | 212 | 66% |
| STSs mapped to a region | 187 | 58% |

Note: Cosmid sequences were determined by direct priming of cosmid templates using oligonucleotides complementary to the T3 or T7 polymerase promoters present in the vector. STS primers were predicted using the PRIMER program.

The sequences generated by automated fluorescent sequencing from cosmid ends have been deposited with GenBank and were not edited to remove unidentified bases or correct the sequence. The sequence information was not corrected before analysis so that the Primer program would not predict primers in regions of questionable accuracy. Consequently, some of the alignments showing similarity between known protein sequences and translated chromosome 11 specific sequences contain Xs at unknown and stop codons which could be due to errors in the sequence or translating beyond exons into introns.

Computer-aided primer pair design

The selection of primer pairs for STS analysis was carried out using the Primer program available from E. Lander (MIT). Analysis was done in batch processing mode on a Sun workstation specifying an annealing temperature of 60° C. and a primer length of 18–22 nt. Modifications of these parameters, (oligonucleotide length 25 nt and annealing temperatures 55° C. for AT-rich sequences and annealing temperatures to 65° C. or greater for GC-rich sequences) generally allowed production of a suitable primer set. DNA sequences that contained extensive regions of repetitive sequence so that primers could not be designed to generate products of at least 120 bp were not utilized. Primers were synthesized using an ABI PCR-Mate oligonucleotide synthesizer or produced commercially by Genset, Inc. (Paris, France).

Of this collection of primers, 77% (212/277) generated PCR amplification products from human genomic DNA and J1 hybrid DNA without producing products from yeast genomic DNA and are suitable for STS content mapping using YAC libraries. Localization of 88% of these new STS markers (188/212) was carried out by hybrid analysis, FISH or a combination of both. For comparison, nearly the same success rate occurred in predicting primer sets from sequences retrieved from GenBank. In some cases primer sets derived from the cSRL library which failed to amplify human DNA clearly generated a product from hamster—the J1 cell line host (Table 4).

TABLE 4

STS MAP OF CHROMOSOME 11
Hybrid cell lines containing specific regions of human chromosome 11

| Cell line | chromosome 11 region | | species | reference |
|---|---|---|---|---|
| | cytogenetic | .flpter | | |
| J1 | p15.5-q25 | 0–1 | hamster | Kao, et al., 1977 |
| CH66-36 | p15.5-q24.1 | 0–0.93 | hamster | G. Hermanson and M. Altherr (unpub. data) |

TABLE 4-continued

STS MAP OF CHROMOSOME 11
Hybrid cell lines containing specific regions of human chromosome 11 chromosome 11 region

| Cell line | cytogenetic | .flpter | species | reference |
|---|---|---|---|---|
| ALE4 | p15.5-q23.3 | 0–0.85 | hamster | Delattre, et al., 1991 |
| MC-1 | p15.5-q23.3 | 0–0.85 | hamster | Glaser, et al., 1989 |
| MX-11 | p15.5-q23.3 | 0–0.85 | mouse | Junien, et al., 1992 |
| CY.8 | p15.5-q14.1 | 0–0.6 | mouse | D. Callen (pers. comm.) |
| 16TX2 | p15.5-p11.2 | 0–0.33 | mouse | Junien, et al., 1992 |
| CH66-23 | q24.1-q25 | 0.93–1 | hamster | G. Hermanson and M. Altherr (unpub. data) |
| R28/4D | q13.1-q25 | 0.5–1 | hamster | Glaser, et al., 1989 |
| CF52-46 | q13.1-q25 | 0.5–1 | mouse | Junien, et al., 1992 |
| POR4 | p13.1-q25 | 0.24–1 | mouse | Junien, et al., 1992 |
| PEL 16 | p15.4-425 | 0.05–1 | mouse | Junien, et al., 1992 |

Note: The species from which cell lines were derived and a reference is indicatred above.

STS markers generated from mapped cosmids were supplemented with STSs corresponding to almost all of the cloned genes on chromosome 11 to allow for eventual production of a complete chromosome map. Genes mapped to chromosome 11 were identified by searching the Genome Data Base (GDB; Pearson et al, 1992, *Nucleic Acids Res.*, 20:2201–2206), On-line Mendelian Inheritance in Man (OMIM), GenBank, Medline, and the like. The DNA sequences were retrieved from GenBank when available and STS primers designed using PRIMER. Whenever possible, chromosome 11 genomic DNA sequence was used for STS production and primer pairs were designed to generate products of 400 to 1000 base pairs. When genomic DNA sequence was not available, the generally intron-free 3' untranslated region of chromosome 11 cDNAs was chosen. Where these were not available, cDNA coding regions were utilized and the predicted amplification product sizes were limited to 150–250 bp in order to minimize the chances of including an intron in the target region. In the overall design of STS primer sets, predicted product lengths were intentionally varied over the range 150 to 1000 bp to allow for eventual multiplex screening of YAC libraries.

Characterization of chromosome 11-specific STSs

Predicted STS primers were tested by PCR amplification (Saiki et al., 1988, *Science*, 239:487–491) in a 30 $\mu$l reaction volume containing: 10 mM Tris (pH 8.8), 50 mM KCl, 1.5 mM MgCl2, 0.001% gelatin, 200 $\mu$M each dNTP, 100 ng template DNA and 1.5 units of Taq DNA polymerase. Initial PCR conditions were: denaturation at 93° C. for 2 minutes; 35 cycles of 30 seconds each at 94° C., annealing for one minute at the predicted annealing temperature, and 30 seconds at 72° C.; followed by a final extension at 72° C. for five minutes. Initially, three different concentrations of primers (833, 500 and 250 nM) were tested for amplification using human genomic DNA. An optimal concentration and temperature were determined for the amplification of the following test DNA samples: human genomic DNA, DNA from the hybrid cell line J1 containing human chromosome 11 in a CHO cell background, hamster genomic DNA, mouse genomic DNA and yeast DNA. Those primer sets that produced an amplification product of the expected size from human genomic DNA and J1 DNA were characterized further. Most of the STSs generated have a narrow range of annealing temperatures from 56° C. to 60° C. and relatively short primer lengths of around 20 nucleotides.

Physical Mapping by fluorescence in situ hybridization (FISH)

To map the genomic location of each STS, in situ hybridization using cosmid DNA was carried out on metaphases prepared from human fibroblasts (CRL1634; Human Genetic Mutant Cell Repository, Camden, N.J.) using well-known methods (see, e.g., Giovannini et al., 1993, *Cytogenet. Cell. Genet.*, 63:62). Chromosomal localization was determined as chromosome 11 FLpter (fractional chromosomal length from 11pter) and cytogenetic band position was extrapolated from the coincidence of FLpter values to cytogenetic bands on the chromosome ideogram.

Somatic cell hybrid analysis

Additional localization of some cosmid sequences, and localization of STSs produced from gene sequences, were carried out using a panel of hybrid cell lines set forth in Table 4 containing part or all of human chromosome 11 in mouse or hamster genomic backgrounds. Analyses of the PCR amplification of STSs from DNA isolated from this set of hybrids mapped the STSs to eight distinct regions, or bins, on chromosome 11 (FIG. 8).

The whole set of 370 STS markers, associated with known genes or chromosome-specific cosmid clones, was regionally mapped to chromosome 11. The STS markers are shown in Table 5, in sequential order corresponding to SEQ ID NOs: 1–740. Some of the map locations of these cosmids had been reported previously, though not associated with STS identifiers of the present invention. Of the 370 STSs generated, 335 were successfully mapped to specific regions of human chromosome 11 (Table 5) using FISH or through the PCR analysis of a somatic cell mapping panel. Mapping information for some markers was available from GDB and was confirmed in this study based upon hybrid analysis. Consistent results were found in all cases when mapping information on many markers was determined using both FISH and hybrid analysis.

In general, the set of standard STSs derived in this example appear to be uniformly distributed throughout the chromosome and include markers for most of the significant mapping landmarks. Chromosome 11 was divided into twenty regions and the average distribution of STSs along chromosome 11 was assessed. The average number of STSs per region was 17 with a standard deviation of 4.5. The most over-represented region was FLpter 0.85 to 1 (11q23.3-q25) while 0.3 to 0.45 (11p12-q12.1) and 0.6 to 0.85 (11q14.1-q23.2) contained proportionally fewer STSs. The relative precision of the mapping information can be estimated from the distribution of FLpter ranges of the 335 mapped STSs. Twenty-four percent of the markers had an FLpter range of less than 0.05, 55% less than 0.1 and 83% less than 0.2.

TABLE 5

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| D11S1002 | c11q-1a7 | 0.50–0.60 11q13.1–q14.1 | b | 176 | c11q-1a7-tA<br>c11q-1a7-tZ | TCTGTCTGGAAGAGCGTGG<br>CCAGACCAAGTCTTGGACCT | 250<br>250 | 56 |
| D11S493 | c11q-1d7 | 0.56–0.64 11q13.5–q14.2 | c | 194 | c11q-1d7-tA<br>c11q-1d7-tZ | CCATAAATGAAAGGTTTGGATG<br>GCGACTTGAGCTGTCATGC | 250<br>250 | 56 |
| D11S360 | c11q-1f6 | 0.62–0.66 11q14.1–q14.3 | a | 252 | c11q-1f6-tA<br>c11q-1f6-tZ | TGGCATTATAGGTGCCCG<br>CTCAGGAAACAGGGAGATGC | 250<br>250 | 66 |
| D11S366 | c11q-2b11 | 0.86–0.89 11q23.3 | ab | 183 | c11q-2b11-tA<br>c11q-2b11-tZ | CCAGGAAGGGTTCCCTGAAGTAGGTG<br>ATAAGCTGCTGCTACCTACAGCTGCC | 250<br>250 | 56 |
| D11S361 | c11q-2c4 | 0.70–0.72 11q21–q22.1 | ab | 189 | c11q-2c4-tA<br>c11q-2c4-tZ | AGAAAACTGATTAACCAAGGCA<br>AGCAAATCTCGTCTCAAAAAAA | 833<br>833 | 56 |
| D11S353 | c11q-2d4 | 0.55–0.58 11q13.3–q13.5 | ab | 150 | c11q-2d4-uB<br>c11q-2d4-uX | TCCAGTAGGAAGAGATGCAGG<br>GGATTCCTTCTACTCTCCCAGG | 250<br>250 | 56 |
| D11S356 | c11q-2g9 | 0.56–0.59 11q13.4–q13.5 | abc | 183 | c11q-2g9-tA<br>c11q-2g9-tZ | AGCTGTGGGTTCATAATGGC<br>AGGTGAAGAGGAGGAGAGTGC | 833<br>833 | 82 |
| D11S491 | c11q-3c3 | 0.56–0.59 11q13.5 | b | 138 | c11q-3c3-uA<br>c11q-3c3-uZ | CCTGTGGCCTCCTATGACAT<br>TGAGGCCTCTCTTCTCTCATG | 833<br>833 | 56 |
| D11S794 | c11q-3f11 | 0.92–0.92 11q24.1 | a | 154 | c11q-3f11-uA<br>c11q-3f11-uZ | CTTGGGAGTCACTGAACTGATG<br>CCCACATCCCTAAACTGGAA | 250<br>250 | 56 |
| D11S1004 | c11q-3h11 | 0.85–0.85 11q23.3 | b | 170 | c11q-3h11-uA<br>c11q-3h11-uZ | AGGAAACTGAGGAACAGAGCA<br>GGCTGGCCTGGAGTTAACTA | 833<br>833 | 55 |
| D11S528 | c11q-4e1 | 0.85–0.91 11q23.3 | bc | 177 | c11q-4e1-uS<br>c11q-4e1-uA | CTAGCATGTGAGGGTGTGGAGGT<br>AATCACACTCTTGGTGGGTTTTCG | 440<br>440 | 55 |
| D11S1005 | c11q-5c3 | 0.85–0.93 11q23.3–q24.1 | b | 101 | c11q-5c3-tB<br>c11q-5c3-tY | AACACCAACATCACAAAAGAAA<br>ACTGACAAGAGCTTGCTGCA | 250<br>250 | 58 |
| D11S795 | c11q-5e5 | 0.92–0.92 11q24.1 | a | 216 | c11q-5e5-tA<br>c11q-5e5-tZ | AGCACACCCGGTGGTATG<br>AGATGATGCCCTTCCCCC | 500<br>500 | 51 |
| D11S793 | c11q-5f9 | 0.86–0.83 11q23.3–q23.2 | bc | 256 | c11q-5f9-tA<br>c11q-5f9-tZ | GGTCCCCTCTAAGAAGCACC<br>CTTTTCCAAGTGCCAGCCT | 250<br>250 | 56 |
| D11S368 | c11q-6c10 | 0.86–0.89 11q23.3 | a | 257 | D11S368-A<br>c11q-6c10-uZ | TTATAGGCGCCTGCACCACGTCT<br>TCAAGAGGTTGAAGCAGTGAGCCGTG | 500<br>500 | 51 |
| D11S1006 | c11q-6h6 | 0.93–1.00 11q24.1–q25 | a | 228 | c11q-6h6-1A<br>c11q-6h6-1Z | CACCATGCAATCTGCAGC<br>ATTTCTGCCTGCTGATCCAT | 250<br>250 | 58 |
| D11S800 | c11q-7d4 | 0.59–0.68 11q14.1–q14.3 | b | 150 | c11q-7d4-uA<br>c11q-7d4-uZ | TAGGAACCCCCATCATTCCA<br>CCATGGAGGTCCCCTTTC | 833<br>833 | 52 |
| D11S492 | c11q-7h10 | 0.78–0.85 11q23.1–q23.3 | b | 161 | c11q-7h10-tA<br>c11q-7h10-tZ | AAGCTCTCTGGGAAATAAAGGG<br>AACAAACTCATGAATGCCTGG | 833<br>833 | 56 |
| D11S797 | c11q-7h8 | 0.85–0.91 11q23.3 | b | 207 | c11q-7h8-tA<br>c11q-7h8tZ | GTGTGGGGCCACTGTATTG<br>TGGCAACAAAAGCAAGACTG | 833<br>833 | 56 |
| D11S488 | c11q-8d1 | 0.91–1.00 11q24.1–q25 | a | 190 | c11q-8d1-tA<br>c11q-8d1-tZ | AAGGAAGGAAGGAACGAAAGG<br>CTGATAGCCTGACCTGACTGTG | 500<br>500 | 58 |
| D11S783 | c11q-8d10 | 0.94–1.00 11q25 | a | 230 | marco2s<br>marco2a | GGAGAGGACATTAACCAGCTGA<br>GTGATGGGTTGCATAGTGTCTG | 877<br>877 | 50 |
| D11S784 | c11q-8d11 | 0.94–1.00 11q25 | a | 154 | c11q-8d11-tA<br>c11q-8d11-tZ | GAGAGTGGAAGCAAAGGCTG<br>CTCCCTTCCTTACCCTACAACC | 250<br>250 | 58 |
| D11S1008 | c11q-8h4 | 0.60–0.85 11q14.1–23.3 | b | 265 | c11q-8h-4-tA<br>c11q-8h4-tZ | ACTGGGGACCCCATGACT<br>GGGCTCCTGCTCTACCTCTT | 500<br>500 | 56 |
| D11S1009 | c11q-9a1 | 0.94–1.00 11q25 | b | 250 | c11q-9a1-tA<br>c11q-9a1-tZ | ACTGTGTGGGGAGAAGGTACC<br>TGCTGGTAACTTACCACTGTGC | 500<br>250 | 56 |
| D11S1001 | c11q-10d7 | 0.85–0.93 11q23.3–24.1 | b | 244 | c11q-10d1-tA<br>c11q-10d1-tZ | CCACCATATCCTGCGAAATT<br>GGTTGCAAGATCACGTCACT | 250<br>250 | 65 |
| D11S1011 | cSRL-1a2 | 0.94–1.00 11q25 | a | 150 | cSRL-1a2-uA<br>cSRL-1a2-uZ | CAGCTTTACTTTTATTTACAGAGGTTT<br>CTAGAACTTCCTGGTTTAAACGAAA | 833<br>833 | 56 |
| D11S1010 | cSRL-1a12 | 0.46–0.48 11q12.3 | ab | 190 | cSRL-1a12-uA<br>cSRL-1a12-uZ | GCTTGCTGCAATGTTTTTCA<br>CTGGCTGCTAAAAGAAGAGACC | 833<br>833 | 56 |
| D11S1013 | cSRL-1b2 | 0.95–0.98 11q25 | ab | 175 | cSRL-1b2-uA<br>cSRL-1b2-uZ | GAGTTTGGAG.CAAGCCAGTC<br>TGACCTTGATGCTCACTTGG | 500<br>500 | 56 |
| D11S1014 | cSRL-1b4 | 0.61–0.61 11q14.1 | ab | 154 | cSRL-1b4-uA<br>cSRL-1b4-uZ | AAGTCACACAGCTAGCAAATGG<br>TGTCCTTGACGGAATAGATTCC | 250<br>250 | 58 |
| D11S1015 | cSRL-1b8 | 0.44–0.59 11q12.1–q13.5 | a | 201 | cSRL-1b8-uA<br>cSRL-1b8-uZ | GGTCAGGCCACACCTCAC<br>ATACCCTTCAGGTGGATCCC | 250<br>250 | 60 |
| D11S1012 | cSRL-1b11 | 0.40–0.55 11p11.11–q13.3 | a | 151 | cSRL-1b11-uA<br>cSRL-1b11-uZ | GCTGTCAGACTGAAGACCCTG<br>ACTGCCAGCCTGGTCAGAG | 833<br>833 | 58 |
| D11S1016 | cSRL-1c5 | 0.70–0.85 11q23.1–q23.3 | ab | 185 | cSRL-1c5-tA<br>cSRL-1c5-tZ | TTCAGCACTCCTTACATTGCC<br>TCCAACTGAAACAGCCTGC | 833<br>833 | 58 |
| D11S1017 | cSRL-1c8 | 0.93–0.93 11q24.1 | ab | 175 | cSRL-1c8-tA<br>cSRL-1c8-tZ | GCACTCCTGTCTTGGTCCAT<br>AGGGATCCATCTTGGAAGCT | 250<br>250 | 58 |
| D11S1018 | cSRL-1d4 | 0.24–0.33 11p13–p11.2 | b | 211 | cSRL-1d4-uA<br>cSRL-1d4-uZ | CCAAGGACAGGCAGTAGAGC<br>CAATGAAATGATGCAGTGTGG | 250<br>250 | 58 |
| D11S1019 | cSRL-1d5 | 0.05–0.24 | b | 141 | cSRL-1d5-uA | CCTCAGTCCTTTGCACTTG | 250 | 56 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | 11p15.4–p13 | | | cSRL-1d5-uZ | TCTGGCTATTTTGTACAGGG | 250 | |
| D11S1020 | cSRL-1d6 | 0.05–0.12 | ab | 241 | cSRL-1d6-tA | GCCCTCTAGTCATGCCACAT | 500 | 58 |
| | | 11p15.4–p15.1 | | | cSRL-1d6-tZ | ACGCGAAACCAGATCATTCT | 500 | |
| D11S1022 | cSRL-1f5 | 0.33–0.50 | b | 134 | cSRL-1f5-uB | CAACCAAAATAAAAGGCCTCC | 250 | 56 |
| | | 11p11.2–q13.1 | | | cSRL-1f5-uZ | GTGTTCTTCTCTTGCACCTGC | 250 | |
| D11S1023 | cSRL-1f8 | 0.85–0.93 | b | 215 | cSRL-1f8-uA | GCAGGTTTCAAGAAGGTATG | 833 | 58 |
| | | 11q23.3–q24.1 | | | cSRL-1f8-uZ | GGCAGCCATTTTCTTACCAA | 833 | |
| D11S1021 | cSRL-1f12 | 0.00–0.05 | b | 157 | cSRL-1f12-uA | CATGCAGGTGTCAGGACG | 833 | 57 |
| | | 11p15.5–p15.4 | | | cSRL-1f12-uZ | GATACCAGAGAGATTGCATCCC | 833 | |
| D11S1024 | cSRL-1g5 | nd | | 219 | cSRL-1g5-uB | GATGCCATGCTGGGTTAAAC | 833 | 52 |
| | | | | | cSRL-1g5-uY | TCATCTTAAGCCCATTCTCTCC | 833 | |
| D11S1025 | cSRL-1g8 | nd' | | 155 | cSRL-1g8-uB | CGACCCTGGGTGTTAACAAC | 833 | 54 |
| | | | | | cSRL-1g8-uY | AAAGGAACGTGTTACCGCTG | 833 | |
| D11S1026 | cSRL-1g9 | 0.60–0.85 | b | 151 | cSRL-1g9-uA | GTTGATGAGCCAGACAAAACTG | 833 | 56 |
| | | 11q14.1–q23.3 | | | cSRL-1g9-uZ | TATGCAGTGATGTTAGGTTTGC | 833 | |
| D11S1027 | cSRL-1h6 | 0.50–0.85 | b | 172 | cSRL-1h6-uA | GTCCAATACGGTAGCCACTAGC | 500 | 58 |
| | | 11q13.1–q23.3 | | | cSRL-1h6-uZ | CGATCTAGAGCTGTGCTGTCC | 500 | |
| D11S1028 | cSRL-1unk | 0.50–0.85 | b | 155 | cSRL-1h10-uA | CCCAAGACTAACAAGGCCTC | 833 | 58 |
| | | 11q13.1–q23.3 | | | cSRL-1h10-uZ | GAAACATTGCATATCCTGATGC | 833 | |
| D11S1029 | cSRL-2a2 | 0.85–0.93 | b | 282 | cSRL-2a2-tA | GACACACCATGAAGCACACC | 250 | 56 |
| | | 11q23.3–q24.1 | | | cSRL-2a2-tZ | AGAGCCAATCTGCAAAGACTG | 250 | |
| D11S1030 | cSRL-2b3 | 0.60–0.85 | b | 177 | cSRL-2b3-tA | CGAGACTCCATCTCAGAAAAA | 833 | 56 |
| | | 11q14.1–q23.3 | | | cSRL-2b3-tZ | TCTATCTGTGGTGCCCCAG | 833 | |
| D11S1031 | cSRL-2c1 | 0.05–0.24 | b | 201 | cSRL-2c1-tA | GCCCTATGTACTTTCTGTTGGC | 500 | 58 |
| | | 11p15.4–p13 | | | cSRL-2c1-tZ | ACAGGAAGCTCAGGGCACTA | 500 | |
| D11S1033 | cSRL-2c2 | 0.33–0.50 | b | 211 | cSRL-2c2-tA | AAGCAACTTCCACATTCAAGTG | 250 | 56 |
| | | 11p11.2–q13.1 | | | cSRL-2c2-tZ | GTGCAATGTCCCCTCATTTT | 250 | |
| D11S1034 | cSRL-2c3 | 0.05–0.24 | b | 261 | cSRL-2c3-tB | AGGCTTTTCTAAACCTTCTCCC | 500 | 56 |
| | | 11p15.4–p13 | | | cSRL-2c3-tY | ACGGAGGCAGATTCCTTTG | 500 | |
| D11S1035 | cSRL-2c4 | 0.93–1.00 | b | 151 | cSRL-2c4-tB | CAGTAACTCCCAGGGCTCC | 250 | 56 |
| | | 11q24.1–q25 | | | cSRL-2c4-tY | CACTCACTGTAAATGCAGCCA | 250 | |
| D11S1036 | cSRL-2c5 | 0.60–0.85 | b | 292 | cSRL-2c5-tB | CCCACAAATACCAAGATGACTG | 250 | 56 |
| | | 11q14.1–q23.3 | | | cSRL-2c5-tY | ACATCAATTTTGGCTGAGCC | 250 | |
| D11S1037 | cSRL-2c7 | 0.93–1.00 | b | 251 | cSRL-2c7-tA | TCTTGGAGTCAGCAATTATCAA | 250 | 56 |
| | | 11q24.1–q25 | | | cSRL-2c7-tZ | TACCTGCTTTTGTGCTACAAAG | 250 | |
| D11S1038 | cSRL-2c8 | 0.50–0.85 | b | 285 | cSRL-2c8-tA | ACAGAGGAGAGTGGCTGGAA | 250 | 58 |
| | | 11q13.1–q23.3 | | | cSRL-2c8-tZ | GGCACTGGGGAAATACTGAA | 250 | |
| D11S1039 | cSRL-2c9 | 0.50–0.60 | b | 218 | cSRL-2c9-tA | TTGTCAGGTTCAGCAAGCAG | 250 | 56 |
| | | 11q13.1–q14.1 | | | cSRL-2c9-tZ | CTAAAATAACAAAAGCCGCCC | 250 | |
| D11S1032 | cSRL-2c10 | 0.05–0.24 | b | 172 | cSRL-2c10-tA | CTCCAGGGAAGCTGACTGAC | 250 | 55 |
| | | 11p15.4–p13 | | | cSRL-2c10-tZ | TCTAGGGTAGGGGAGTTTCTCC | 250 | |
| D11S1040 | cSRL-2d1 | 0.60–0.85 | b | 252 | cSRL-2d1-tA | AAGAATCAGGATATTGTGGCG | 250 | 56 |
| | | 11q14.1–q23.3 | | | cSRL-2d1-tZ | TAGTTGACCTGAATCTTTGGGA | 250 | |
| D11S1041 | cSRL-2d3 | 0.85–0.93 | b | 291 | cSRL-2d3-tA | TCTGTCACGGACAGCAATTC | 250 | 56 |
| | | 11q23.3–q24.1 | | | cSRL-2d3-tZ | AGTTTGAACATGAGATTGCAGC | 250 | |
| D11S1042 | cSRL-2d7 | nd | | 278 | cSRL-2d7-tA | TGGGCTGGACAGGAGAAC | 250 | 58 |
| | | | | | cSRL-2d7-tZ | AAGCATGCCCTCAGAATGAC | 250 | |
| D11S1043 | cSRL-2d8 | 0.05–0.24 | b | 164 | cSRL-2d8-tA | TTGTAGAGCTTTTCTCCTCCCTA | 833 | 49 |
| | | 11p15.4–p13 | | | cSRL-2d8-tZ | CTTAAGTAAAATTTCAGGATACAAATT | 833 | |
| D11S1044 | cSRL-2e1 | 0.00–0.05 | b | 276 | cSRL-2e1-tA | CGGGAGAAACTAGAGGCAGA | 250 | 56 |
| | | 11p15.5–p15.4 | | | cSRL-2e1-tZ | AACTCTGAGGGGAGCAGTCA | 250 | |
| D11S1048 | cSRL-2e2 | 0.93–1.00 | b | 263 | cSRL-2e2-tA | TGTAAGCTGCGTGGCATAAG | 250 | 58 |
| | | 11q24.1–q25 | | | cSRL-2e2-tZ | ATGTGTGTGAGCAGAGCCTG | 250 | |
| D11S1049 | cSRL-2e3 | 0.05–0.24 | b | 253 | cSRL-2e3-tA | TGCTTGGTTTTCAGCATTG | 250 | 56 |
| | | 11p15.4–p13 | | | cSRL-2e3-tZ | ATATTGTCATGCAGCTGGCA | 250 | |
| D11S1050 | cSRL-2e4 | 0.05–0.24 | b | 281 | cSRL-2e4-tA | CGGTTTCTGAGGCATGTGAT | 250 | 56 |
| | | 11p15.4–p13 | | | cSRL-2e4-tZ | AATGAGGGTACAGATCCACACA | 250 | |
| D11S1051 | cSRL-2e6 | 0.24–0.33 | b | 252 | cSRL-2e6-tA | ATACCAAAGCCCCTAAAACATG | 833 | 56 |
| | | 11p13–p11.2 | | | cSRL-2e6-tZ | GTATCATATTTGCTGCTTCCCT | 833 | |
| D11S1052 | cSRL-2e7 | 0.33–0.50 | b | 250 | cSRL-2e7-tA | ACCGGACTCCCTTTCCAC | 250 | 56 |
| | | 11p11.2–q13.1 | | | cSRL-2e7-tZ | TTGTCTACAAATCCCCCTCG | 250 | |
| D11S1053 | cSRL-2e9 | nd | | 171 | cSRL-2e9-tA | TGTCCATGCCTATGTCCTGA | 250 | 56 |
| | | | | | cSRL-2e9-tZ | GGTGTTGGGAAAACTGGCTA | 250 | |
| D11S1045 | cSRL-2e10 | 0.93–1.00 | b | 256 | cSRL-2e10-tA | ACAGTTGATTATCCGATCAGGG | 250 | 56 |
| | | 11q24.1–q25 | | | cSRL-2e10-tZ | AGGATGGAGATGTCTTTGTTGG | 250 | |
| D11S1046 | cSRL-2e11 | 0.60–0.85 | b | 176 | cSRL-2e11-tA | GTCTCTGGGACAGATTCCTCA | 250 | 53 |
| | | 11q14.1–q23.3 | | | cSRL-2e11-tZ | TGCACATCTGTCCTGCTATTT | 250 | |
| D11S1047 | cSRL-2e12 | 0.05–0.24 | b | 254 | cSRL-2e12-tA | GGAAGACAAATCCCAATGGA | 500 | 50 |
| | | 11p15.4–p13 | | | cSRL-2e12-tZ | GAGCCCAAGCGTAGGAAAC | 500 | |
| D11S1056 | cSRL-2f2 | 0.60–0.85 | b | 203 | cSRL-2f2-tA | ATGAGTCCCGTCATACTGTGC | 250 | 56 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | 11q14.1–q23.3 | | | cSRL-2f2-tZ | CCTTGTGGGAAAAAAGGGAG | 250 | |
| D11S1057 | cSRL-2f3 | 0.24–0.33 | b | 172 | cSRL-2f3-tA | CAAGTGTGTTCTGCCTTCACA | 833 | 56 |
| | | 11p13–p11.2 | | | cSRL-2f3-tZ | CACAAGGGCACAGCTAGACA | 833 | |
| D11S1058 | cSRL-2f4 | 0.50–0.60 | b | 260 | cSRL-2f4-tA | TCAGCTGTATAAATGTCTGCCG | 250 | 56 |
| | | 11q13.1–q14.1 | | | cSRL-2f4-tZ | GGTCAGAATGCCTGGACTGT | 250 | |
| D11S1059 | cSRL-2f5 | 0.05–0.24 | b | 256 | cSRL-2f5-tA | TATTTGTCTTTCCATGCCTGG | 250 | 56 |
| | | 11p15.4–p13 | | | cSRL-2f5-tZ | TTTACTAAGCCTGAGAGGCAGC | 250 | |
| D11S1054 | cSRL-2f10 | nd | | 253 | cSRL-2f10-tA | CTAACACAGGAACAGCAAGCC | 250 | 56 |
| | | | | | cSRL-2f10-tZ | ATGTGCAGAGTGTGCAGGTT | 250 | |
| D11S1055 | cSRL-2f11 | nd | | 267 | cSRL-2f11-tA | AGCTTTTTTGATGTTTGCTGG | 250 | 56 |
| | | | | | cSRL-2f11-tZ | GCAACTGCAACAAAAGCAAA | 250 | |
| D11S1061 | cSRL-2g4 | 0.93–1.00 | b | 267 | cSRL-2g4-tA | ACAGTGCCTGCCAAAGATG | 250 | 56 |
| | | 11q24.1–q25 | | | cSRL-2g4-tZ | AATTTGAGGTTTTTGTTAGGGC | 250 | |
| D11S1062 | cSRL-2g6 | 0.05–0.24 | b | 224 | cSRL-2g6-tA | GCGTGAAGGCTGGATTCTAG | 250 | 56 |
| | | 11p15.4–p13 | | | cSRL-2g6-tZ | AACAAGAGTTTCCTCCAAGGC | 250 | |
| D11S1063 | cSRL-2g7 | 0.60–0.85 | b | 151 | cSRL-2g7-tA | ATGAGCATGTTTTTCTGCTACA | 833 | 56 |
| | | 11q14.1–q23.3 | | | cSRL-2g7-tZ | AGCCAACCAACAGTTAAATTGA | 833 | |
| D11S1064 | cSRL-2g9 | 0.05–0.24 | b | 154 | cSRL-2g9-tA | TGCACGTGAGATGAGTCTCC | 250 | 56 |
| | | 11p15.4–p13 | | | cSRL-2g9-tZ | CCACTGCAAAAACACGCTAA | 250 | |
| D11S1060 | cSRL-2g11 | 0.05–0.24 | b | 198 | cSRL-2g11-tA | TTTGTTGTTTAAGTCACCCCG | 250 | 56 |
| | | 11p15.4–p13 | | | cSRL-2g11-tZ | CCCCTGATCTCAGACTTCCA | 250 | |
| D11S1067 | cSRL-2h2 | 0.50–0.85 | b | 264 | cSRL-2h2-tA | GAGAACCCCTGTGTTACCTCC | 250 | 56 |
| | | 11q13.1–q23.3 | | | cSRL-2h2-tZ | AAAACCACAATGCCATGACA | 250 | |
| D11S1068 | cSRL-2h9 | 0.05–0.24 | b | 204 | cSRL-2h9-tA | AGCCTCCCTCATCATTTGG | 250 | 56 |
| | | 11p15.4–p13 | | | cSRL-2h9-tZ | ACTGGTTTTGCACATGTAGCC | 250 | |
| D11S1065 | cSRL-2h10 | 0.60–0.85 | b | 302 | cSRL-2h10-tA | AGAGGTACCCTGCTTAGGATTC | 500 | 56 |
| | | 11q14.1–q23.3 | | | cSRL-2h10-tZ | TCATTCCTCACTCTCAATGCA | 500 | |
| D11S1066 | cSRL-2h11 | 0.33–0.50 | b | 260 | cSRL-2h11-tA | TGTCGGCTCCAGGTTTTC | 250 | 56 |
| | | 11p11.2–q13.1 | | | cSRL-2h11-tZ | CCCTAGCAAGCAGACACACA | 250 | |
| D11S1069 | cSRL-3a1 | 0.33–0.50 | b | 171 | cSRL-3a1-tA | CTTTTTATTTCCCCAAATGGC | 500 | 56 |
| | | 11p11.2–q13.1 | | | cSRL-3a1-tZ | CTGAGGCCTCCTTGTACTGC | 500 | |
| D11S1070 | cSRL-3a3 | 024–0.33 | b | 297 | cSRL-3a3-tA | GCTAATATTTTGAGTCAATTTTCCTC | 833 | 56 |
| | | 11p13–p11.2 | | | cSRL-3a4-tZ | CAAAAACTATGCTAAAGCCTGTATATG | 833 | |
| D11S1071 | cSRL-3a4 | 0.93–1.00 | b | 275 | cSRL-3a4-tZ | GGTGGCTCTGACCTCACATT | 250 | 56 |
| | | 11q24.1–q25 | | | cSRL-3a4-tZ | ATCCTAGCCACCCTAGCCAT | 250 | |
| D11S1072 | cSRL-3a6 | nd | | 172 | cSRL-3a6-tA | GGCATCTTGGCCTGTTTG | 250 | 56 |
| | | | | | cSRL-3a6-tZ | GCCTGGGAACAAAAACAAAA | 250 | |
| D11S1073 | cSRL-3a7 | 0.60–0.85 | b | 158 | cSRL-3a7-tA | GAGGAGCCAGAATGGAACAC | 250 | 56 |
| | | 11q14.1–q23.3 | | | cSRL-3a7-tZ | ATTGCTAGTGTCGGGGCC | 250 | |
| D11S1074 | cSRL-3a8 | 0.50–0.85 | b | 169 | cSRL-3a8-tA | GAGATGAAAAAGATCTGGACCA | 250 | 56 |
| | | 11q13.1–q23.3 | | | cSRL-3a8-tZ | CATCCCTCCTGACCACACTT | 250 | |
| D11S1075 | cSRL-3a9 | 0.05–0.24 | b | 227 | cSRL-3a9-tA | AGCACCCTGAACCCTTCC | 250 | 56 |
| | | 11p15.4–p13 | | | cSRL-3a9-tZ | GAATAGCACTGTTTTGAAGGGG | 250 | |
| D11S1076 | cSRL-3b1 | 0.33–0.50 | b | 155 | cSRL-3b1-tA | AGAGTGGTTGGGGAAGGC | 250 | 57 |
| | | 11p11.2–q13.1 | | | cSRL-3b1-tZ | GAGTCCTGTCCTCCTTGCTG | 250 | |
| D11S1080 | cSRL-3b2 | 0.33–0.50 | b | 317 | cSRL-3b2-tA | CACCATGGGTATCCAGTGC | 500 | 56 |
| | | 11p11.2–q13.1 | | | cSRL-3b2-tZ | ACCAGGCCCTAGAATTCCAG | 500 | |
| D11S1081 | cSRL-3b3 | 0.24–0.60 | c | 173 | cSRL-3b3-tA | GCAGTATTTGGCTTTCTGTTCC | 250 | 57 |
| | | 11p13–p13.5 | | | cSRL-3b3-tZ | AACCTAGGTGCCCATCAGTG | 250 | |
| D11S1082 | cSRL-3b8 | 0.85–0.93 | b | 193 | cSRL-3b8-tA | ACGCATTGTACCCATGTCAA | 250 | 56 |
| | | 11q23.3–q24.1 | | | cSRL-3b8-tZ | CTCAAAAGAGCAGCCAAGGT | 250 | |
| D11S1077 | cSRL-3b10 | 0.60–0.85 | b | 307 | cSRL-3b1-tA | GATATGGACGTCTGCAAAACA | 500 | 57 |
| | | 11q14.1–q23.3 | | | cSRL-3b1-tZ | TAAGGAAGGAAAGGGAGGGA | 500 | |
| D11S1078 | cSRL-3b11 | 0.60–0.85 | b | 285 | cSRL-3b11-tA | TTTGGAGCTGGACAGTGTTG | 833 | 56 |
| | | 11q14.1–q23.3 | | | cSRL-3b11-tZ | TTCTCTATTGTGTCCCCTCCC | 833 | |
| D11S1079 | cSRL-3b12 | 0.33–0.50 | b | 161 | cSRL-3b12-tA | TGCAATGACGAAGCCTACTG | 250 | 56 |
| | | 11p11.2–q13.1 | | | cSRL-3b12-tZ | AAGGCACTTCCCTGCTCC | 250 | |
| D11S1083 | cSRL-3c4 | 0.93–1.00 | b | 151 | cSRL-3c4-tA | GGGAAAGAAGGCGCATAAG | 833 | 56 |
| | | 11q24.1–q25 | | | cSRL-3c4-tZ | AAATTCTCCTGATCGACCTCA | 833 | |
| D11S1084 | cSRl-3d1 | 0.33–0.50 | b | 152 | cSRL-3d1-tA | TCAGTTCCTTCTTGGCACG | 250 | 56 |
| | | 11p11.2–q13.1 | | | cSRL-3d1-tZ | CATGCCACATTTGCCATTTA | 250 | |
| D11S1087 | cSRL-3d3 | 0.50–0.60 | b | 146 | cSRL-3d3-tA | GAACAATATAACCATGCAACCC | 833 | 48 |
| | | 11q13.1–14.1 | | | cSRL-3d3-tZ | TCTACACTACTCCTTTCCCG | 833 | |
| D11S1088 | cSRL-3d5 | 0.00–0.05 | b | 151 | cSRL-3d5-tA | TGAAAGACAATTAGGTGAACCC | 833 | 56 |
| | | 11p15.5–p15.4 | | | cSRL-3d5-tZ | TTCCTGGGCCATCTCATC | 833 | |
| D11S1089 | cSRL-3d6 | 0.00–0.05 | b | 267 | cSRL-3d6-tA | CCCCCATGATGAGGTTAGTG | 250 | 56 |
| | | 11p15.5–p15.4 | | | cSRL-3d6-tZ | GTGCGTTTTGGCAGGATAT | 250 | |
| D11S1085 | cSRL-3d11 | 0.33–0.50 | b | 255 | cSRL-3d11-tA | AAGGATGGTTCAAGATCCCC | 250 | 56 |
| | | 11p11.2–q13.1 | | | cSRL-3d11-tZ | CTGCCCCCAAGTTACTGTA | 250 | |
| D11S1086 | cSRL-3d12 | 0.24–0.33 | b | 276 | cSRL-3d12-tA | GGGAAGGACACCAAGATAAGC | 250 | 56 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | 11p1–p11.2 | | | cSRL-3d12-tZ | AATTTGGCTCTGGGATTCCT | 250 | |
| D11S1090 | cSRL-3e1 | nd | | 264 | cSRL-3e1-tA | AGGTGAACTACCATGGCCAG | 250 | 56 |
| | | | | | cSRL-3e1-tZ | GGGGAGGATGTACTTGGAGA | 250 | |
| D11S1093 | cSRL-3e2 | 0.33–0.50 | b | 147 | cSRL-3e2-tA | TTTACTTTGTTGTGATAAGACAACCC | 833 | 56 |
| | | 11p11.2–q13.1 | | | cSRL-3e2-tZ | TGAATAATGTGGACACCAGAGC | 833 | |
| D11S1094 | cSRL-3e4 | nd | | 286 | cSRL-3e4-tA | ACCATCACCACCATCCATCT | 833 | 56 |
| | | | | | cSRL-3e4-tZ | CAATGGAATATTGCTTAGCCTT | 833 | |
| D11S1095 | cSRL-3e5 | 0.00–0.05 | b | 179 | cSRL-3e5-tA | CCTTAGAAGCCAAAGCTCCC | 833 | 56 |
| | | 11p15.5–p15.4 | | | cSRL-3e5-tZ | CATTATCGTGAGGCTGAAAGC | 833 | |
| D11S1096 | cSRL-3e8 | 0.85–0.93 | b | 253 | cSRL-3e8-tA | TGCCCCAAGCTCTACACTG | 250 | 56 |
| | | 11q23.3–q24.1 | | | cSRL-3e8-tZ | GGTGTCGAGATGCAGCTGTA | 250 | |
| D11S1091 | cSRL-3e10 | 0.85–0.93 | b | 250 | cSRL-3e10-tA | CCACAGAGTGCATCATCCAT | 500 | 56 |
| | | 11q23.3–q24.1 | | | cSRL-3e10-tZ | TCAGTGTTGTAAGTGGTGGCG | 500 | |
| D11S1092 | cSRL-3e12 | 0.33–0.50 | b | 245 | cSRL-3e12-tA | AGGCAAGTCTCCCATTTTTG | 250 | 56 |
| | | 11p11.2–q13.1 | | | cSRL-3e12-tZ | TGCGCTAAATGGAAACACTG | 250 | |
| D11S1099 | cSRL-3h2 | 0.05–0.24 | b | 257 | cSRL-3h2-tA | TCTTCATGCAAGCCAAACAG | 833 | 56 |
| | | 11p15.4–p13 | | | cSRL-3h2-tZ | CAGCCAGCAATTGTGTGG | 833 | |
| D11S1100 | cSRL-3h3 | 0.24–0.33 | b | 250 | cSRL-3h3-tA | TTGGTGCAAAAGTAATTGCG | 833 | 56 |
| | | 11p1–p11.2 | | | cSRL-3h3-tZ | GAAGAAATGCACACAAATCCC | 833 | |
| D11S1101 | cSRL-3h4 | 0.50–0.85 | b | 250 | cSRL-3h4-tA | AAACAGAAAACCAAACACTGCA | 833 | 56 |
| | | 11q13.1–q23.3 | | | cSRL-3h4-tZ | TGAGATTAATGTGCAGCATGTG | 833 | |
| D11S1102 | cSRL-3h6 | 0.24–0.33 | b | 159 | cSRL-3h6-tA | GAGCATGCTTGGAGTCAACA | 833 | 56 |
| | | 11p1–p11.2 | | | cSRL-3h6-tZ | TAAGGGCCTGATCATCTTGG | 833 | |
| D11S1103 | cSRL-3h7 | 0.24–0.33 | b | 252 | cSRL-3h7-tA | CCTGCATCCATCCTTCAAGT | 250 | 56 |
| | | 11p1–p11.2 | | | cSRL-3h7-tZ | AGGTGCAGAAGCTGGTGAGT | 250 | |
| D11S1104 | cSRL-3h8 | 0.60–0.85 | b | 255 | cSRL-3h8-tA | AATTCACACATTCGAATTGAAA | 833 | 56 |
| | | 11q14.1–q23.3 | | | cSRL-3h8-tZ | AGGAGATCGACAATGCAGGT | 833 | |
| D11S1097 | cSRL-3h10 | nd | | 188 | cSRL-3h10-tA | CCTCTGCCTTTCCCATGTTA | 833 | 56 |
| | | | | | cSRL-3h10-tZ | CCTATGTTAAACCCCTGGCA | 833 | |
| D11S1098 | cSRL-3h11 | 0.05–0.24 | b | 245 | cSRL-3h11-tA | AACAGCAAAAAACTAAAGCAATCC | 833 | 56 |
| | | 11p15.4–p13 | | | cSRL-3h11-tZ | GCGCTTTTAACTACAGGTACATTT | 833 | |
| D11S1105 | cSRL-4a4 | 0.50–0.60 | b | 157 | cSRL-4a4-tA | TTGGATTGAAAGAAGTTGGTCT | 833 | 56 |
| | | 11q13.1–q14.1 | | | cSRL-4a4-tZ | AAAGTCACAAGGACAATTTTGC | 833 | |
| D11S1106 | cSRL-4a6 | 0.05–0.24 | b | 165 | cSRL-4a6-tA | TTATCAGCAGCATGAAAACAGA | 833 | 56 |
| | | 11p15.4–p13 | | | cSRL-4a6-tZ | CATGGACCTTCAGCATGATG | 833 | |
| D11S1107 | cSRL-4a7 | 0.24–0.33 | b | 190 | cSRL-4a7-tA | GAGATGAGAAAATCAAGGCTGG | 250 | 56 |
| | | 11p1–p11.2 | | | cSRL-4a7-tZ | GCACTCGGGTTGTTTCCATA | 2S0 | |
| D11S1108 | cSRL-4a9 | 0.85–0.93 | b | 150 | cSRL-4a9-tA | CCACCACCACACTCCCAGT | 250 | 56 |
| | | 11q23.3–q24.1 | | | cSRL-4a9-tZ | GTCACTTGCACACACTTAGCC | 250 | |
| D11S1109 | cSRl-4b1 | 0.50–0.60 | b | 255 | cSRL-4b1-tA | TTATGCGCTGTACTAAAGCGTT | 250 | 56 |
| | | 11q13.1–q14.1 | | | cSRL-4b1-tZ | TACACACCATCCTTTATGCTGC | 250 | |
| D11S1112 | cSRL-4b3 | 0.05–0.24 | b | 150 | cSRL-4b3-tA | CCCTATCATTGGCAGCTTGT | 500 | 56 |
| | | 11p15.4–p13 | | | cSRL-4b3-tZ | ATAAAAGCAGCATCTTTTTCGC | 500 | |
| D11S1113 | cSRL-4b4 | nd | | 249 | cSRL-4b4-tA | CCTTTCCAGCTCACCTTCTG | 250 | 56 |
| | | | | | cSRL-4b4-tZ | ACCCTGGCAGTGTCTAGGG | 250 | |
| D11S1114 | cSRL-4b5 | 0.05–0.24 | b | 123 | cSRL-4b5-tA | CCTTTTCACGTCCCTGACTC | 833 | 56 |
| | | 11p15.4–p13 | | | cSRL-4b5-tZ | AAATGAAGAAAATACCCAGACTGG | 833 | |
| D11S1115 | cSRL-4b6 | 0.24–0.33 | b | 260 | cSRL-4b6-tA | AGCAAGACTCTGTCTCGAAAAA | 633 | 56 |
| | | 11p13–p11.2 | | | cSRL-4b6-tZ | AAAGTGCAAATAAGTAAGCCCA | 833 | |
| D11S1116 | cSRL-4b7 | 0.93–1.00 | b | 283 | cSRL-4b7-tA | ATGTAGGAACTGGGGCAGTG | 833 | 56 |
| | | 11q24.1–q25 | | | cSRL-4b7-tZ | TGAAAGCAGTGAGTTTACGGG | 833 | |
| D11S1117 | cSRL-4b8 | 0.60–0.85 | b | 251 | cSRL-4b8-tA | TCTCTCATTTCAGCAGCATCA | 833 | 52 |
| | | 11q14.1–q23.3 | | | cSRL-4b8-tZ | TGGTTCTTCTCCTTTGGCC | 833 | |
| D11S1110 | cSRL-4b10 | 0.50–0.85 | b | 295 | cSRL-4b10-tA | TCCCGCAGACTGTCTCTTG | 250 | 56 |
| | | 11q13.1–q23.3 | | | cSRL-4b10-tZ | AGAGCTAGGCTGGGAGCAG | 250 | |
| D11S1111 | cSRL-4b12 | 0.85–0.93 | b | 317 | cSRL-4b12-tA | TTGAAGACCCCCAGAGAAGA | 833 | 58 |
| | | 11q23.3–q24.1 | | | cSRL-4b12-tZ | CTAGAAGCAAGAGGGAGTCAGC | 833 | |
| D11S1120 | cSRL-4c2 | 0.05–0.24 | b | 251 | cSRL-4c2-tA | GAATGCTCTCTGCTATGGATTG | 833 | 56 |
| | | 11p15.4–p13 | | | cSRL-Ac2-tZ | TAACATGGTGGAAGGCATCA | 833 | |
| D11S1121 | cSRL-4c3 | 0.24–0.33 | b | 213 | cSRL-4c3-tA | TGGTTTTTGTACCAGAACAGAA | 500 | 56 |
| | | 11p13–p11.2 | | | cSRL-4c3-tZ | TGGTGGCAGGCACCTGTA | 500 | |
| D11S1122 | cSRL-4c6 | 0.05–0.24 | b | 193 | cSRL-4c4-tA | ATGAAACTAAAACTTTGTTTGAAAAGA | 500 | 56 |
| | | 11p15.4–p13 | | | cSRL-4c4-tZ | TCCTCTAGATTTTCTCTTCTACTGGC | 500 | |
| D11S1123 | cSRL-4c8 | 0.24–0.33 | b | 211 | cSRL-4c6-tA | GCAAATCCCTGATTTACAGAGG | 500 | 56 |
| | | 11p1–p11.2 | | | cSRL-4c6-tZ | AATTTTTGGGGGAAACTGG | 500 | |
| D11S1124 | cSRL-4c8 | 0.93–1.00 | b | 179 | cSRL-4c8-tA | TCTATAACCCTGCCCACAGG | 250 | 56 |
| | | 11q24.1–q25 | | | cSRL-4c8-tZ | AATGTGCTCCGAAGACAGCT | 250 | |
| D11S1118 | cSRL-4c10 | nd | | 156 | cSRL-4c10-tA | ACATAAATGTGTGCCCATGGA | 250 | |
| | | | | | cSRL-4c10-tZ | ACGTAGTGATGAAGCCTGGG | 250 | |
| D11S1119 | cSRL-4c11 | 0.85–0.93 | | 286 | cSRL-4c11-tA | GGTTCATTTCAGTGCCCTGT | 250 | |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
|  |  | 11q23.3–q24.1 |  |  | cSRL-4c11-tZ | CAGACAAGGACGGCCTCTAC | 250 |  |
| D11S1125 | cSRL-4d1 | 0.24–0.33 | b | 179 | cSRL-4d1-tA | CCTCTTAGGCTTATTGTGGGA | 250 | 56 |
|  |  | 11p13–p11.2 |  |  | cSRL-4d1-tZ | TTCACTCTGTTGTGCTACCAAA | 250 |  |
| D11S1127 | cSRL-4d4 | 0.33–0.50 | b | 201 | cSRL-4d4-tA | ATGAATTAGGCATTGGGCTG | 500 | 58 |
|  |  | 11p11.2–q13.1 |  |  | cSRL-4d4-tZ | CCAGTGGAGGGCAGAGTAAA | 500 |  |
| D11S1128 | cSRL-4d6 | 0.05–0.24 | b | 139 | cSRL-4d6-tA | TGGAAAATTTACTTGATTCCCAA | 500 | 56 |
|  |  | 11p15.4–p13 |  |  | cSRL-4d6-tZ | TAACACATTATTTCTCTTTCACGATATG | 500 |  |
| D11S1129 | cSRL-4d7 | nd |  | 171 | cSRL-4d7-tA | CAAGACCCTGTCTCAAAAAAGC | 250 | 56 |
|  |  |  |  |  | cSRL-4d7-tZ | AAAAAAAAAAATGTTGGTGGGG | 250 |  |
| D11S1126 | cSRL-4d10 | 0.50–0.85 | b | 257 | cSRL-4d10-tA | TCGCCTTCAGCTATGCTAAA | 250 | 56 |
|  |  | 11q13.1–q23.3 |  |  | cSRL-4d10-tZ | AGCTGCTGGCAAAAACAAAT | 250 |  |
| D11S1130 | cSRL-4e1 | 0.05–0.24 | b | 173 | cSRL-4e1-tA | TCCTTTGGAAATTTTTTGCG | 500 | 56 |
|  |  | 11.15.4–p13 |  |  | cSRL-4e1-tZ | AGTAGAGATGGGATTGGGCC | 500 |  |
| D11S1131 | cSRL-4e3 | nd |  | 210 | cSRL-4e3-tA | AGCAAAAGCAGTTTTGAGAAGG | 833 | 56 |
|  |  |  |  |  | cSRL-4e3-tZ | TTTCAAAAAACCAGCTTTTCA | 833 |  |
| D11S1132 | cSRL-4e4 | nd |  | 169 | cSRL-4e4-tA | CTGTGCTTTCATGTTCATTGC | 500 | 56 |
|  |  |  |  |  | cSRL-4e4-tZ | ATTCACGTTGTTGTAGGTGACA | 500 |  |
| D11S1133 | cSRL-4e5 | 0.60–0.85 | b | 110 | cSRL-4e5-tA | TCCTCCCCAAAACCCTTAAC | 833 | 56 |
|  |  | 11q14.1–q23.3 |  |  | cSRL-4e5-tZ | ATTATGTCTCTGTCAGCTCCCC | 833 |  |
| D11S1134 | cSRL-4e6 | nd |  | 163 | cSRL-4e6-tA | CTGCCAAGATTTCAGAGGATG | 250 | 56 |
|  |  |  |  |  | cSRL-4e6-tZ | GCTCCACTAGGCAGTGCC | 250 |  |
| D11S1135 | cSRL-4e8 | 0.60–0.85 | b | 341 | cSRL-4e8-tA | TGAGACTTGCCCTCTACATCA | 250 | 54 |
|  |  | 11q14.1–q23.3 |  |  | cSRL-4e8-tZ | TTCAGGCATTCACATTCTGC | 250 |  |
| D11S1136 | cSRL-4e9 | 0.60–0.85 | b | 259 | cSRL-4e9-tA | GGATTGCCAGGTGAATGC | 500 | 56 |
|  |  | 11q14.1–q23.3 |  |  | cSRL-4e9-tZ | ATAATTTCCATGGCCCCTTC | 500 |  |
| D11S1138 | cSRL-4f2 | 0.33–0.50 | b | 161 | cSRL-4f2-tA | CACGCCATTGTCAAAAACC | 250 | 54 |
|  |  | 11p11.2–q13.1 |  |  | cSRL-4f2-tZ | ACAGCTAAAGCAACGTTTTGC | 250 |  |
| D11S1139 | cSRL-4f3 | 0.33–0.50 | b | 161 | cSRL-4f3-tA | ACTAGTATCGGGCAGCCAGA | 833 | 54 |
|  |  | 11p11.2–q13.1 |  |  | cSRL-4f3-tZ | TCGCACCTACAAAGAGCCTT | 833 |  |
| D11S1140 | cSRL-4f6 | 0.33–0.50 | b | 260 | cSRL-4f6-tA | GAGTCCAGATTTGAAGAGCAGG | 833 | 54 |
|  |  | 11p11.2–q13.1 |  |  | cSRL-4f6-tZ | TGATTTGAGGAATAGAATGGCA | 833 |  |
| D11S1141 | cSRL-4f8 | 0.05–0.24 | b | 195 | cSRL-4f8-tA | GCACTTGGGAGCCATCAG | 500 | 54 |
|  |  | 11q15.4–p13 |  |  | cSRL-4f8-tZ | GGAGGGAAATAGTGGGGGTA | 500 |  |
| D11S1142 | cSRl-4f9 | 0.50–0.60 | b | 196 | cSRL-4f9-tA | GAGGTGGTGGGCACCTGTA | 250 | 54 |
|  |  | 11q13.1–q14.1 |  |  | cSRL-4f9-tZ | AGAGGGGAGGAACACACCTT | 250 |  |
| D11S1137 | cSRL-4f12 | 0.60–0.85 | b | 323 | cSRL-4f12-tA | AAATCTAGGCATCATGGCTCA | 250 | 54 |
|  |  | 11q14.1–q23.3 |  |  | cSRL-4f12-tZ | GCTTCCATGGCAGGAAGAT | 250 |  |
| D11S1143 | cSRL-4f1 | 0.24–0.33 | b | 255 | cSRL-4g1-tA | TGGTAGGTACTGCTCCTGGG | 500 | 54 |
|  |  | 11p13–p11.2 |  |  | cSRL-4g1-tZ | GAGAATTGCGCAGCCTAATC | 500 |  |
| D11S1146 | cSRL-4g3 | nd |  | 286 | cSRL-4g3-tA | TGGGCTCTTTATTCTGTTCCA | 500 | 56 |
|  |  |  |  |  | cSRL-4g3-tZ | ATACTGCCCAAAGCAGTGTACA | 500 |  |
| D11S1147 | cSRL-4g4 | 0.85–0.93 | b | 263 | cSRL-4g4-tA | GGAATCACTGAGTTAGAAGGAATAGG | 500 | 56 |
|  |  | 11q23.3–q24.1 |  |  | cSRL-4g4-tZ | TTTGTAGCACTCTATCCTCAAAACC | 500 |  |
| D11S1148 | cSRL-498 | 0.24–0.33 | b | 219 | cSRL-4g8-tA | CCAAACGCAATTAGAAATCAG | 500 | 56 |
|  |  | 11p13–p11.2 |  |  | cSRL-4g8-tZ | CACTGTTCCCAGCCTGTTC | 500 |  |
| D11S1149 | cSRL-4g9 | 0.05–0.24 | b | 273 | cSRL-4g9-tA | ACTAAATGAGCAAAGCCCCA | 500 | 56 |
|  |  | 11p15.4–p13 |  |  | cSRL-4g9-tZ | AGAATCAAAGCTITTCCCTCTG | 500 |  |
| D11S1144 | cSRL-4g10 | nd |  | 154 | cSRL-4g10-tA | AACTTGTGTCACAGGGGTTTG | 500 | 56 |
|  |  |  |  |  | cSRL-4g10-tZ | AATGCATGGACACAGAGGG | 500 |  |
| D11S1145 | cSRL-4g11 | 0.05–0.24 | b | 251 | cSRL-4g11-tA | ACAAAGCTTCACATAGAAGCCC | 250 | 54 |
|  |  | 11p15.4–p13 |  |  | cSRL-tg11-tZ | TTTCTGAAAACAGTTGCCACC | 250 |  |
| D11S1152 | cSRL-4h5 | 0.05–0.24 | b | 154 | cSRL-4h5-tA | ATGAAGGGCGTAGTCCCC | 833 | 56 |
|  |  | 11p15.4–p13 |  |  | cSRL-4h5-tZ | TGGCCTGGTCCCTTTAGAG | 833 |  |
| D11S1153 | cSRL-4h8 | 0.93–1.00 | b | 262 | cSRL-4h8-tA | AAGAGGACGACCATGTGAGG | 250 | 56 |
|  |  | 11q24.1–q25 |  |  | cSRL-4h8-tZ | TTTTTGTGACTGGCCCTTTC | 250 |  |
| D11S1150 | cSRL-4h11 | 0.24–0.33 | b | 254 | cSRL-4h11-tA | CCTTGTATTCAGTGCCTGAGG | 250 | 56 |
|  |  | 11p13–p11.2 |  |  | cSRL-4h11-tZ | AGTGGACACTTCCCAGGATG | 250 |  |
| D11S1151 | cSRL-4h12 | 0.85–0.93 | b | 154 | cSRL-4h12-tA | ACTCATTCATGGAACCCCAA | 250 | 56 |
|  |  | 11q23.3–q24.1 |  |  | cSRL-4h12-tZ | CATCATGCTAGGCACTGACTG | 250 |  |
| D11S1154 | cSRL-5a1 | 0.05–0.24 | b | 151 | cSRL-5a1-tA | GTTTCCTGCAACTTCATTTTCC | 833 | 58 |
|  |  | 11p15.4–p13 |  |  | cSRL-5a1-tZ | CTGGGCAACCTGATAAATCTG | 833 |  |
| D11S1157 | cSRL-5a2 | 0.50–0.85 | b | 305 | cSRL-5a2-tA | TAAAACAAGAGCAAACCAAACG | 250 | 56 |
|  |  | 11q13.1–q23.3 |  |  | cSRL-5a2-tZ | GTTCAATCTTGGGAGGCTGT | 250 |  |
| D11S1158 | cSRL-5a3 | 0.50–0.85 | b | 277 | cSRL-5a3-tA | ATTTTAACCTCACTGTGCCTCA | 250 | 58 |
|  |  | 11q13.1–q23.3 |  |  | cSRL-5a3-tZ | TTCAGAGAGTGCTGGCCAC | 250 |  |
| D11S1159 | cSRL-5a4 | 0.60–0.85 | b | 250 | cSRL-5a4-tA | ACAGTGTTGAATCGGGATTTG | 250 | 56 |
|  |  | 11q14.1–q23.3 |  |  | cSRL-5a4-tZ | CTGTGGCTATGTTCTAAGGAGC | 250 |  |
| D11S1160 | cSRL-5a5 | 0.60–0.85 | b | 164 | cSRL-5a5-tA | TCATTAGCATTTTATGTGCGG | 500 | 56 |
|  |  | 11q14.1–q23.3 |  |  | cSRL-5a5-tZ | TGGATAAAATGGAAAATGCTCA | 500 |  |
| D11S1161 | cSRL-5a6 | 0.93–1.00 | b | 155 | cSRL-5a6-tA | GACAGTGGAGGCAATGTATTTT | 833 | 52 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | 11q24.1–q25 | | | cSRL-5a6-tZ | GAAAGAGACTTTATCTTGGGCC | 833 | |
| D11S1162 | cSRL-5a7 | 0.24–0.50 | b | 204 | cSRL-5a7-tA | AAGTCAGGGAGCTTTTTGAGC | 250 | 56 |
| | | 11p13–q13.1 | | | cSRL-5a7-tZ | ATAAATGCCCTTGATTAGGTGC | 250 | |
| D11S1163 | cSRL-5a9 | 0.85–0.93 | b | 258 | cSRL-5a9-tA | CCTGAGGCTGAGTTAGGCTG | 250 | 56 |
| | | 11q23.3–q24.1 | | | cSRL-5a9-tZ | TCCAGATGGGAAAACTGAGC | 250 | |
| D11S1155 | cSRL-5a10 | 0.24–0.33 | b | 285 | cSRL-5a10-tA | GAAAAAGATAAACCCAACGTGA | 833 | 56 |
| | | 11p13–p11.2 | | | cSRL-5a10-tZ | ACGGCACACATTTTTTAGCC | 833 | |
| D11S1156 | cSRL-5a11 | 0.50–0.60 | b | 290 | cSRL-5a11-tA | GTGACTCAGTGATTTGAGGTGC | 250 | 56 |
| | | 11q13.1–q14.1 | | | cSRL-5a11-tZ | TGGAGTGGAGTGAAGTGAAGG | 250 | |
| D11S1164 | cSRL-5b1 | 0.93–1.00 | b | 198 | cSRL-5b1-tA | CCATGATTCCAAAACAACCC | 500 | 56 |
| | | 11q24.1–q25 | | | cSRL-5b1-tZ | CCCTCTCTCCTTACCTGCAA | 500 | |
| D11S1165 | cSRL-5b7 | 0.05–0.24 | b | 151 | cSRL-5b7-tA | AAATATCACTGCCAGGCCAA | 500 | 56 |
| | | 11p15.4–p13 | | | cSRL-5b7-tZ | AAACTGCAATTACTTTGCACC | 500 | |
| D11S1166 | cSRL-5b8 | 0.05–0.24 | b | 150 | cSRL-5b8-tA | TGCTTGGCAAAATGTATATGG | 250 | 56 |
| | | 11p15.4–p13 | | | cSRL-5b8-tZ | AAATATGCCCAGGATTTTCTTTT | 250 | |
| D11S1169 | cSRl-5c2 | 0.50–0.85 | b | 258 | cSRL-5c2-tA | AAGGAGCAGAGTTGTGGGCT | 833 | 56 |
| | | 11q13.1–q23.3 | | | cSRL-5c2-tZ | AGTCAGATGAAGAGCAACCCA | 833 | |
| D11S1170 | cSRL-5c3 | 0.05–0.24 | b | 278 | cSRL-5c3-tA | CTACATGACCTGGCTGCCTT | 500 | 58 |
| | | 11p15.4–p13 | | | cSRL-5c3-tZ | TGATTGGCAATGGCAGAATA | 500 | |
| D11S1171 | cSRL-5c5 | 0.24–0.33 | b | 307 | cSRL-5c5-tA | CAGAGGCACTACACTCTCATTG | 500 | 58 |
| | | 11p13–p11.2 | | | cSRL-5c5-tZ | CAAGTGCAACAGTTTGAGAACC | 500 | |
| D11S1172 | cSRL-5c8 | 0.00–0.05 | b | 155 | cSRL-5c8-tA | CCGCTGACTTAAATAAATCCTG | 500 | 56 |
| | | 11p15.5–p15.4 | | | cSRL-5c8-tZ | AGTTTTGGTAACATGCTGTGG | 500 | |
| D11S1173 | cSRL-5c9 | 0.60–0.85 | b | 242 | cSRL-5c9-tA | TTGTTCAACTATTACTGACACTACTGC | 500 | 56 |
| | | 11q14.1–q23.3 | | | cSRL-5c9-tZ | CAGGCTGATGCATACTTACTTGT | 500 | |
| D11S1167 | cSRl-5c10 | 0.60–0.85 | b | 261 | cSRL-5c10-tA | ACATGAGCCACCATGCCT | 250 | 56 |
| | | 11q14.1–q23.3 | | | cSRL-5c10-tZ | CCTTGCCAAATCTGCTCAAC | 250 | |
| D11S1168 | cSRL-5c11 | 0.05–0.24 | b | 269 | cSRL-5c11-tA | GGGGGATGCATTCTGACTAA | 833 | 56 |
| | | 11p15.4–p13 | | | cSRL-5c11-tZ | CAAGAGAACGGCTTTTGGAG | 833 | |
| D11S1176 | cSRL-5d2 | 0.33–0.50 | b | 252 | cSRL-5d2-tA | GTCCTGCCCTTCATTACTGC | 500 | 58 |
| | | 11p11.2–q13.1 | | | cSRL-5d2-tZ | CATGCTGGACACTACTCTGACC | 500 | |
| D11S1177 | cSRL-5d3 | nd | | 160 | cSRL-5d3-tA | AGAAACTCACGTATGCCAAGG | 250 | 56 |
| | | | | | cSRL-5d3-tZ | TTTAGTGCTTTGACACATTTGC | 250 | |
| D11S1178 | cSRL-5d5 | 0.60–0.85 | b | 312 | cSRL-5d5-tA | GTGTTCTTAAAGGGGTCTGGC | 500 | 56 |
| | | 11q14.1–q23.3 | | | cSRL-5d5-tZ | CATGCATTCTTCCTGTCGG | 500 | |
| D11S1179 | cSRL-5d6 | 0.33–0.50 | b | 287 | cSRL-5d6-tA | ATACGCCATGGTTGCCTAAG | 500 | 56 |
| | | 11p11.2–q13.1 | | | cSRL-5d6-tZ | TGACAATATCAAGTGTGGCCA | 500 | |
| D11S1180 | cSRL-5d7 | 0.60–0.85 | b | 200 | cSRL-5d7-tA | GGAAGGAGTATTACACTGAGAACT | 500 | 56 |
| | | 11q14.1–q23.3 | | | cSRL-5d7-tZ | TAATGTGTTTTAGCTGCAAGGGA | 500 | |
| D11S1181 | cSRL-5d8 | 0.05–0.24 | b | 211 | cSRL-5d8-tA | CAGCAGAAATCTCTGTGACACC | 250 | 56 |
| | | 11p15.4–p13 | | | cSRL-5d8-tZ | TATTGTGAGACAGGTCTGGGG | 250 | |
| D11S1182 | cSRL-5d9 | 0.50–0.60 | b | 297 | cSRL-5d9-tA | TTTAGGAATCAAATCTGATGGC | 500 | 58 |
| | | 11q13.1–q14.1 | | | cSRL-5d9-tZ | AGGGTGGATTGCTGAACTTG | 500 | |
| D11S1174 | cSRL-5d10 | 0.50–0.85 | b | 251 | cSRL-5d10-tA | TCCTTCTCAAGTCTCTGCTTCC | 250 | 56 |
| | | 11q13.1–q23.3 | | | cSRL-5d10-tZ | GCAAGCCATATCTAGCATTTTT | 250 | |
| D11S1175 | cSRL-5d11 | 0.93–1.00 | b | 186 | cSRL-5d11-tA | AGCAGTGGCCTAAACCATTG | 500 | 58 |
| | | 11q24.1–q25 | | | cSRL-5d11-tZ | CACACTGTGGACTGGATTGG | 500 | |
| D11S1183 | cSRL-5e1 | 0.33–0.50 | b | 287 | cSRL-5e1-tA | AGACTGCCTTTCCCTGGC | 250 | 56 |
| | | 11p11.2–q13.1 | | | cSRL-5e1-tZ | AGGAAATTGGAGGCTGGTTT | 250 | |
| D11S1185 | cSRL-5e2 | 0.93–1.00 | b | 334 | cSRL-5e2-tA | AAAAGGTCCTGGCATACAGC | 833 | 58 |
| | | 11q24.1–q25 | | | cSRL-5e2-tZ | AACTAATTGGTCAGGCCACG | 833 | |
| D11S1186 | cSRL-5e3 | 0.05–0.24 | b | 287 | cSRL-5e3-tA | CCCAATTGTCTCCCTAAATCC | 833 | 58 |
| | | 11p15.4–p13 | | | cSRL-5e3-tZ | AATCTGCATGGTCAAAGATGG | 833 | |
| D11S1187 | cSRL-5e4 | 0.05–0.24 | b | 256 | cSRL-5e4-tA | CATTGTTGGCACAGAGATGG | 833 | 58 |
| | | 11p15.4–p13 | | | cSRL-5e4-tZ | CACTTCCACATTTGCAAATCA | 833 | |
| D11S1188 | cSRL-5e5 | 0.33–0.50 | b | 269 | cSRL-5e5-tA | GACAGAGCAGCAAACTCAAGG | 833 | 58 |
| | | 11p11.2–q13.1 | | | cSRL-5e5-tZ | TCTGACTCCTTCCTGTCTAGGG | 833 | |
| D11S1189 | cSRL-5e6 | 0.50–1.00 | b | 263 | cSRL-5e6-tA | CTTCCCATTGAAACCCTTAGG | 833 | 52 |
| | | 11q13.1–q25 | | | cSRL-5e6-tZ | GCTCTATTCCTATCCGTTTCCC | 833 | |
| D11S1184 | cSRL-5e10 | 0.05–0.24 | b | 211 | cSRL-5e10-tA | TCAGGTCTCATGATATTGGGC | 500 | 56 |
| | | 11p15.4–p13 | | | cSRL-5e10-tZ | TTAGCTGGCTGTCTGTCTTACC | 500 | |
| D11S1190 | cSRL-5f1 | nd | | 254 | cSRL-5f1-tA | GTGAGGGCATTTCCCTCTAA | 250 | 56 |
| | | | | | cSRL-5f1-tZ | CCAGGCCCTTCATCCATC | 250 | |
| D11S1193 | cSRL-5f2 | 0.00–0.05 | b | 289 | cSRL-5f2-tA | CCTGGGTTAAAACACTCAATTG | 833 | 56 |
| | | 11p15.5–p15.4 | | | cSRL-5f2-tZ | AGGAAGCTGATTTTCCTGC | 833 | |
| D11S1194 | cSRL-5f3 | 0.33–0.50 | b | 215 | cSRL-5f3-tA | CTCACAACCCTCCATGGC | 250 | 56 |
| | | 11p11.2–q13.1 | | | cSRL-5f3-tZ | ACTAAACCACCAGGGCAGG | 250 | |
| D11S1195 | cSRL-5f4 | 0.05–0.24 | b | 230 | cSRL-5f4-tA | AAGTAAAGCCGCAAAAGCAA | 250 | 56 |
| | | 11p15.4–p13 | | | cSRL-5f4-tZ | GCTTAAACTATTTTGGGGGACT | 250 | |
| D11S1196 | cSRL-5f5 | nd | | 273 | cSRL-5f5-tA | ATACCTCAGGGACCTGCATG | 250 | 58 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | | | | cSRL-5f5-tZ | CAGAACTGGTGAGCAACAGC | 250 | |
| D11S1197 | cSRL-5f6 | nd | | 315 | cSRL-5F6-tA | GCAGGATGAAATGCACCC | 250 | 56 |
| | | | | | cSRL-5f6-tZ | TGAGGGGTCACCAGCAAT | 250 | |
| D11S1198 | cSRL-5f7 | 0.60–0.85 | b | 270 | cSRL-5f7-tA | CACTGGAGGAAAAGCCAAC | 500 | 56 |
| | | 11q14.1–q23.3 | | | cSRL-5f7-tZ | AAGCCCATACCCTCTTCTCA | 500 | |
| D11S1199 | cSRl-5f9 | 0.93–1.00 | b | 151 | cSRL-5f9-tA | GGTTGGGGTGGGAGAGAG | 500 | 56 |
| | | 11q24.1–q25 | | | cSRL-5f9-tZ | TTCAGGTGATGAAATGTGACA | 500 | |
| D11S1191 | cSRL-5f11 | 0.60–0.85 | b | 165 | cSRL-5f12-tA | GTTCCTTTTAGCTTCAGTGCTT | 500 | 56 |
| | | 11q14.1–q23.3 | | | cSRL-5f12-tZ | AGCAATCAATGCAATGAAACC | 500 | |
| D11S1200 | cSRL-5g1 | nd | | 166 | cSRL-5g1-tA | CCGGCCTCCTTTGCTACT | 500 | 56 |
| | | | | | cSRL-5g1-tZ | AGGTCCAGAAGAGGAGATGTTG | 500 | |
| D11S1203 | cSRL-5g2 | 0.05–0.24 | b | 293 | cSRL-5g2-tA | TTTTTCAGACCATTTTATTTGAATG | 833 | 56 |
| | | 11p15.4–p13 | | | cSRL-5g2-tZ | GAAATTTATACTACCCATGGGGC | 833 | |
| D11S1204 | cSRL-5g6 | 0.33–0.50 | b | 256 | cSRL-5g6-tA | GGGGGGTCTTCATTACCTTT | 833 | 56 |
| | | 11p11.2–q13.1 | | | cSRL-5g6-tZ | AGCTGACTGGACTCACTTTGG | 833 | |
| D11S1205 | cSRL-5g8 | 0.05–0.24 | b | 258 | cSRL-5g8-tA | CTCACCTGCCCTCTGCAC | 500 | 56 |
| | | 11p15.4–p13 | | | cSRL-5g8-tZ | CTACCTGGAGGGAGGGACTC | 500 | |
| D11S1206 | cSRL-5g9 | 0.05–0.24 | b | 335 | cSRL-5g9-tA | GGGGTTAAATACCACACAATGG | 833 | 52 |
| | | 11p15.4–p13 | | | cSRL-5g9-tZ | TGAGGGGAGTGTTAAGGCAC | 833 | |
| D11S1201 | cSRL-5g10 | 0.24–0.33 | b | 168 | cSRL-5g10-tA | ACCTGCACATCCTGCACAT | 500 | 56 |
| | | 11p13–p11.2 | | | cSRL-5g10-tZ | GCCATCTATTCCTGGAGAGAG | 500 | |
| D11S1202 | cSRL-5g11 | 0.33–0.50 | b | 150 | cSRL-5g11-tA | ACAAAAAATGGCAAGTAGACCA | 500 | 56 |
| | | 11p11.2–q13.1 | | | cSRL-5g11-tZ | AACAACTCTGGAGGGGTGG | 500 | |
| D11S1209 | cSRL-5h2 | 0.33–0.50 | b | 260 | cSRL-5h2-tA | TCGATGACCAGCCAACAATA | 500 | 56 |
| | | 11p11.2–q13.1 | | | cSRL-5h2-tZ | CCATGGGTCCAAGCAGAC | 500 | |
| D11S1210 | cSRL-5h3 | 0.85–0.93 | b | 302 | cSRL-5h3-tA | AAACCTGCCCAGGCCTAC | 250 | 56 |
| | | 11p23.3–q24.1 | | | cSRL-5h3-tZ | TGTGTTATGGGCCATGGTC | 250 | |
| D11S1211 | cSRL-5h4 | 0.60–0.85 | b | 273 | cSRL-5h4-tA | CCAAAAACCAGTACATCATCCA | 833 | 56 |
| | | 11q14.1–q23.3 | | | cSRL-5h4-tZ | CCACCAAATCCATGTTTTGA | 833 | |
| D11S1212 | cSRL-5h6 | 0.60–0.85 | b | 207 | cSRL-5h6-tA | TTTAGACCCACAAAAAGCAGTT | 833 | 52 |
| | | 11q14.1–q13.3 | | | cSRL-5h6-tZ | AAACGCAAACTTGGAAAGTTG | 833 | |
| D11S1213 | cSRL-5h7 | 0.05–0.24 | b | 271 | cSRL-5h7-tA | GGTGTAAGAGCTCCCTGCTG | 833 | 56 |
| | | 11p15.4–p13 | | | cSRL-5h7-tZ | GAGAGTCTGGACCAATCCCA | 833 | |
| D11S1214 | cSRL-5h9 | 0.24–0.33 | b | 285 | cSRL-5h9-tA | TGAAGCAAAACAGGGAATCC | 833 | 56 |
| | | 11p13–p11.2 | | | cSRL-5h9-tZ | TTTTTGGGCATGTCTGATCA | 833 | |
| D11S1207 | cSRL-5h10 | 0.60–0.85 | b | 328 | cSRL-5h10-tA | ATCCAAGGTCCCTGATAAACTT | 500 | 52 |
| | | 11q14.1–q23.3 | | | cSRL-5h10-tZ | GGAAAGGAAAAAGGGAAACT | 500 | |
| D11S1208 | cSRL-5h12 | 0.05–0.24 | b | 268 | cSRL-5h12-tA | ACTCCTAGCCACCCCAATCT | 500 | 56 |
| | | 11p15.4–p13 | | | cSRL-5h12-tZ | TACTGCGGTAGCTGCATGAC | 500 | |
| D11S1216 | cSRL-6a2 | 0.33–0.50 | b | 182 | cSRL-6a2-tA | CAGTGATTGCAACCTTGCAC | 833 | 56 |
| | | 11p11.2–q13.1 | | | cSRL-6a2-tZ | GGAGAGGAGAAAGGGTTGCT | 833 | |
| D11S1217 | cSRL-6a3 | 0.33–0.50 | b | 267 | cSRL-6a3-tA | CGCCTGCCAGTAGTTGAAGT | 500 | 56 |
| | | 11p11.2–q13.1 | | | cSRL-6a3-tZ | GATGCCGTCCAAATCTGG | 500 | |
| D11S1218 | cSRL-6a4 | 0.85–0.93 | b | 318 | cSRL-6a4-tA | CGAGCACTCTTTCAGTCTCAA | 833 | 56 |
| | | 11p23.3–q24.1 | | | cSRL-6a4-tZ | TCAGCATGCATTTATCGAGC | 833 | |
| D11S1219 | cSRL-6a5 | 0.33–0.50 | b | 205 | cSRL-6a5-tA | TAGGCTCAAATCAACCAAGTCA | 833 | 56 |
| | | 11p11.2–q13.1 | | | cSRL-6a5-tZ | AGATGGGGTCTCACTGTTGC | 833 | |
| D11S1220 | cSRL-6a6 | 0.05–0.24 | b | 180 | cSRL-6a6-tA | CCTCTGCCAACAATCTGGTT | 500 | 56 |
| | | 11p15.4–p13 | | | cSRL-6a6-tZ | AGTAGAAGCATAGCATTTGCCA | 500 | |
| D11S1221 | cSRL-6a7 | 0.33–0.50 | b | 306 | cSRL-6a7-tA | GTGTTTTTTGAGACAGTCTCGCT | 500 | 56 |
| | | 11p11.2–q13.1 | | | cSRL-6a7-tZ | CCTCAGAAGTTTGCTGGTTAAGA | 500 | |
| D11S1215 | cSRL-6a12 | 0.60–0.85 | b | 220 | cSRL-6a12-tA | ACTGCTTCTGACAGCAATTGA | 833 | 56 |
| | | 11q14.1–q23.3 | | | cSRL-6a12-tZ | TTCCCAGGTCAAATATTGGTG | 833 | |
| D11S1222 | cSRL-6b1 | 0.05–0.24 | b | 151 | cSRL-6b1-tA | GCATCTGTGCAGTCTTCTGC | 833 | 52 |
| | | 11p15.4–p13 | | | cSRL-6b1-tZ | TAGTGGGCAGTCAGTGCTTG | 833 | |
| D11S1225 | cSRL-6b2 | 0.33–0.50 | b | 276 | cSRL-6b2-tA | TGGCTGCTCTGCTTTTTACC | 833 | 52 |
| | | 11p11.2–q13.1 | | | cSRL-6b2-tZ | AAGTGTGCACTACCTTGTCACC | 833 | |
| D11S1226 | cSRL-6b7 | 0.50–0.50 | b | 306 | cSRL-6b7-tA | CTGGATGGCAGAGAGAAAC | 250 | 56 |
| | | 11q13.1 | | | cSRL-6b7-tZ | ATACCCTCAGTGCCCAACAG | 250 | |
| D11S1227 | cSRL-6b9 | 0.33–0.50 | b | 205 | cSRL-6b9-tA | CTCAAGCTCTGGTGACTTTGG | 833 | 52 |
| | | 11p11.2–q13.1 | | | cSRL-6b9-tZ | GGAATGCTACTGGAGAGATTCA | 833 | |
| D11S1223 | cSRL-6b10 | 0.33–0.50 | b | 151 | cSRL-6b10-tA | TAACAGAGCAGTCTATGGCACC | 833 | 52 |
| | | 11p11.2–q13.1 | | | cSRL-6b10-tZ | AATCTGTAAAGTCAGCATCCCC | 833 | |
| D11S1224 | cSRL-6b12 | 0.60–0.85 | b | 274 | cSRL-6b12-tA | CAAGAACATGGCAATTAACCC | 833 | 52 |
| | | 11q14.1–q23.3 | | | cSRL-6b12-tZ | CACCACGTAACCTCAGCAGA | 833 | |
| D11S1228 | cSRL-6c1 | nd | | 271 | cSRL-6c1-tA | GGCAACCAAGAGGGAAACTT | 833 | 52 |
| | | | | | cSRL-6c1-tZ | AGAAGTGCTCTGTCCTCTGACA | 833 | |
| D11S1231 | cSRL-6c2 | 0.50–0.85 | b | 336 | cSRL-6c2-tA | AGACATTGGCCTGGTTCTTG | 250 | 56 |
| | | 11q13.1–q23.3 | | | cSRL-6c2-tZ | CCCAGTGCCAGGCTTGTC | 250 | |
| D11S1232 | cSRL-6c4 | 0.85–0.85 | b | 335 | cSRL-6c4-tA | CCCATTCAGTTCAAGCTTCTC | 500 | 58 |

TABLE 5-continued

STS MAP OF CHROMOSOME 11
Chromosome 11 specific STSs, mapping positions, technique[a], product size, primer names,
sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | 11q23.3 | | | cSRL-7c4-tZ | CCTGGACATAACCCCATTGT | 500 | |
| D11S1233 | cSRL-6c8 | 0.50–0.60 | b | 180 | cSRL-6c8-tA | CCCTATTACTCAGGACCCACC | 500 | 56 |
| | | 11q13.1–q14.1 | | | cSRL-6c8-tZ | CACTGCTTTATCCCGCCTAG | 500 | |
| D11S1229 | cSRL-6c11 | nd | | 275 | cSRL-6c11-tA | GAGCTCAGGCTAACCTGTGG | 500 | 56 |
| | | | | | cSRL-6c11-tZ | GTATCAGTTAGCTTTTGCTGCC | 500 | |
| D11S1230 | cSRL-6c12 | 0.50–0.85 | b | 256 | cSRL-6c12-tA | GCACAGACTCCCTTGGACAT | 500 | 56 |
| | | 11q13.1–q23.3 | | | cSRL-6c12-tZ | GTTCCCCTGTAAGGAATGAGC | 500 | |
| D11S1234 | ySL-A109g11 | nd | | 180 | SLA109g11-A | GTGCATATTGAACCAGATGGGCGGG | 500 | 51 |
| | | | | | SLA109g11-Z | TGGACCTGCTTGGTACAAGGACCGA | 500 | |
| D11S1235 | ySL-A109G4 | 0.85–0.85 | b | 106 | SLA109g4-A | GCACCAGTCCTGGCCTAGAAGATTGTGGTC | 250 | 54 |
| | | 11q23.3 | | | SLA109g4-Z | TAGCTGGATCTGAAAGCTGCAGGGGCTC | 250 | |
| D11S1236 | ySL-A13E4 | 0.91–0.93 | a | 192 | SLA13E4-A | GGCCGTGTTAAAGCTGGAAGATGTGAG | 250 | 56 |
| | | 11q24.1 | | | SLA13E4-Z | ATGATTGGTTATGCTGATTATCTGTTCCAA | 250 | |
| D11S1237 | ySL-A77g8 | 0.91–0.92 | ab | 337 | SLA77G8-A | GTGTAGTACAAAGGCAGAGTG | 250 | 54 |
| | | 11q24.1 | | | SLA77G8-Z | CTAGGGAGAGGTGCCATTCAA | 250 | |
| D11S1238 | ySL-B215B10 | 0.58–0.55 | ab | 185 | SLB215B10-A | ACTCGATGAAGGTTCCATGGGTGGA | 833 | 54 |
| | | 11q13.5–q13.3 | | | SLB215B10-Z | TCTGTGCCCATAGAAGGGACCTAGG | 833 | |
| D11S1239 | ySL-B34g9 | 0.85–0.87 | ab | 160 | SLB34G9-A | GCCTGGACTAGGCAAATGGTCTCTCATTCC | 250 | 56 |
| | | 11q23.3 | | | SLB34G9-Z | TGGGATTGTCAAGAGTGGACCATGAGGATC | 250 | |
| ACP2 | | 0.33–0.40 | bc | 44 | ACP2-B | CCTCCTCATAGTGCTGCTCC | 250 | 58 |
| | | 11p11.2–p11.11 | | | ACP2-Y | GATAGAAGTGCAAGGTGGATCC | 250 | |
| ACRV1 | | nd | | 202 | ACRV1-A | CTTGCTTGTTTTGACTCAGGC | 500 | 58 |
| | | | | | ACRV1-Z | AGAGAAAGAGTTGGAGCAGGG | 500 | |
| ACTN3 | | 0.33–0.50 | b | 164 | ACTN3-A | CTGGACTACGTGGCCTTCTC | 833 | 58 |
| | | 11p11.2–q13.1 | | | ACTN3-Z | TTCAGAAGCACTTGGCTGG | 833 | |
| AHNAK | | 0.00–0.40 | c | 159 | AHNAK-A | TGCCAGATGTTGACATTAAAGG | 250 | 58 |
| | | 11p15.5–p11.11 | | | AHNAK-Z | GCAGCTTCACATCCACTTCA | 250 | |
| AN2 | | 0.23–0.27 | bc | 870 | AN2-A | TGAATGGGCGGAGTTATGAT | 250 | 60 |
| | | 11p13 | | | AN2-Z | TATCAGGTTCACTTCCGGGA | 250 | |
| APOA1 | | 0.85–0.87 | abc | 258 | PCR-Al.1 | CACCCGGGAGACCTGCAAGC | 833 | 56 |
| | | 11q23.3 | | | PCR-Al.2 | TCTAAGCAGCCAGCTCTTGCA | 833 | |
| BCL1 | | 0.52–0.55 | c | 205 | BCL1(1) | GCTAATCACAGTCTAACCGA | 833 | 52 |
| | | 11q13.3 | | | BCL1(2) | TTGCACTGTCTTGGATGCA | 833 | |
| BDNF | | 0.23–0.24 | bc | 579 | BDNF-A | CAGGCCACTGCTGTTCCT | 833 | 56 |
| | | 11p13 | | | BDNF-Z | ACCTTGTCCTCGGATGTTTG | 833 | |
| C1NH | | 0.42–0.50 | bc | 48 | C1NH-A | ATCCTGGAGGTTTCCAGCTT | 833 | 56 |
| | | 11q12.1–q13.1 | | | C1NH-Z | TGTCCAACAAATGACCTGGA | 833 | |
| CALCA | | 0.09–0.05 | bc | 425 | CALCA-A | CTCAGGCACAGTGGAACTGA | 833 | 56 |
| | | 11p15.2–p15.4 | | | CALCA-Z | GTCCCAGAGACATTCTATTCCG | 833 | |
| CALCB | | 0.09–0.13 | bc | 381 | CALCB-B | AGAGGGACCACTACCCGACT | 833 | 56 |
| | | 11p15.2–p15.1 | | | CALCB-Y | AGCACCGCAGCTCAGTTC | 833 | |
| CALCP | | 0.09–0.13 | bc | 150 | CALCP-A | CTTCCCCTCCACAGGTCT | 250 | 58 |
| | | 11p15.2–p15.1 | | | CALCP-Z | CTGGAGCTCTGTCTCCTGCT | 250 | |
| CAT | | 0.24–0.27 | bc | 563 | CAT-A | AAACAGAATGCGATTCACACC | 833 | 56 |
| | | 11p13 | | | CAT-Z | ATTAAGCCATGACGGTGTC | 833 | |
| CCND1 | | 0.48–0.50 | bc | 219 | PRAD1-A | CAGGCTGTGTCCCCTCTTCTC | 250 | 56 |
| | | 11q13.1 | | | PRAD1-Z | CAGAAGCTATTCCAATCATCCC | 250 | |
| CD20 | | 0.48–0.52 | c | 158 | CD20(1) | CAGCAGGGATCTATGCACCCATCG | 833 | 44 |
| | | 11q13.1 | | | CD20(2) | TCTGGCATATCCCTGTGGAGCCTTT | 833 | |
| CD3D | | 0.87–0.89 | abc | 800 | CD3(1) | AAGGTATTTTGGCCCAGTCAATCAAAGGT | 833 | 55 |
| | | 11q23.3 | | | CD3(2) | AGTCATACACCCTTAACCAAGTGGTTTCC | 833 | |
| CD44 | | 0.24–0.27 | bc | 150 | CD44-A | GCAGAATGTGGACATGAAGA | 500 | 56 |
| | | 11p13 | | | CD44-Z | ATGCTAAAAAGATTCGCAATG | 500 | |
| CD5 | | 0.48–0.50 | bc | 950 | CD5-A | GAGCTCAATCATCTGCTACGG | 833 | 56 |
| | | 11q13.1 | | | CD5-Z | TGCCGCTGTAGAACTCCAC | 833 | |
| CHRM1 | | 0.42–0.59 | c | 543 | CHRM1-B | CAGTGACAGGCAACCTGCT | 250 | 60 |
| | | 11q12.1–q13.5 | | | CHRM1-Y | GTGCTCGGTTCTCTGTCTCC | 250 | |
| CHRM4 | | 0.27–0.37 | c | 417 | CHRM4-A | CTCACTCTCTCATCACCCTGC | 833 | 50 |
| | | 11p12–p11.2 | | | CHRM4-Z | TAGCGATTGTGGGATGATGA | 833 | |
| CK2A | | 0.24–0.50 | b | 184 | CK2A-A | ACAAGGTCTTACCCCCAGCT | 500 | 58 |
| | | 11p13–q13.1 | | | CK2A-Z | TTCCACCACATGTGACTCGT | 500 | |
| CLG | | 0.68–0.70 | bc | 461 | CLG-A | TTATGACCATCAGAACCAGCC | 833 | 56 |
| | | 11q21 | | | CLG-Z | CTGTGAGACACCACACCCC | 833 | |
| CLG1 | | 0.68–0.78 | bc | 171 | CLG1-A | TAACCCCAGGTACCCATGAA | 500 | 56 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | 11p21–q22.3 | | | CLG1-Z | TCTGTCTTCACACGGCCTC | 500 | |
| CNTF | CNTF1 | 0.41–0.52 | a | 486 | CNTFS | GTGAAGCATCAGGGCCTGAAC | 250 | 56 |
| | | 11q11–q13.1 | | | CNTFALPHA | CATTTTCTTGTTGTTAGCAAT | 250 | |
| COX8 | | 0.48–0.59 | c | 241 | COX(1) | GGGCTTACCTCCTGCTTCGTGACCTTCCTC | 833 | 65 |
| | | 11q13.1–q13.5 | | | COX(2) | GAGGTCATGATTGCAGAAGAGGTGACTGGA | 833 | |
| CRYAB | CRYA2 | 0.75–0.82 | bc | 441 | CRYA2-A | GGTTTGCACGTTTCCACAC | 833 | 56 |
| | | 11q22.3–q23.1 | | | CRYA2-Z | CTGCTACAGAGTCAGGAATCCC | 833 | |
| D11S149 | | 0.33–0.37 | bc | 135 | D11S149(1/1) | AGGCAGATAACTTACAAAATCCTA | 833 | 60 |
| | | 11p11.2 | | | D11S149(2/2) | TGCTGGCAAACTCGTTTCTGTCCT | 833 | |
| D11S325 | | 0.24–0.27 | bc | 750 | D11S325.PCR1.1 | GACAGACACAGAGGAGAGAATGAATATAT | 250 | 56 |
| | | 11p13 | | | D11S325.PCR1.2 | CCAGTGCAGCAGAAGCAAAGCGCGG | 250 | |
| D11S35 | | 0.70–0.78 | bc | 165 | 780 | ACAATTGGATTACTACTAGC | 833 | 52 |
| | | 1q22.1–q22.3 | | | 781 | TGTATTTGTATCGATTAACC | 833 | |
| D11S367 | | 0.85–0.84 | abc | 203 | D11S367-A | GACCTGCGTGTGTTTGTGCTCTGTGT | 250 | 56 |
| | | 11q23.3 | | | D11S367-Z | TTCTTCACTGGAGGTAGAAGCAGCCC | 250 | |
| D11S384 | | 0.78–0.78 | abc | 273 | cj193 5' | GACGGGCTAACTGATGTCTAC | 500 | 56 |
| | | 11q23.1 | | | cj193 3' | ATTAGCCAAGCAGTTGCCAGC | 500 | |
| D11S419 | | 0.05–0.24 | bc | 112 | Mfd58CA | CTCATTTGAAGACTGCAGCA | 833 | 56 |
| | | 11p15.4–p13 | | | Mfd58GT | AGGGCTTCCTGTCCATCTA | 833 | |
| D11S420 | | 0.89–0.92 | abc | 280 | 506 | AGTTACACCGGTTCTGCAGA | 833 | 50 |
| | | 11q23.3–q24.1 | | | 507 | GATTAATGATAGTGCTATCC | 833 | |
| D11S490 | | 0.85–0.87 | abc | 150 | 22314 | CACAAACATTGGCGCAT | 160 | 50 |
| | | 11q23.3 | | | 41919 | TTCTGGGTCACGGTGCTTCA | 160 | |
| D11S528 | | 0.85–0.91 | bc | 73 | 42026 | AATGGTGTCCCCACACATGT | 833 | 55 |
| | | 11q23.3 | | | 42027 | TCCTACCTACCGAGCTTAAA | 833 | |
| D11S533 | | 0.48–0.59 | c | 500 | D11S533.PCR1.1 | GCCTAGTCCCTGGGTGTGGTC | 500 | 58 |
| | | 11q13.1–q13.5 | | | D11S533.PCR1.2 | GGGGCTCTGGGAACATGTCCC | 500 | |
| D11S534 | | 0.50–0.59 | b | 200 | 91249 | ATATGGAAACTCTCCGTACT | 500 | 56 |
| | | 11q13.1–q13.5 | | | 92005 | GCAACCATGGAGAGTCTGGA | 500 | |
| D11S790 | | 0.55–0.55 | a | 450 | c11q-3h10-uA | GTAGTTGTGGGCGAGGGTAA | 500 | 56 |
| | | 11q13.3 | | | c11q-3h10-uZ | AAACAATCCCTTCCTCGCC | 500 | |
| D11S860 | | 0.00–0.13 | c | 154 | BS4BL | TAGTATTGCCATAGAAGAAGC | 833 | 55 |
| | | 11p15.5–p15.1 | | | BS48R | GCAACACGTACACACTGAGACA | 833 | |
| D11S861 | | 0.05–0.24 | b | 154 | A136-1 | CTGAAACCAAGTGAAAAGGAGA | 250 | 55 |
| | | 11p15.4–p13 | | | A136.2 | AAGCTCCATTGTCTTCTGGC | 250 | |
| D11S862 | | 0.60–0.85 | b | 152 | MS7-1 | TACCATATTAAATCACCCACATGG | 833 | 58 |
| | | 11q14.1–q23.3 | | | MS7-2 | GGAATCAGGATTCAAACTCTGG | 833 | |
| D11S863 | | nd | | 13 | MS20-1 | GCAACATGGTAAGAGTCCAGC | 833 | 60 |
| | | | | | MS20-2 | GTAGCTGGGACCAGAGGGAT | 833 | |
| D11S865 | | nd | | 170 | E137-1 | CTTTTTGTTGCCCATTGCTT | 833 | 58 |
| | | | | | E137-2 | GTAAAGGATAAAAACTCTGCAGGC | 833 | |
| D11S860E | | nd | | 277 | AA12a | AGTGATCTCTGAGAAAAGGG | 500 | 55 |
| | | | | | AA12B | ATATTGTGAATGACTAGGG | 500 | |
| D11S870 | | 0.50–0.85 | bc | 154 | 349 | ATTTTGGATGAGCCAAGCCT | 500 | 55 |
| | | 11q13.1–q23.3 | | | 350 | ATCTGTATATATGTGTACCTG | 500 | |
| D11S872 | | 0.93–1.00 | BC | 158 | 291 | GATCCTGTCTCAAACACAAAC | 833 | 56 |
| | | 11q24.1–q25 | | | 401 | AAGTCTTCAGCTTTATCAAC | 833 | |
| D11S873 | | 0.50–0.85 | bc | 176 | 489 | CCTGGTTTAGAATAATACCT | 833 | 54 |
| | | 11q13.1–q23.3 | | | 490 | ATAATGTACTGTGATAAATGCT | 833 | |
| D11S874 | | nd | | 156 | 583 | GGTTTAAAAAGTCAGCCCTC | 500 | 56 |
| | | | | | 584 | AATCATTTTCAAGCATAGGC | 500 | |
| D11S875 | | 0.05–0.24 | bc | 103 | 599 | ACTGTCCTCTCATCCTACTG | 833 | 56 |
| | | 11p15.4–p13 | | | 600 | TACAGAGCTGAGTTTGTAGC | 833 | |
| D11S876 | | 0.60–0.85 | bc | 216 | 791 | TGGAGATGTGCCATAGAGGT | 250 | 56 |
| | | 11q14.1–q23.3 | | | 792 | TCAGGAAAACTGCCTGAGG | 250 | |
| D11S943E | | 0.85–0.93 | bc | 103 | 307 | CAACGGAACAGGAGTCCTT | 833 | 56 |
| | | 11q23.3–q24.1 | | | 308 | GCTTCTGAGACTTCAATCTA | 833 | |
| D11S944E | | 0.50–0.85 | bc | 117 | 139 | GTTTGAAGGAAGTGATTTCC | 833 | 56 |
| | | 11q13.1–q23.3 | | | 140 | TAGGGCCACCTCCAGTTCAT | 833 | |
| D11S950E | | 0.93–1.00 | b | 242 | est00111-A | GAATGTAGCCTCAAAAGGATGG | 250 | 57 |
| | | 11q24.1–q25 | | | est00111-Z | CCAGTTCAATTTAGCCTTCAGG | 250 | |
| D11S952E | | 0.33–0.50 | bc | 115 | 339 | TTTCGAAGAAGGCAGTTTG | 833 | 56 |
| | | 11p11.2–q13.1 | | | 340 | ATCAGCCAGAGGCCTGACT | 833 | |
| D11S953E | | 0.60–0.85 | b | 136 | est00016-A | GCTACTACGATGCCATGGGT | 250 | 56 |
| | | 11q14.1–q23.3 | | | est00016-Z | TTACGATAATGACATTTCTTCTGG | 250 | |
| D11S956 | | 0.33–0.50 | bc | 247 | sMSH3A | GATCAGTAATTAGCCAGACTCTAGG | 250 | 56 |
| | | 11p11.2–q13.1 | | | sMSH3B | GGTTTTGGAGCTTAAGGAGG | 250 | |
| D11S964 | | nd | | 291 | UT544a | ACTTCAGCCTCGGTGACAG | 833 | 56 |
| | | | | | UT544b | TGTTCTGCCTCTGTTGTTAC | 833 | |
| D11S968 | | 0.93–1.00 | b | 150 | AFM109xc3a | GGCTCTTGTAGTTTCTTATCTCCT | 833 | 52 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
|  |  | 11q24.1–q25 |  |  | AFM109xc3m | AAGGCGGATGCTGGAC | 833 |  |
| D11S969 |  | 0.93–1.00 | b | 150 | AFM205vf10a | TTGATTTGGAAGATTTTCAC | 833 | 49 |
|  |  | 11q24.1–q25 |  |  | AFM205vf10m | GGGGCAGAATGGGTAT | 833 |  |
| DRD2 |  | 0.79–0.82 | ac | 283 | JHE20 | CTCCTTCTGCTGGGAGAGCTTCCTACGGCT | 500 | 66 |
|  |  | 11q23.1 |  |  | JHE21 | CGAGCCCAGGAGCTGGAGATGGAGATGGAG | 500 |  |
| DRD4 |  | 0.00–0.03 | c | 478 | DRD4-A | AGCTTATAAGAGGCTGCTGGG | 250 | 58 |
|  |  | 11p15.5 |  |  | DRD4-Z | TTTTTTGGATGGATTTGTTTCC | 250 |  |
| FDX1 |  | 0.60–0.59 | bc | 461 | FDX1-A | CTGTTCGAGTGCCTGAAACA | 833 | 56 |
|  |  | 11q14.1–q13.5 |  |  | FDX1-Z | GTATGGCCCTAAACAAGCCA | 833 |  |
| FGF4 |  | 0.52–0.55 | c | 310 | HST(1) | CAGTGTTGGAACTGCGGGCTTGAGGTGGA | 833 | 52 |
|  |  | 11q13.3 |  |  | HST(2/2) | AGGAGAATCTCCTTGAACGTGCACTCATCG | 833 |  |
| FLI1 |  | 0.93–0.94 | ac | 377 | EW1S | AGTCTCCTAGCATCTTGTGAGTTGCAT | 250 | 58 |
|  |  | 11q24.1–q24.3 |  |  | EW2A | GRGGRCAGCTGAGTGCATACTGTCCAC | 250 |  |
| FOLR1 |  | 0.52–0.60 | bc | 300 | FOLR1-A | CGGCATTTCATCCAGGAC | 250 | 57 |
|  |  | 11q13.3–q14.1 |  |  | FOLR1-Z | GGTGTAGGAGGTGCGACAAT | 250 |  |
| FSHB |  | 0.24–0.26 | ac | 409 | FSHB-A | ATAAGGACCCAGCCAGGC | 833 | 58 |
|  |  | 11p13 |  |  | FSHB-Z | CATGATGCAGTCCTGGCC | 833 |  |
| FTH1 |  | 0.48–0.59 | c | 284 | FTH1-A | TGCTTCAACAGTGCTTGGAC | 250 | 56 |
|  |  | 11q13.1–q13.5 |  |  | FTH1-Z | GCACAGGTAAACGTAGGAGGC | 250 |  |
| GIF |  | 0.33–0.50 | B | 214 | GIF-A | GGGGAAATTCCACAACCC | 166 | 60 |
|  |  | 11p11.2–q13.1 |  |  | GIF-Z | GTTGAAGAGCAGCTCAACCC | 166 |  |
| GSTP1 | GST3 | 0.48–0.59 | c | 313 | GST(1) | CCTGCAGATCTCCTTCGCTGACTACAACCT | 833 | 65 |
|  |  | 11q13.1–q13.5 |  |  | GST(2) | AGAACGCCCTAAGCCCGTCCCAGGAAACAC | 833 |  |
| H19 |  | 0.00–0.05 | b | 440 | H19-A | TTGTCAGTAGAGTGCGCCC | 833 | 56 |
|  |  | 11q15.5–p15.4 |  |  | H19-Z | ACCTCCCTCAGGGTCCAG | 833 |  |
| HBB |  | 0.00–0.03 | c | 536 | KM29 | GGTTGGCCAATCTACTCCCAGG | 833 | 56 |
|  |  | 11p15.5 |  |  | RS42 | GCTCACTCAGTGTGGCAAAG | 833 |  |
| HPX |  | 0.00–0.05 | c | 454 | HPX-A | AGCTCAGCATGGCTAGGGTA | 500 | 58 |
|  |  | 11p15.5–p15.4 |  |  | HPX-Z | GTAGCATCAAAGCTCCAGCC | 500 |  |
| HRAS |  | 0.01–0.03 | abc | 312 | H3' | GGGTGCTGAGACGAGGGACT | 500 | 56 |
|  |  | 11p15.5 |  |  | H5' | GAGACCCTGTAGGAGGACCC | 500 | 56 |
| IL-1BCE |  | 0.78–0.91 | c | 157 | IL-1BCE-A | TTCATTTGAGCAGCAGATG | 500 | 60 |
|  |  | 11q23.1–q23.3 |  |  | IL-1BCE-Z | CCAAAAACTTTTACAGAACGA | 500 |  |
| INS |  | 0.01–0.03 | abc | 439 | INS-A | CCCTCATTTGATGACCGC | 500 | 58 |
|  |  | 11p15.5 |  |  | INS-Z | GGGACACAGGAGGACACAGT | 500 |  |
| INSL2 |  | 0.31–0.59 | c | 507 | INSL2-A | ACTGAGGCTTTTGCAAGGAA | 833 | 56 |
|  |  | 11p11.2–q13.5 |  |  | INSL2-Z | CATGCATGAATGAGCATTCC | 833 |  |
| KRN1 |  | 0.48–0.59 | c | 511 | KRN1-A | CTTGTGGCTGCTCCCAGT | 500 | 62 |
|  |  | 11P13.1–q13.5 |  |  | KRN1-Z | ACATATGGCGGCATGTGG | 500 |  |
| LDHA |  | 0.10–0.23 | bc | 523 | LDHA-A | TAGTGTTCCTTGCATTTTGGG | 500 | 56 |
|  |  | 11p15.1–p14.1 |  |  | LDHA-Z | ATCCCAGGATGTGACTCACTG | 500 |  |
| LDHC |  | 0.05–0.19 | bc | 150 | LDHC-A | ATTGTCACAGCAGGTGCAAG | 500 | 56 |
|  |  | 11p15.4–p14.3 |  |  | LDHC-Z | AGACTCACCTGGATTTGAAACA | 500 |  |
| MDU1 |  | 0.42–0.50 | bc | 182 | MDU1-A | GAAACTGGAGCCTCACGAAG | 833 | 56 |
|  |  | 11q12.1–q13.1 |  |  | MDU1-Z | AACACCCTATTTGGGGGTTC | 833 |  |
| MLP |  | 0.00–0.05 | b | 870 | MLP-A | ACAACTACCACTGCGATCCC | 166 | 56 |
|  |  | 11q15.5–p15.4 |  |  | MLP-Z | ACTGGTACACCTCCAGCCC | 166 |  |
| MUC2 |  | 0.00–0.03 | bc | 155 | MUC2-B | CATTCTCAACGACAACCCCT | 250 | 58 |
|  |  | 11p15.5 |  |  | MUC2-Y | GCAAGAGATGTTAGCTGCCC | 250 |  |
| MYOD1 |  | 0.05–0.13 | bc | 210 | MYOD1-B | TCGCAGACCTAACCCTGC | 500 | 55 |
|  |  | 11p15.4–p15.1 |  |  | MYOD1-Y | CAGAGATAAATACAGCCCCAGG | 500 |  |
| NCAM |  | 0.82–0.82 | abc | 470 | JHE312 | GGCGCCCGTAGAAGCAAAGCCAGAGTGCCA | 500 | 66 |
|  |  | 11q23.1 |  |  | JHE311 | CGTTTCTGAGCTTCCTAGATTCTTAATTTG | 500 |  |
| NFRKB | NF-RKB | 0.94–1.00 | c | 470 | 6380 | GTACATGCAGCTGATAGCCCTGCCAAGGCC | 833 | 60 |
|  |  | 11q25 |  |  | 6381 | GACGTGGACACAACCGTGGTGCTGACAGGG | 833 |  |
| NGK2 |  | 0.00–0.13 | a | 176 | NGK2-A | ATCATCTTCCTGGCTTGG | 500 | 56 |
|  |  | 11p15.5–p15.1 |  |  | NGK2-Z | TACATGTCTCCATAGCCCAGG | 500 |  |
| OSBP |  | 0.40–0.42 | bc | 156 | OSBP-A | ATAGGGGAGAATACTGGGAGTG | 250 | 57 |
|  |  | 11q11 |  |  | OSBP-Z | GCACTTGGTAAGAGAGTCACAA | 250 |  |
| PBGD |  | 0.87–0.89 | abc | 406 | PBGD-A | CAAAGGAAGCGCCATAGAAG | 250 | 53 |
|  |  | 11q23.3 |  |  | PBGD-Z | CTGAGGATGGCAACCTGG | 250 |  |
| PC |  | 0.40–0.50 | bc | 125 | PC-B | CTCAGTGCCATGAAGATGGA | 250 | 56 |
|  |  | 11q11–q13.1 |  |  | PC-Y | CAAGATCACTCGATCTCCAGG | 250 |  |
| PGA3 |  | 0.40–0.59 | ac | 156 | PGA(1) | CTCATCAGAAAGAAGTCCTTCAGGCGCACC | 833 | 52 |
|  |  | 11q13.1–q13.5 |  |  | PGA(2/2) | ATCCAGGTAGTTCTCCAGGGGCTGTTCATC | 833 |  |
| PGA5 |  | 0.48–0.59 | c | 432 | PGA5-A | TGAGAGAACTACCCCTGAGACC | 500 | 50 |
|  |  | 11q13.1–q13.5 |  |  | PGA5-Z | ACCCCTCTAGTGGATGGTCC | 500 |  |
| PGR |  | 0.70–0.78 | bc | 504 | PGR-A | TGGCACACAACATCCAAACT | 250 | 56 |
|  |  | 11q22.1–q22.3 |  |  | PGR-Z | CAAGCCTCCTCCTCTAGG | 250 |  |
| PPP1CA | PPP1A | 0.48–0.59 | c | 208 | PP1(1/2) | GAAGTACGGGCAGTTCAGTGGCCT | 833 | 60 |

TABLE 5-continued

STS MAP OF CHROMOSOME 11
Chromosome 11 specific STSs, mapping positions, technique[a], product size, primer names, sequences, concentrations and annealing temperatures

| Locus Name | STS Name (if different) | FLpter range band(s) | Map tech. | Product size (bp) | Primer name | Primer sequence | [primer] (nM) | Annealing temp. (°C.) |
|---|---|---|---|---|---|---|---|---|
| | | 11q13.1–q13.5 | | | PP1(2/2) | ATACACCAAGGTCCATGTTCCCCGT | 833 | |
| PROS30 | | 0.05–0.24 | b | 165 | PROS30-A | TGCTCAACCTGCTGATGAAC | 250 | 54 |
| | | 11p15.4–p13 | | | PROS30-Z | TAGCATTCCACCACTCTGCA | 250 | |
| PTH | | 0.09–0.12 | abc | 528 | PTH-A | CTCGTGAAAACCAACCCAAT | 833 | 60 |
| | | 11p15.2–p15.1 | | | PTH-Z | TCACATCAGCTTTGTCTGCC | 833 | |
| PYGM | | 0.47–0.49 | abc | 431 | PYGM-A | CTCCTCTCCTCCCCTTGC | 250 | 56 |
| | | 11q12.3–q13.1 | | | PYGM-Z | TCTCATAGTAGTGCTGCTGCG | 250 | |
| RAG1 | | 0.24–0.33 | b | 237 | RAG1-B | ATCAGGACAACTTTGAGAAAATCA | 833 | 52 |
| | | 11p13–p11.2 | | | RAG1-Y | TGGAAACTCTAAATTTCTTGAAATG | 833 | |
| RBTNL1 | | 0.23–0.27 | c | 152 | RBTNL1-A | ATCGGGGACCGCTACTTC | 833 | 56 |
| | | 11p13 | | | RBTBL1-Z | TACCTGAGATAGTCTCTCCGGC | 833 | |
| RNAHX | | 0.83–0.91 | c | 175 | RNAHX-A | CTGTGACACATCGTTTTGGG | 833 | 58 |
| | | 11q23.3 | | | RNAHX-Z | AGCACACAGTGCAAACAAGTG | 833 | |
| RNH | | 0.00–0.03 | c | 141 | RAI-A | TTCCTGCTGCTGCTCTCC | 250 | 57 |
| | | 11p15.5 | | | RAI-Z | TGTCCAAAATATACTGGCAGAA | 250 | |
| RRM1 | | 0.00–0.05 | c | 250 | RRM1-A | TTGCTTGAGGTGGTAAGGCT | 833 | 54 |
| | | 11p15.5–p15.4 | | | RRM1-Z | TGCTAAATGGGTAGATGAACC | 833 | |
| SAA | | 0.10–0.23 | bc | 469 | SAA-B | CACCTGGGAATACCAGTGCT | 500 | 48 |
| | | 11p15.1–p14.1 | | | SAA-Y | AAGGAACGAAAAGAAGCTTCG | 500 | |
| SMPD1 | | 0.03–0.05 | bc | 245 | SMPD1-B | AAGAACCAGTCCCTGGGC | 250 | 56 |
| | | 11p15.4 | | | SMPD1-Y | TCGCAGCAGCAGTACAGG | 250 | |
| SPI1 | | 0.27–0.31 | c | 218 | SPI1-A | ACCAGTTCCTGTTGGACCTG | 500 | 56 |
| | | 11p12 | | | SPI1-Z | CTTCACCTTCTTGACCTCGC | 500 | |
| SRPR | | 0.91–0.92 | abc | 150 | SRPR-A | GTGGCATGTTTGGTATGCTG | 500 | 56 |
| | | 11q24.1 | | | SRPR-Z | TGGCAACAGATTCACAGAGC | 500 | |
| SSRP1 | | 0.33–0.50 | b | 162 | SSRP1-A | TFCCATCTGAACATGCTCTC | 250 | 57 |
| | | 11p11.2–q13.1 | | | SSRP1-Z | GGTCGGGAAAGTAAGATGAGG | 250 | |
| STMY1 | | 0.75–0.78 | abc | 270 | STMY1-A | TGTAGAAGGCACAATATGGGC | 833 | 56 |
| | | 11q22.3 | | | STMY1-Z | GCAAGCTAAGCAGCAGCC | 833 | |
| STMY2 | | 0.76–0.70 | bc | 185 | STMY2-A | GGGGGAAGACAGATATGGGT | 833 | 56 |
| | | 11q22.3–q21 | | | STMY2-Z | CTGTTCAGTGCAATTCAAAAGC | 833 | |
| TCN1 | | 0.40–0.48 | bc | 161 | TCN1-B | TGGTAGTTACGTTGTCCGCA | 833 | 56 |
| | | 11q11–q12.3 | | | TCN1-Y | TCTCCTGCTCGTACTGGGAT | 833 | |
| TH | | 0.03–0.03 | bc | 230 | TH-A | CCTGGTCCTGCACTGTCC | 250 | 61 |
| | | 11p15.5 | | | TH-Z | CAGCAGACAGTGTCAGGGAA | 250 | |
| TPH | | 0.10–0.19 | bc | 153 | TPH-A | GCGTCCATTTGGAGTGAAGT | 833 | 57 |
| | | 11p15.1–p14.3 | | | TPH-Z | TAGATACTCGGCTTCCTGCTG | 833 | |
| TTG2 | | 0.4–0.33 | b | 160 | TTG2-A | TTGTTGTGACTTTGACGCTTG | 833 | 58 |
| | | 11p13–p11.2 | | | TTG2-Z | TTAAGGCCTTGGGAAGGG | 833 | |
| TYR | | 0.68–0.68 | abc | 507 | TYR-A | GTGACTCCAATTAGCCAGTTCC | 833 | 56 |
| | | 11q21 | | | TYR-Z | TGGGGATGACATAGTCTGAGC | 833 | |
| D11S1003 | ZNF1 | 0.83–0.88 | a | 195 | ZNF1-A | TGAAGGCATACACCATTGTCA | 250 | 50 |
| | | 11q23.2–q23.3 | | | ZNF1-Z | AATACACCGAATCCCAGCAG | 250 | |
| D11S1007 | ZNF6 | 0.65–0.56 | ab | 178 | ZNF6-A | TTCCGTATCTCCTCCTGCC | 833 | 58 |
| | | 11q13.3–q13.4 | | | ZNF6-Z | TCCCCTCTCTTCCCCAAC | 833 | |

[a]Locations of loci were were determined by FISH(a), cell hybrid analysis(b), and from the GDB(c). Those without regional mapping information are shown as nd.

Data Analysis

As described above, 371 Dna sequences fragments, determined at one pass accuracy, comprising 116 kb of chromosome 11 derived from cosmid ends were analyzed for the presence of repetitive sequences, simple sequences repeats and similarities to known genes. All of the sequence fragments were subjected to computer analyses for the presence of noteworty sequence structure (Table 6). The presence of repetitive sequence was determined using the program FASTA and a repetitive sequence database (Jurka et al., 1992, J. Mol. Evol. 35, 286–291) supplemented with a comprehensive set of di- and tri-nucleotide repeats. A FASTA cutoff score of 100 determined visually was used to recognize repetitive sequences from background random matches. Similarities to known genes were identified with the program BLAST and the GenBank database.

Amino acid comparisons were performed by translating DNA sequence fragments into all six potential reading frames and comparing translations to protein sequences in the Swiss-Prot, GenPept or PIR databases using the program BLASTX. Putative exons were identified using the program GRAIL on the Oak Ridge National Laboratory Internet server. The results of these various searches were evaluated numerically and by inspection. The data associated with this project, including DNA sequence file pointers, predicted STS primer sequences, test and mapping results, and in situ hybridization analysis, werer stored in a relational database called Genome Notebook specifically designed for this project. DNA sequence and mapping information on other genes was imported inton the Genome Notebook database from GDB and Genbank.

TABLE 6

STS MAP OF CHROMOSOME 11
Analysis of 371 random cosmid end sequences determined by automated fluorescent sequencing

| Category | percentage | | |
|---|---|---|---|
| subcategory | number | total | category |
| Contain repetitive DNA | 150 | 40% | |
| Alu | 60 | 16% | (40%) |
| LINE-1 | 41 | 11% | (27%) |
| Middle element repetitive | 17 | 5% | (11%) |
| CA repeats | 7 | 2% | (5%) |
| others | 27 | 7% | (18%) |
| Grail predicted exons | 34 | 9% | |
| Excellent | 6 | 2% | (18%) |
| Good | 9 | 2% | (26%) |
| Marginal | 19 | 5% | (55%) |
| Matches to protein sequences | 29 | 8% | |
| Certain | 7 | 2% | (24%) |
| Probable | 2 | 1% | (7%) |
| Likely | 2 | 1% | (7%) |
| Possible | 8 | 2% | (28%) |
| Marginal | 10 | 3% | (35%) |

Note: Repetitive sequence analysis was carried out using FASTA and a customized repetitive sequence database. Similarities to known proteins was determined using BLASTX. Putative exons were determined using GRAIL. The frequency of a sequence fragment containing the element is shown in bold and subtypes of repetitive DNA, potential exons and sequence match quality is shown as well as percentage of total. The last column shows the percentage of sequences within each category The results indicate that the average lenght of reliable sequence was 312 nucleotides with a standard deviation of 46 neclootides. Repetitive DNA sequences of some type were found in 150 of these sequences with Alu elements (40%) and LINE-1 sequences (27%) being the most frequent. Middle element repetitive sequences (11%) and simple sequence (CA)n repeats (5%) were also detected with reasonable frequency. The neutral net based program, GRAIL, was utilized to predict the locations of possible exons and detect putative genes in 34 sequences (9%); half of these were rated excellent or good according to reliability estimates used by this program. Analysis for additional positive gene sequences was carried out by computer searches for identity or similarity matches at the nucleotide and amino acid level. Significant matches to known protein sequences were detected for twenty-nine (8%) of the sequence fragments (see, e.g., Table 7).

TABLE 7

STS MAP OF CHROMOSOME 11
Results of searching the six-potential coding frames of 371 cosmid end sequences against the protein sequence databases with BLAST-X

| Likely significance sequence name | map position | potential homologue |
|---|---|---|
| Certain | | |
| D11S384[a] | 11q23.1 | mitochondrial acetoacetyl-CoA thiolase |
| c11q-2b11-t | 11q23.3 | UDP-N-acetylglucosamine-dolichyl-phosphate N-acetylglucosaminephosphotransferase |
| cSRL-2e4-t[b] | 11p15.4-p13 | postsynaptic density protein |
| cSRL-4a3-t[c] | — | Zinc finger protein ZFP-37 |
| cSRL-5f2-t | 11p15.5-p15.4 | retrovirus related POL polyprotein |
| cSRL-7d2-t | — | opioid binding protein/cell adhesion molecule |
| Probable | | |
| cSRL-2e4-t[b] | 11p15.4-p13 | discs-large tumor suppressor |
| cSRL-6g5-t | — | env polyprotein - feline endogenous virus ECE1 |
| Likely | | |
| cSRL-2c2-t | 11p11.2-q13.1 | mitochondrial carnitine palmitoyltransferase precursor |
| cSRL-2g6-t | 11p15.4-p13 | GATA-3 transcription factor |
| Possible | | |
| cSRL-2f5-t | 11p15.4-p13 | biglycan |
| cSRL-3a3-t | 11p13-p11.2 | cytochrome P450 IIA6 (Coumarin 7-hydroxylase). |
| cSRL-3a6-t | — | potassium channel protein |
| cSRL-4e2-t | — | phosphomannomutase |
| cSRL-4h2-t | — | properdin, mouse |
| cSRL-5b11-t | — | hypothetical 137.7 KD protein in subtelomeric Y' repeat |
| cSRL-6b4-t | — | Wnt-4 protein |

TABLE 7-continued

STS MAP OF CHROMOSOME 11
Results of searching the six-potential coding frames of 371 cosmid end sequences against the
protein sequence databases with BLAST-X

| Likely significance sequence name | map position | potential homologue |
|---|---|---|
| cSRL-7e6-t | — | olfactory receptor protein |

Note: Matches are grouped into several categories of likely significance from certain to marginal.
[a]The D11s384 sequence was determined manually and is not part of the 371 sequences determined with automated techniques
[b]Two significant matches, from the same gene family, were found to the same cosmid.
[c]This cosmid was derived from hamster based on PCR amplification results.

The alignments of mine of the best matches are shown in FIG. 9 including matches to mitochondrial acetoacetyl-CoA thiolase, UDP-N-acetylglucosamine-dolichyl-phosphate N-acetylglucosamine phosphotransferase, postysynaptic density protein (and the related discs-large tumor suppressor), zinc finger protein ZFP-37, retrovirus related pol polyptotein, opioid binding protein/cell adhesion molecule, the env polyprotein from feline endogenous virus ECE1, mitochondrial carnitine palmitoytransferase II precursor, and the trans-acting T-cell specific transcription factor GATA-3. The zinc finger protein match is probably not of a human genomic DNA origin since PCR amplification with primers predicted from its nucleotide sequence only generate specific products from hamster DNA. One sequence fragment from a cosmid containing the marker D11S384 was determined with manual methods and exactly matched 72 bases of mitochondrial acetoacetyl-CoA thiolase exon six, mapping this gene to 11q23.1 or FLpter 0.78. This gene was recently localized independently to chromosome 11q22.3-q23.1, in agreement with the localization of this sequence, by traditional mapping methods. The detection of a DNA sequence encoding a protein fragment with 97% protein sequence identity (68/70 amino acids) to the hamster UDP-N-acetylglucosamine-dolichyl-phosphate N-acetylglucosaminephosphotransferase strongly suggests that the human homolog of this enzyme, or a highly conserved pseudogene, is located on chromosome 11q23.3. The remaining protein sequence matches range from posible to marginally significant. The significance of some of the detected matches is remarkable and makes gene localization to these regions likely.

The identification of eight putative new genes from 371 cosmid end sequences corresponds to a 2% gene identification rate and the 19 likely or possible genes corresponds to 5% (Table 7; FIGS. 9A and 9B). In comparison, the rate of gene identification from brain cDNA sequencing is about 14%. Strategies for sequencing cDNA libraries suffer from the problem of sequencing the same cDNA multiple times due to the differential abundance of mRNAs. As demonstrated here, random genomic sequencing is associated with a reasonablerate of gene identification (2–5%) coupled with direct gene mapping, and thus is considerd to be an advantageous strategy for further characterization of cosmid and YAC clone maps. STSs prepared by the methods described herein, will provide a useful reagent for further physical mapping, for constructing YAC contigs using STS content mapping, and for further DNA sequence analysis. In addition, automated fluorescent sequencing of randomly chosen cosmid clones is a rapid and powerful tool for generating PCR detectable markers as well as defining the location of putative genes. Theoretical analysis of the strategy of STS content mapping (Arratia et al., 1991, *Genomics*, 11:806–827; Palazzolo et al., 1991, *Proc. Natl. Acad. Sci., USA*, 88:8034–8038) suggests that this number of unique and uniformity distributed markers will seve as an appropriate starting point for future physical analysis.

In summary, sequence were determined from the ends of chromosome 11 specific cosmids by automated sequencing without intermediate subcloning. The STSs and cosmids were mapped by in situ hybridization, somatic cell hybrid analysis or both. This effort generated 370 STSs specificfor human chromosome 11 and regionally mapped most of them. Sixty-eight percent of these STSs (251/370) were produced from new chromosome 11 sequences; 18% (68/370) represented sequences derived from cloned genes; 8% (29/370) were based upon STS markers deposited and available from GDB. The latter were retested with our set standard conditions to allow integration of this map with the results of other groups.

While the invention has been described in detail with reference to certain preferred embodiments thereof, it will be understood that modifications and variations are within the spirit and scope of that which is described and claimed.

That which is claimed is:

1. A method for sequencing complex genomes, said method comprising:

(1) sequencing at least 100 nucleotides from the end of each member of a library of cosmid clones, wherein said cosmid clones are prepared by inserting genomic DNA fragments into cosmid vectors, and wherein the cosmid vectors include sequences of nucleotides that flank at least one end of the inserted DNA, and that serve as transcription initiation sites for the synthesis of nucleic acids specific to the ends of the inserted DNA, (2) determining the relative spatial relationship between the cosmid clones, and (3) assembling a sequence sampled map by correlating the end-specific nucleotide sequence information with the relative spatial relationship between the cosmids.

2. A method according to claim 1 wherein the relative spatial relationship between the cosmids has been determined prior to sequencing the end-specific nucleotides of each member of a library of cosmid clones.

3. A method according to claim 1 wherein the relative spatial relationship between the cosmids is determined by the cosmid multiplex analysis method.

4. A method according to claim 1 wherein the relative spatial relationship between the cosmids is determined by restriction-fragment-length mapping of the cosmids.

5. A method according to claim 1 wherein at least 250 nucleotides are sequence from the end of the cosmid clones.

6. A method according to claim 1 wherein said cosmid clones are generated in cosmid vectors allowing for the synthesis of end-specific nucleic acid sequences directly from at least one end of DNA fragments inserted therein.

7. A method according to claim 6 wherein said cosmid vectors comprise at least one promoter specific for a bacteriophage RNA polymerase and a cloning site allowing for the insertion of DNA fragments, said promoter being positioned operatively for transcription of a DNA fragment inserted into said cloning site.

8. A method according to claim 7 wherein said cosmid vectors comprise two oppositely oriented promoters, each of which is specific for a bacteriophage RNA polymerase, positioned on two sides of said cloning site, operatively for transcription of a DNA fragment inserted into said cloning site.

9. A method according to claim 8 wherein each of said bacteriophage RNA polymerase-specific promoters is selected from the group consisting of promoters specific for bacteriophage T7 RNA polymerase, and promoters specific for bacteriophage T3 RNA polymerase.

10. A method according to claim 9 wherein said cosmid vector is selected from the group consisting of pWE8, pWE10, pWE15, and pWE16.

11. A method according to claim 6 wherein said cosmid vectors comprise at least two cos sites.

12. A method according to claim 11 wherein said cos sites are separated by unique restriction sites.

13. A method according to claim 12 wherein said cosmid vector is selected from the group consisting of sCOS-1, sCOS-2, sCOS-4, and derivatives thereof.

14. A method for sequencing complex genomes, said method comprising:

(1) preparing a genomic library of cosmid clones by inserting DNA fragments from said genome into cosmid vectors, wherein the cosmid vectors include sequences of nucleotides that flank at least one end of the inserted DNA, and that serve as transcription initiation sites for the synthesis of end-specific probes, (2) arranging the cosmid clones, whereby each clone may be identified and replicas of said arrangement may be reproduced, (3) pooling portions of said cosmid clones and synthesizing pools of mixed end-specific probes from the DNA inserts that have been prepared from said pooled clones, wherein each pool contains fewer than all of the cosmid clones in the library, but all of the cosmid clones in the library are included in at least one pool, (4) hybridizing each pool of probes to a replica of said arranged cosmid clones and identifying the cosmid clones in each replica that hybridize to the probes, wherein said identified clones include the pooled cosmid clones and cosmid clones that contain DNA inserts that overlap with the DNA inserts in the pooled clones, (5) identifying the cosmid clones from among those identified in step (4) that hybridize to two or more pools of probes, thereby identifying groups of cosmid clones that include overlapping DNA, (6) assembling contigs from said groups, and (7) sequencing the fragment ends of the DNA inserts of each of the overlapping cosmid clones.

15. A method according to claim 14 wherein cross-hybridizing clones are identified by comparing the data sets obtained from two groups of cosmid clones containing at least one common clone, and repeating the pairwise comparison with other groups of clones containing at least one common clone.

16. A method according to claim 14 wherein said cosmid clones are pooled according to the rows and columns of a two-dimensional matrix, and said mixed end-specific probes are hybridized to a replica of the entire matrix.

17. A method according to claim 14 wherein said cosmid clones are pooled according to the planes intersecting with a three-dimensional matrix, and said mixed end-specific probes are hybridized to a replica of the entire matrix.

18. A method according to claim 14 wherein said cosmid clones are generated in cosmid vectors allowing for the synthesis of end-specific RNA sequences directly from at least one end of DNA fragments inserted therein.

19. A method according to claim 18 wherein said cosmid vectors comprise at least one promoter specific for a bacteriophage RNA polymerase and a cloning site allowing for the insertion of DNA fragments, said promoter being positioned operatively for transcription of a DNA fragment inserted into said cloning site.

20. A method according to claim 14 wherein said cosmid vectors comprise two oppositely oriented promoters, each of which is specific for a bacteriophage RNA polymerase, positioned on two sides of said cloning site, operatively for transcription of a DNA fragment inserted into said cloning site.

* * * * *